(12) United States Patent
Jenkins et al.

(10) Patent No.: US 10,071,191 B2
(45) Date of Patent: *Sep. 11, 2018

(54) NASAL FLUID MANAGEMENT DEVICE

(71) Applicant: Acclarent, Inc., Irvine, CA (US)

(72) Inventors: Thomas R. Jenkins, Alameda, CA (US); Jessica M. Liberatore, San Mateo, CA (US); Randy J. Kesten, Mountain View, CA (US); Radit Tantisira, Menlo Park, CA (US)

(73) Assignee: Acclarent, Inc., Irvine, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 15/204,168

(22) Filed: Jul. 7, 2016

(65) Prior Publication Data
US 2016/0310647 A1    Oct. 27, 2016

Related U.S. Application Data

(63) Continuation of application No. 14/199,338, filed on Mar. 6, 2014, now Pat. No. 9,408,955, which is a (Continued)

(51) Int. Cl.
*A61M 1/00* (2006.01)
*A61F 13/38* (2006.01)
(Continued)

(52) U.S. Cl.
CPC ....... *A61M 1/0058* (2013.01); *A61B 17/1204* (2013.01); *A61B 17/1219* (2013.01);
(Continued)

(58) Field of Classification Search
CPC .......... A61B 17/12036; A61B 17/1204; A61B 17/12104; A61B 17/12168;
(Continued)

(56) References Cited

U.S. PATENT DOCUMENTS 3,394,702 A    7/1968 Heimlich et al.
3,519,364 A    7/1970 Truhan
(Continued)

FOREIGN PATENT DOCUMENTS

WO    WO 2013/021273 A1    2/2013

OTHER PUBLICATIONS

U.S. Appl. No. 14/193,134.
(Continued)

*Primary Examiner* — Adam Marcetich
(74) *Attorney, Agent, or Firm* — Frost Brown Todd LLC

(57) ABSTRACT

An apparatus comprises a body and a conduit. The body comprises an absorbent material. The conduit is in fluid communication with the body. The conduit has a suction opening positioned within the absorbent material. The conduit is operable to draw fluid away from the absorbent material. The apparatus may be positioned within the posterior choana or the nasopharynx of a patient using a deployment instrument. The apparatus may prevent fluids from draining from the nasal cavity into the patient's throat. In some instances, the apparatus is used as a plug during a sinus irrigation procedure to prevent irrigation fluid from traveling down the patient's throat.

20 Claims, 39 Drawing Sheets

Related U.S. Application Data continuation-in-part of application No. 14/193,134, filed on Feb. 28, 2014, now Pat. No. 9,604,041, which is a continuation-in-part of application No. 14/039,387, filed on Sep. 27, 2013, now Pat. No. 9,408,756, which is a continuation-in-part of application No. 13/832,180, filed on Mar. 15, 2013, now abandoned.

(51) Int. Cl.
| | |
|---|---|
| *A61M 39/00* | (2006.01) |
| *A61B 17/12* | (2006.01) |
| *A61B 17/24* | (2006.01) |
| *A61B 17/00* | (2006.01) |

(52) U.S. Cl.
 CPC .. *A61B 17/12036* (2013.01); *A61B 17/12104* (2013.01); *A61B 17/12168* (2013.01); *A61B 17/24* (2013.01); *A61F 13/38* (2013.01); *A61M 1/008* (2013.01); *A61B 2017/00738* (2013.01); *A61F 13/385* (2013.01)

(58) Field of Classification Search
 CPC ............... A61B 17/1219; A61B 17/24; A61B 2017/00738; A61B 13/38; A61B 13/385; A61B 1/0058; A61B 1/008
 See application file for complete search history.

(56) References Cited

U.S. PATENT DOCUMENTS

| | | | |
|---|---|---|---|
| 3,520,300 | A | 7/1970 | Flower, Jr. |
| 3,595,241 | A | 7/1971 | Sheridan |
| 3,766,924 | A | 10/1973 | Pidgeon |
| 3,935,863 | A | 2/1976 | Kliger |
| 4,895,559 | A | 1/1990 | Brennan |
| 4,950,280 | A | 8/1990 | Brennan |
| 5,085,633 | A | 2/1992 | Hanifl et al. |
| 5,094,616 | A | 3/1992 | Levenson |
| 5,391,179 | A | 2/1995 | Mezzoli |
| 5,599,330 | A | 2/1997 | Rainin |
| 5,628,735 | A | 5/1997 | Skow |
| 5,827,224 | A | 10/1998 | Shippert |
| 5,842,971 | A | 12/1998 | Yoon |
| 5,975,897 | A * | 11/1999 | Propp .................. A61C 17/043 433/91 |
| 6,068,477 | A | 5/2000 | Mahlmann |
| 6,099,493 | A | 8/2000 | Swisher |
| 6,558,344 | B2 | 5/2003 | McKinnon |
| 6,602,218 | B2 | 8/2003 | Yoon |
| 6,620,132 | B1 | 9/2003 | Skow |
| 7,175,594 | B2 | 2/2007 | Foulkes |
| 7,314,326 | B2 | 1/2008 | Rosenberg |
| 7,335,023 | B2 | 2/2008 | Mahlmann |
| 7,347,691 | B1 | 3/2008 | Kelly |
| 7,361,168 | B2 | 4/2008 | Makower |
| 7,464,713 | B2 | 12/2008 | Fabian |
| 7,520,872 | B2 | 4/2009 | Biggie et al. |
| 7,845,944 | B2 | 12/2010 | DiGasbarro |
| 7,931,651 | B2 | 4/2011 | Webb et al. |
| 8,029,498 | B2 | 10/2011 | Johnson et al. |
| 8,267,918 | B2 | 9/2012 | Johnson |
| 8,267,951 | B2 | 9/2012 | Whayne et al. |
| 8,292,875 | B2 | 10/2012 | Kennard |
| 8,454,603 | B2 | 6/2013 | Webb et al. |
| 8,623,047 | B2 | 1/2014 | Cornet et al. |
| 8,715,267 | B2 | 5/2014 | Bengston et al. |
| 8,740,844 | B2 | 6/2014 | Freyman |
| 8,905,922 | B2 | 12/2014 | Makower et al. |
| 9,039,680 | B2 | 5/2015 | Makower et al. |
| 9,101,384 | B2 | 8/2015 | Makower et al. |
| 9,101,515 | B2 | 8/2015 | Odermatt et al. |
| 9,125,766 | B2 | 9/2015 | Swain et al. |
| 9,155,492 | B2 | 10/2015 | Jenkins et al. |
| 9,265,913 | B2 | 2/2016 | Fallin et al. |
| 9,408,756 | B2 | 8/2016 | Jenkins et al. |
| 9,408,955 | B2 | 8/2016 | Jenkins et al. |
| 9,604,041 | B2 | 3/2017 | Jenkins et al. |
| 2001/0025155 | A1* | 9/2001 | Yoon ................ A61B 17/00234 604/1 |
| 2003/0109855 | A1 | 6/2003 | Solem et al. |
| 2004/0020492 | A1 | 2/2004 | Dubrul et al. |
| 2004/0265040 | A1* | 12/2004 | Rosenberg .......... A61M 35/003 401/203 |
| 2006/0271060 | A1 | 11/2006 | Gordon |
| 2007/0027414 | A1 | 2/2007 | Hoffman et al. |
| 2007/0049860 | A1* | 3/2007 | Seminara ......... A61B 17/00234 604/1 |
| 2007/0088326 | A1 | 4/2007 | Kennedy |
| 2007/0218101 | A1* | 9/2007 | Johnson .................. A61B 17/88 424/423 |
| 2007/0267011 | A1 | 11/2007 | Deem et al. |
| 2009/0012425 | A1 | 1/2009 | Dodge et al. |
| 2009/0204142 | A1 | 8/2009 | Becker |
| 2010/0030031 | A1 | 2/2010 | Goldfarb et al. |
| 2011/0004057 | A1 | 1/2011 | Goldfarb et al. |
| 2011/0151405 | A1 | 6/2011 | Dombrowski |
| 2013/0104324 | A1* | 5/2013 | Greer, Jr. ............. A61M 35/006 15/104.93 |
| 2013/0178785 | A1 | 7/2013 | Papay et al. |
| 2014/0276626 | A1 | 9/2014 | Jenkins et al. |
| 2014/0276654 | A1 | 9/2014 | Jenkins |
| 2014/0358059 | A1* | 12/2014 | Jones .................... A61M 37/00 604/2 |

OTHER PUBLICATIONS

Ozer, et al., 'A Novel Laparoscopic Suction Device for Applying Precise Aspiration During Laparoscopic Surgery: Sponge-Tip Suction Tube' Journal of Laparoendoscopic &Advanced Surgical Techniques, 2008, vol. 18, No. 5, pp. 747-750.

Rhinology Products, Boston Medical Products, www.bosmed.com, [date of publication unknown], pp. 1-16.

International Search Report and Written Opinion dated Sep. 15, 2014 for Application No. PCT/US2014/022390, 15 pages.

International Preliminary Report on Patentability dated Sep. 15, 2015 re Application No. PCT/US2014/022390, 9 pages.

U.S. Appl. No. 61/725,523, filed Nov. 17, 2013.

U.S. Appl. No. 13/832,180.

* cited by examiner

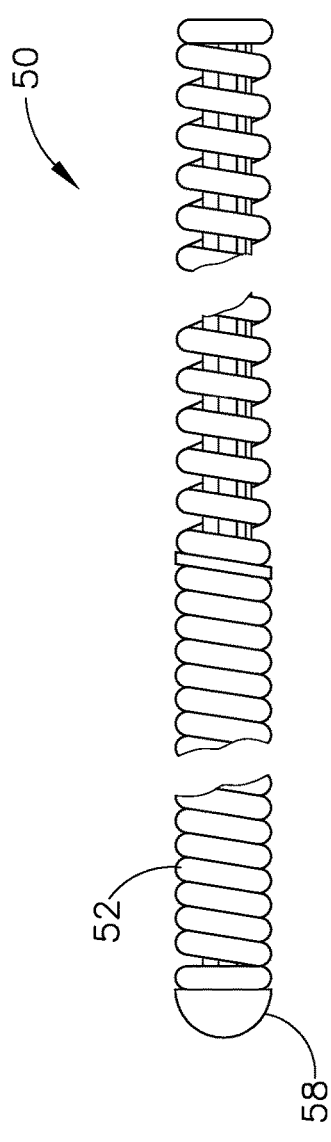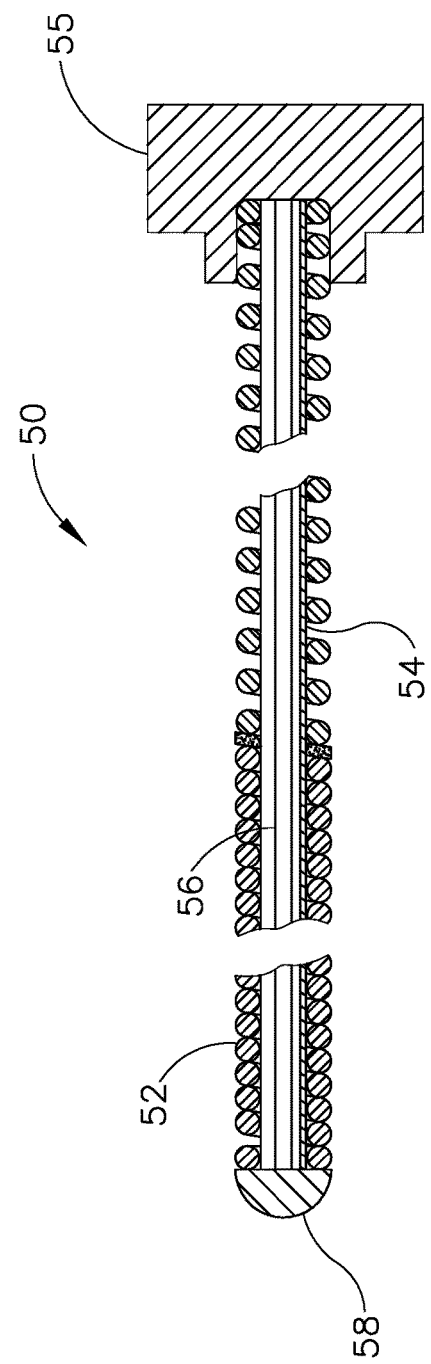
Fig.2
Fig.3

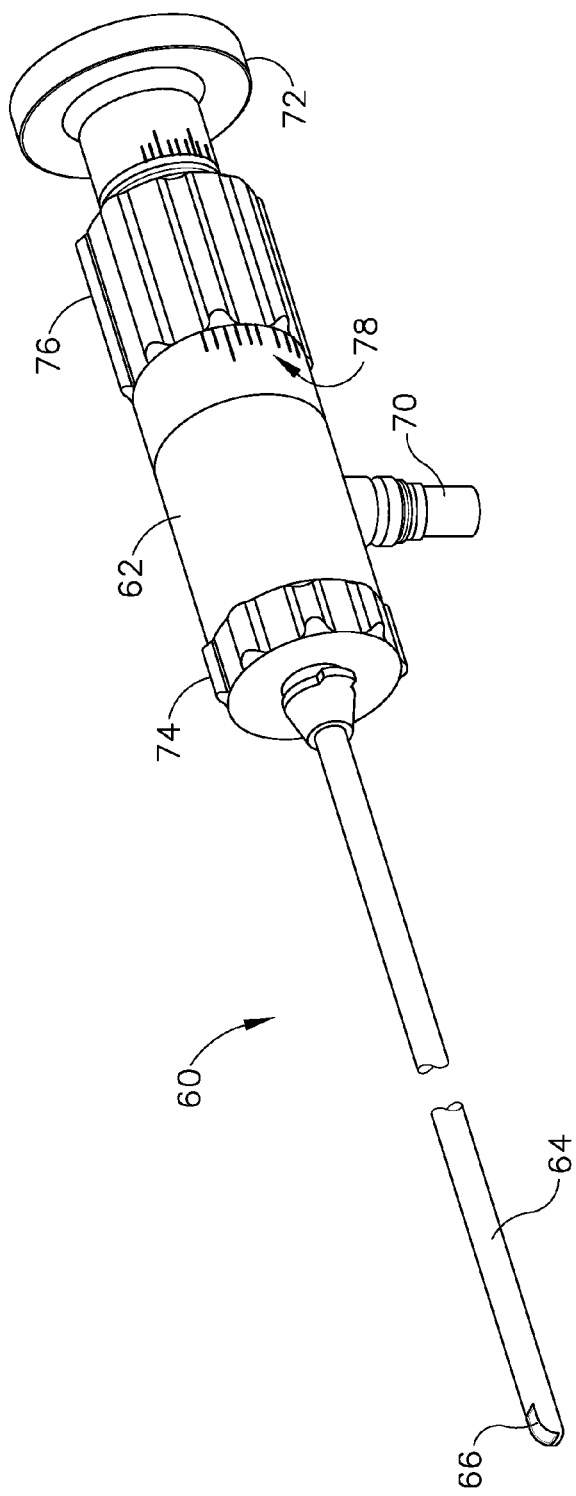
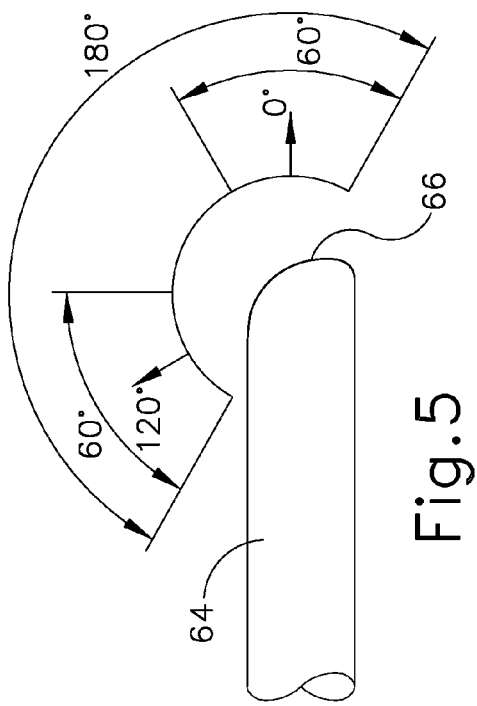
Fig.4
Fig.5

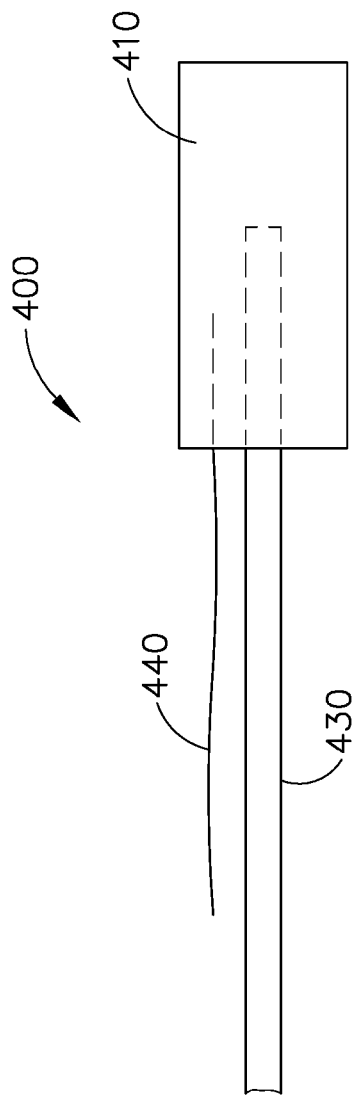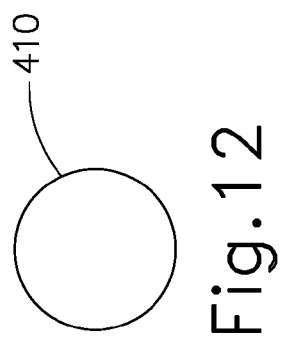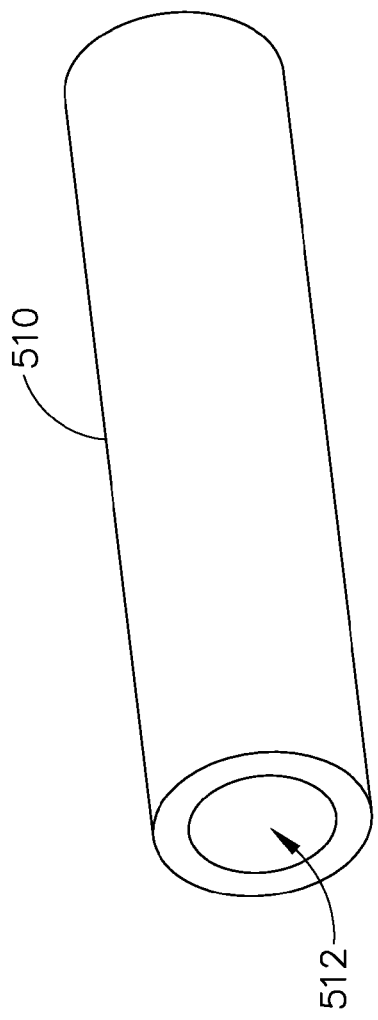

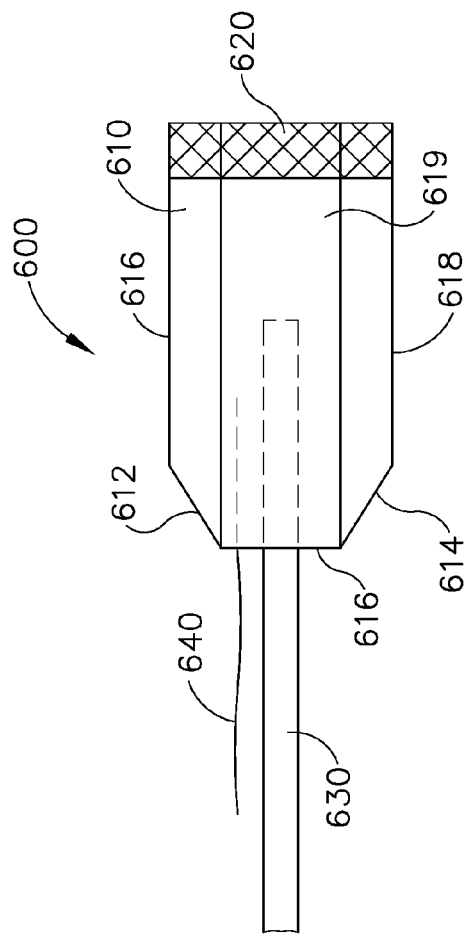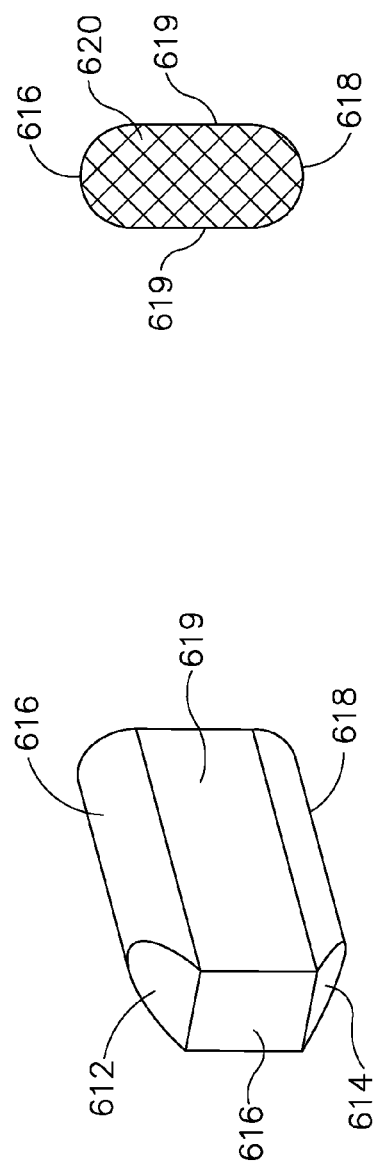

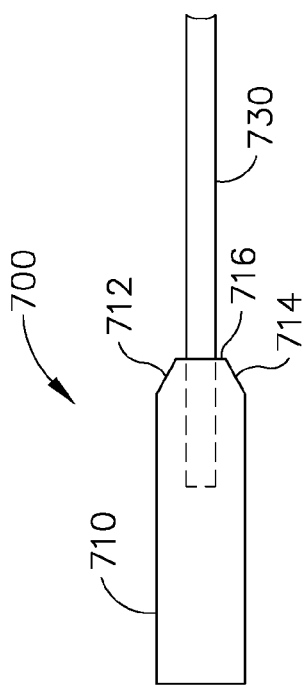
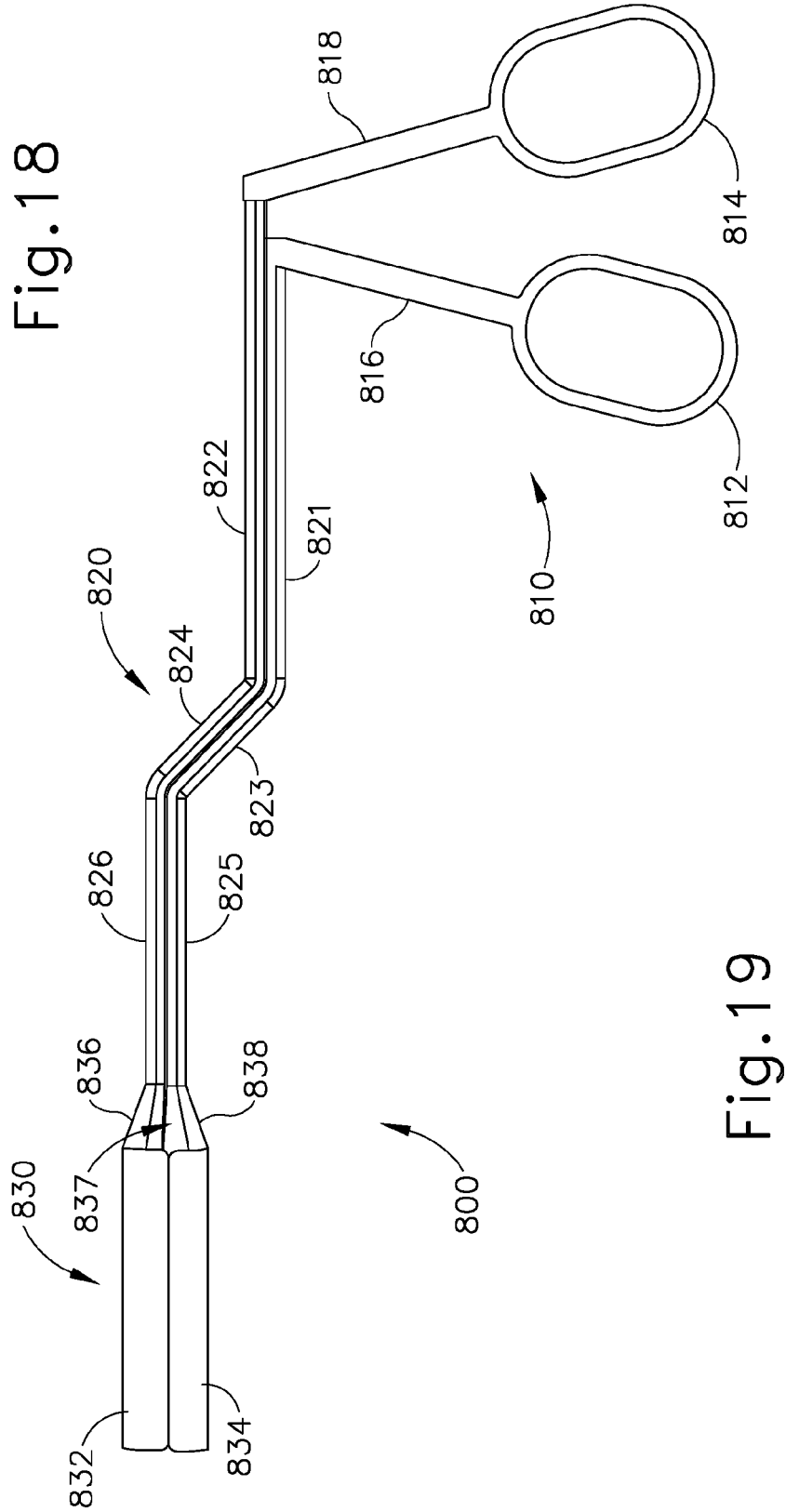

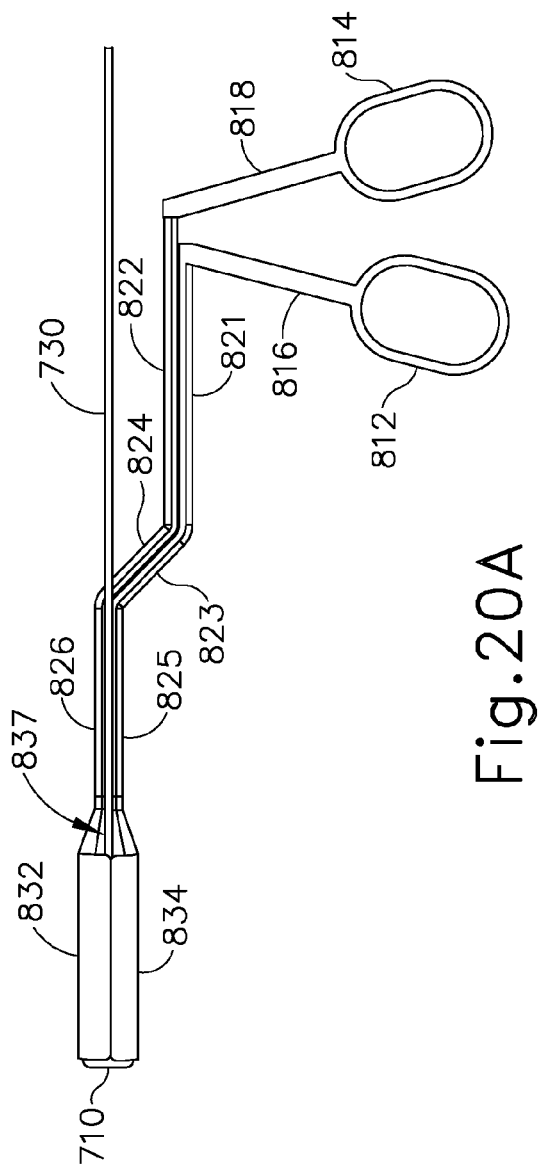
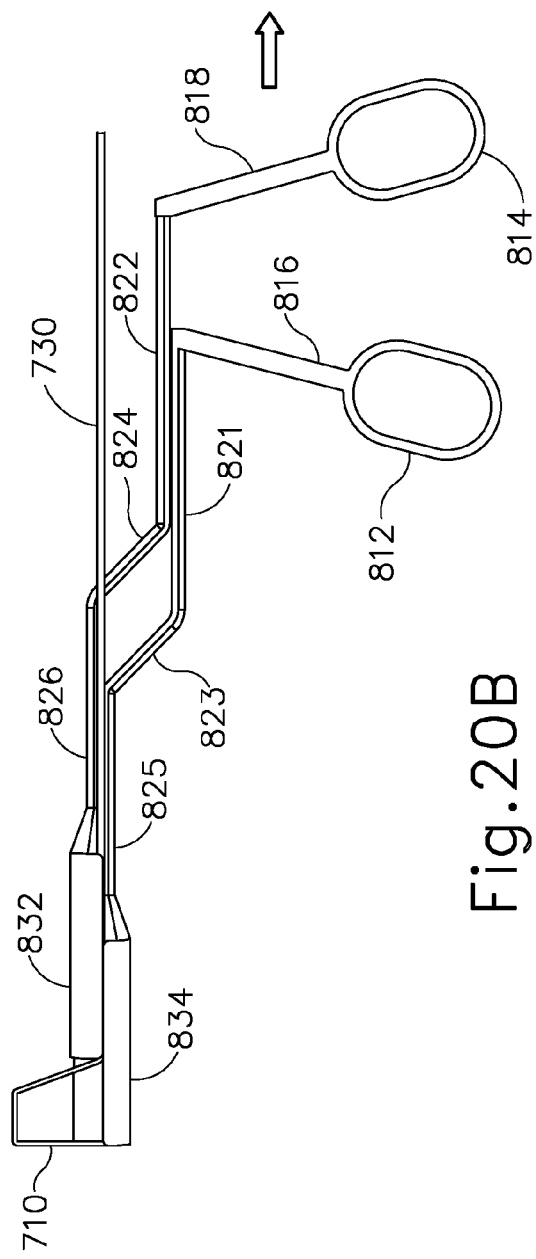
Fig.20A
Fig.20B

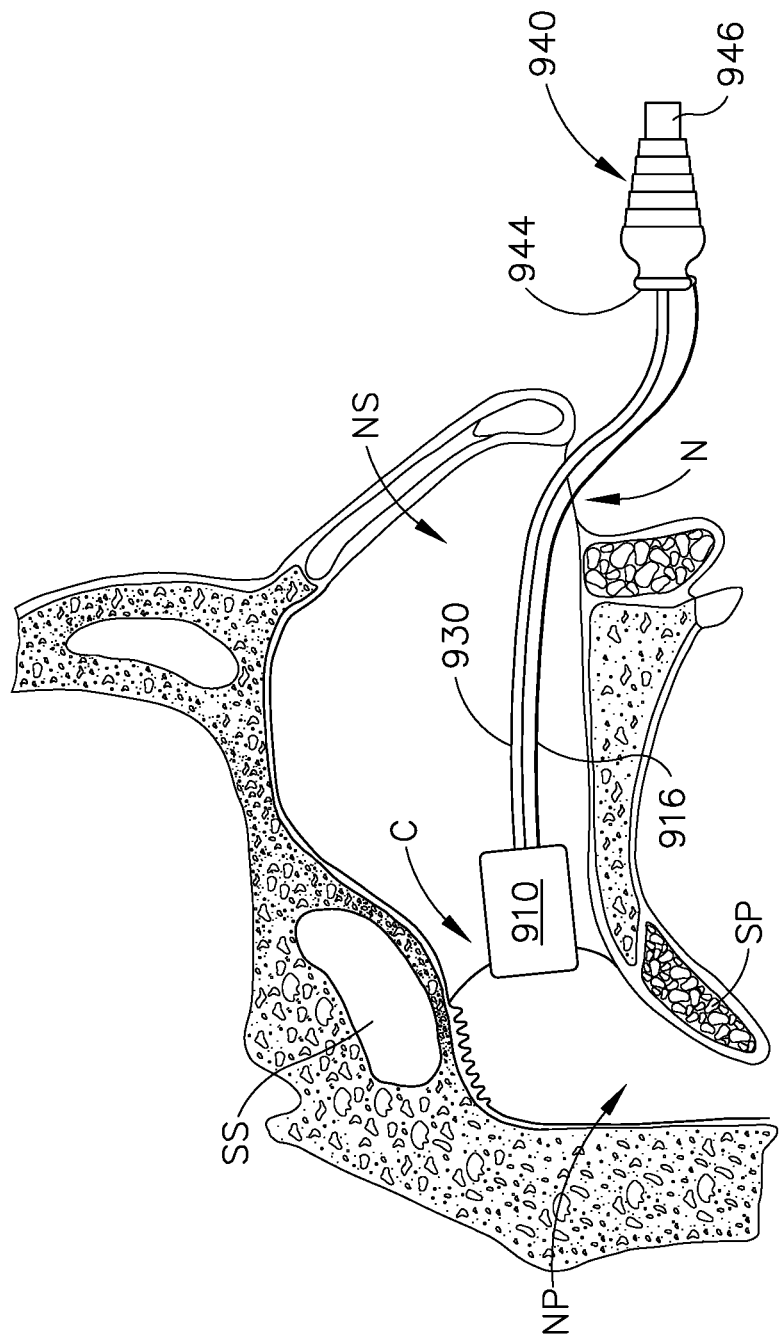

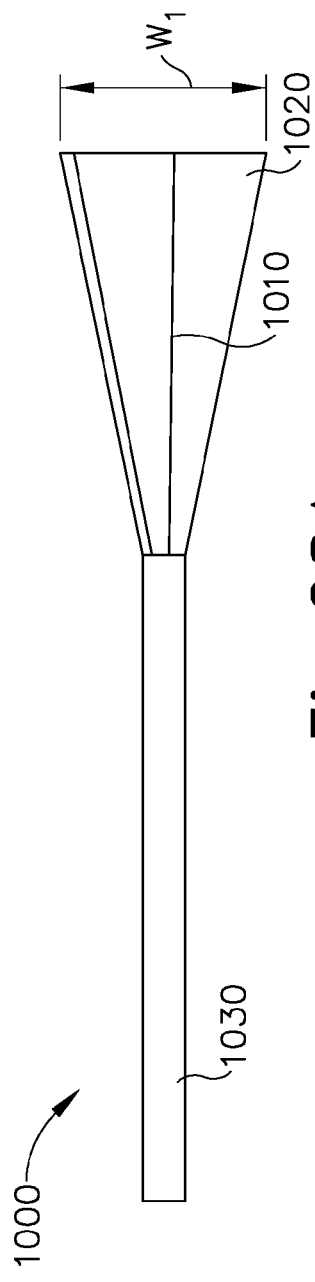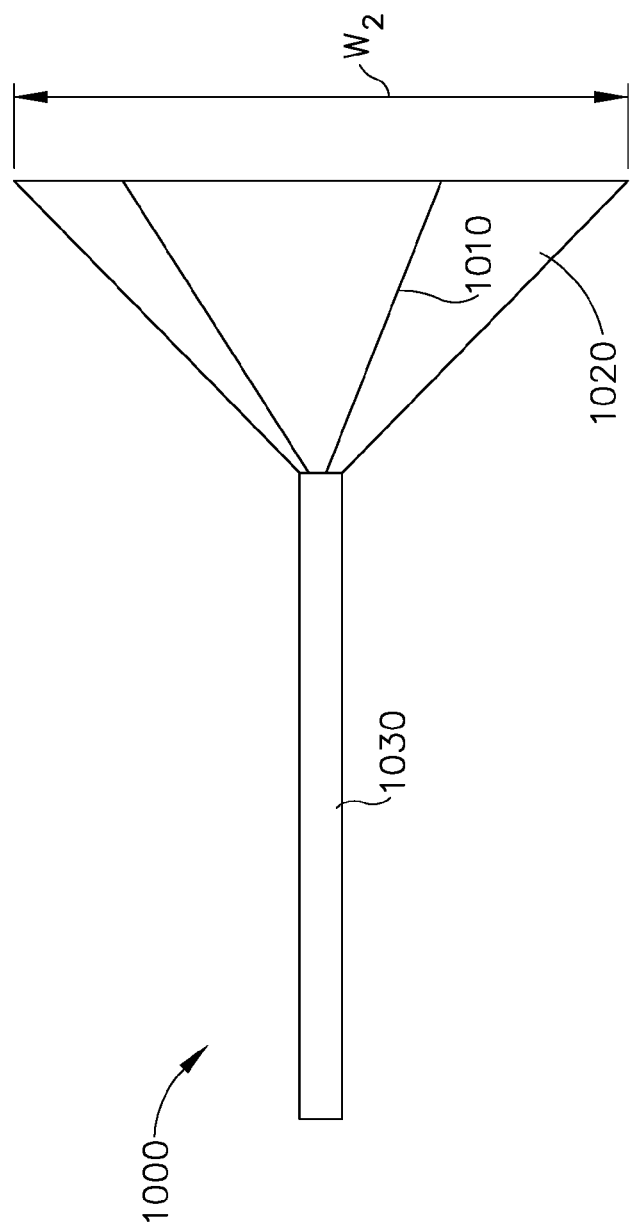
Fig.28A
Fig.28B

NASAL FLUID MANAGEMENT DEVICE

PRIORITY

This application is a continuation of U.S. patent application Ser. No. 14/199,338, entitled "Nasal Fluid Management Device," filed on Mar. 6, 2014, issued as U.S. Pat. No. 9,408,955 on Aug. 9, 2016, which is a continuation-in-part of U.S. patent application Ser. No. 14/193,134, entitled "Nasal Suction Device," filed Feb. 28, 2014, now U.S. Pat. Pub. No. 2014/0276626, published Sep. 18, 2014, now U.S. Pat. No. 9,604,041, issued Mar. 28, 2017, the disclosure of which is incorporated by reference herein, which is a continuation-in-part of U.S. patent application Ser. No. 14/039,387, entitled "Nasal Suction Device," filed Sep. 27, 2013, now U.S. Pat. No. 9,408,756, issued Aug. 9, 2016, the disclosure of which is incorporated by reference herein, which is a continuation-in-part of U.S. patent application Ser. No. 13/832,180, entitled "Nasal Suction Device," filed Mar. 15, 2013, now U.S. Pat. Pub. No. 2014/0276654, published Sep. 18, 2014, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire maybe provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

In addition to or in lieu of dilating ostia of sinuses, it may be desirable in some instances to irrigate the sinuses to flush contents from the sinuses. For instance, it may be desirable to provide such irrigation for therapeutic purposes and/or in order to clear a site before and/or after a sinuplasty procedure as described herein. Sinus irrigation may be performed using an irrigation catheter that is positioned within the sinus. The irrigation catheter may have one or more distally positioned openings that are configured to emit fluid (e.g., saline) as the fluid is communicated through the irrigation catheter. Examples of devices that may be used to provide sinus irrigation are the Relieva Vortex® and Relieva Vortex® 2 Sinus Irrigation Catheters by Acclarent, Inc. of Menlo Park, Calif. While procedures such as sinus irrigation are performed, it may be desirable to prevent the irrigation fluid and/or flushed debris from traveling down the patient's nasopharynx. This may be attempted using suction devices, occluding devices, and/or other kinds of devices. A variety of devices that may be used to prevent such travel are described in U.S. Pub. No. 2012/0245419, entitled "Devices, Systems and Methods for Diagnosing and Treating Sinusitis and Other Disorders of the Ears, Nose and/or Throat," published Sep. 27, 2012, now U.S. Pat. No. 8,905,922, issued Dec. 9, 2014, the disclosure of which is incorporated by reference herein.

While several instruments and procedures have been made and used for treatment of anatomical passageways in a patient, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a side elevational view of an exemplary illuminating guidewire suitable for use with the dilation catheter system of FIG. 1;

FIG. 3 depicts a side cross-sectional view of the illuminating guidewire of FIG. 2;

FIG. 4 depicts a perspective view of an exemplary endoscope suitable for use with the dilation catheter system of FIG. 1;

FIG. 5 depicts a side elevational view of the distal end of the endoscope of FIG. 4, showing an exemplary range of viewing angles;

FIG. 11 depicts a side elevational view of yet another exemplary suction device that may be used with the irrigation catheter of FIG. 6;

FIG. 12 depicts an end view of the suction device of FIG. 11;

FIG. 13 depicts a perspective view of an outer sheath that may be used with the suction device of FIG. 11;

FIG. 15 depicts a side elevational view of yet another exemplary suction device that may be used with the irrigation catheter of FIG. 6;

FIG. 16 depicts a partial perspective view of a proximal end of a body of the suction device of FIG. 15;

FIG. 17 depicts an end view of a distal end of the suction device of FIG. 15;

FIG. 18 depicts a side elevational view of yet another exemplary suction device that may be used with the irrigation catheter of FIG. 6;

FIG. 19 depicts a side elevational view of a deployment instrument that may be used with the suction device of FIG. 18;

FIG. 20A depicts a side elevational view of the suction device of FIG. 18 inserted within the deployment instrument of FIG. 19;

FIG. 20B depicts a side elevational view of the suction device of FIG. 18 being initially deployed from the deployment instrument of FIG. 19;

FIG. 26A depicts a diagrammatic view of the suction device of FIG. 21 in a compressed state, positioned within a patient's choana;

FIG. 28A depicts a side elevational view of the suction device of FIG. 27 in a compressed state;

FIG. 28B depicts a side elevational view of the suction device of FIG. 27 in an expanded state;

Figure 1:
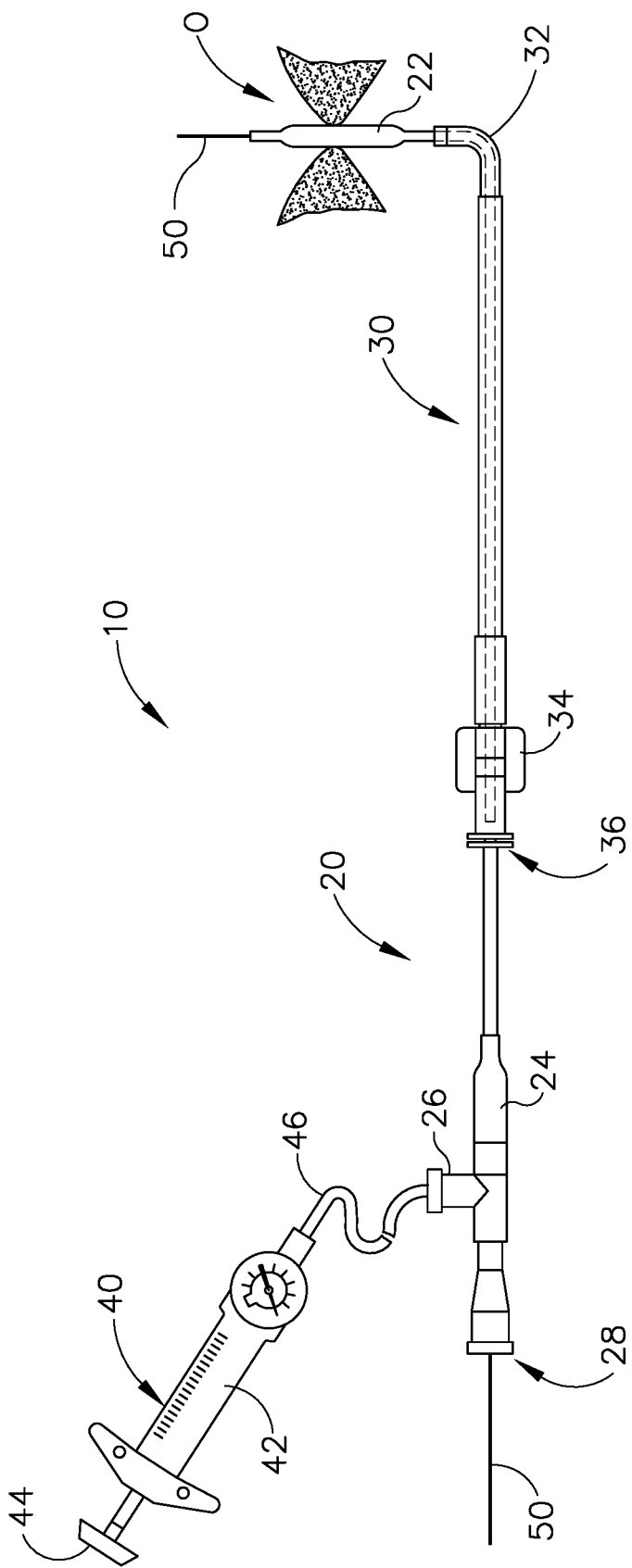
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif.

Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. In some versions, inflator (40) is configured in accordance with at least some of the teachings of U.S. Pat. App. No. 61/725,523, entitled "Inflator for Dilation of Anatomical Passageway," filed Nov. 13, 2012, the disclosure of which is incorporated by reference herein. Other suitable forms that inflator (40) may take will be apparent to those of ordinary skill in the art in view of the teachings herein.

As best seen in FIGS. 2-3, guidewire (50) of the present example comprises a coil (52) positioned about a core wire (54). An illumination wire (56) extends along the interior of core wire (54) and terminates in an atraumatic lens (58). A connector (55) at the proximal end of guidewire (50) enables optical coupling between illumination wire (56) and a light source (not shown). Illumination wire (56) may comprise one or more optical fibers. Lens (58) is configured to project light when illumination wire (56) is illuminated by the light source, such that illumination wire (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination wire (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

II. Overview of Exemplary Endoscope

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein.

By way of example only, endoscope (60) may be configured in accordance with at least some of the teachings of U.S. Pub. No. 2010/0030031, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

III. Exemplary Sinus Irrigation Catheter

Figure 6:
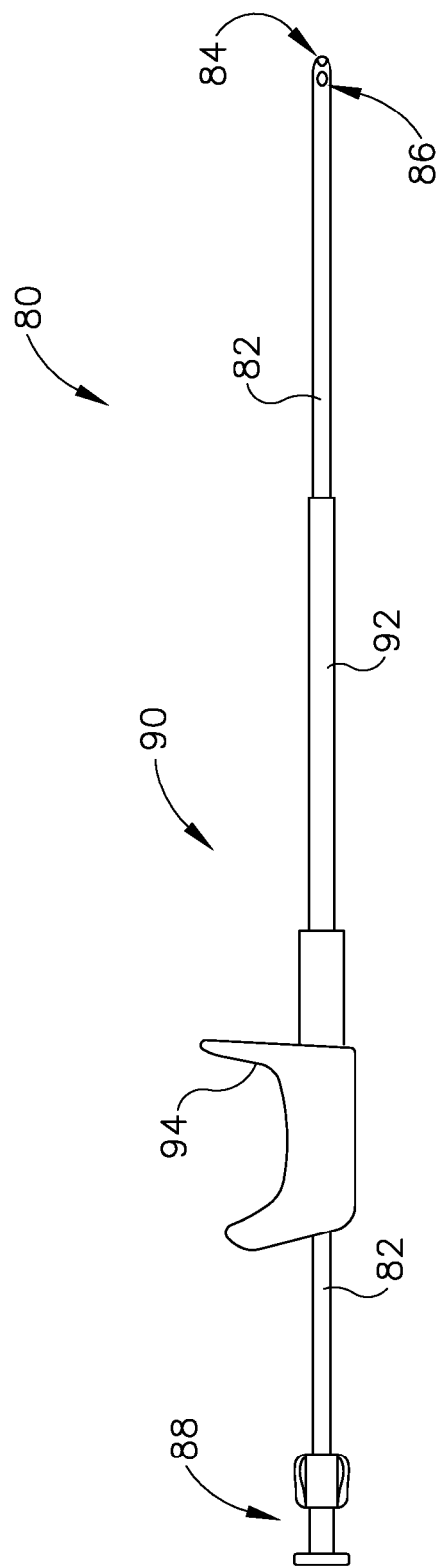
FIG. 6 depicts a side elevational view of an exemplary irrigation catheter that may be used with the dilation catheter system of FIG. 1.

As noted above, it may be desirable in some instances to irrigate the sinuses to flush contents from the sinuses. FIG. 6 shows an exemplary irrigation catheter (80) that may be used to perform sinus irrigation. Irrigation catheter (80) of this example includes a flexible tubular member (82) that has a distal opening (84), a plurality of transverse openings (86) just proximal to distal opening (84), and a proximal fitting (88). Proximal fitting (88) is configured as a standard luer fitting that may be coupled with any suitable fluid source (e.g., a syringe filled with saline, etc.). Fluid communicated through proximal fitting (88) will travel along tubular member (82) and exit via openings (84, 86).

Irrigation catheter (80) of this example further includes a support assembly (90) comprising a support tube (92) and a grip (94). Tubular member (82) is slidably disposed within support assembly (90). Support tube (90) has greater rigidity than tubular member (82) such that support tube (90) provides structural support for tubular member (82) as tubular member (82) is being positioned in a patient. Tubular member (82) may also include indicia along at least part of its length in order to provide visual feedback relating to the depth of insertion of tubular member (82). By way of example only, irrigation catheter (80) may be configured similar to the Relieva Vortex® and Relieva Vortex® 2 Sinus Irrigation Catheters by Acclarent, Inc. of Menlo Park, Calif. Other suitable forms that irrigation catheter (80) may take will be apparent to those of ordinary skill in the art in view of the teachings herein.

Tubular member (82) of the present example is sized for insertion through guide catheter (30). In particular, tubular member (82) may be inserted through guide catheter (30) before dilation catheter (20) has been inserted in guide catheter (30) or after dilation catheter (20) has been removed from guide catheter (30). It should be understood that irrigation catheter (80) may also be advanced along guidewire (50), if desired. In some uses, irrigation catheter (80) is advanced through guide catheter (30) such that openings (84, 86) are positioned near a desired irrigation/flush site. Endoscope (60) and/or illumination from guidewire (50) may be used to provide visualization during the positioning of irrigation catheter (80). Once irrigation catheter (80) is suitably positioned, fluid is communicated along tubular member (82) from proximal fitting (88) to openings (84, 86), such that the fluid is sprayed from openings (85, 86) at the irrigation/flush site. This irrigation procedure may be performed before dilation catheter (20) is used to dilate the ostia (O) and/or after dilation catheter (20) is used to dilate the ostia (O). In some instances, irrigation catheter (80) is used when no dilation procedure is being performed. Various other settings in which irrigation catheter (80) may be used will be apparent to those of ordinary skill in the art in view of the teachings herein.

Figure 7:
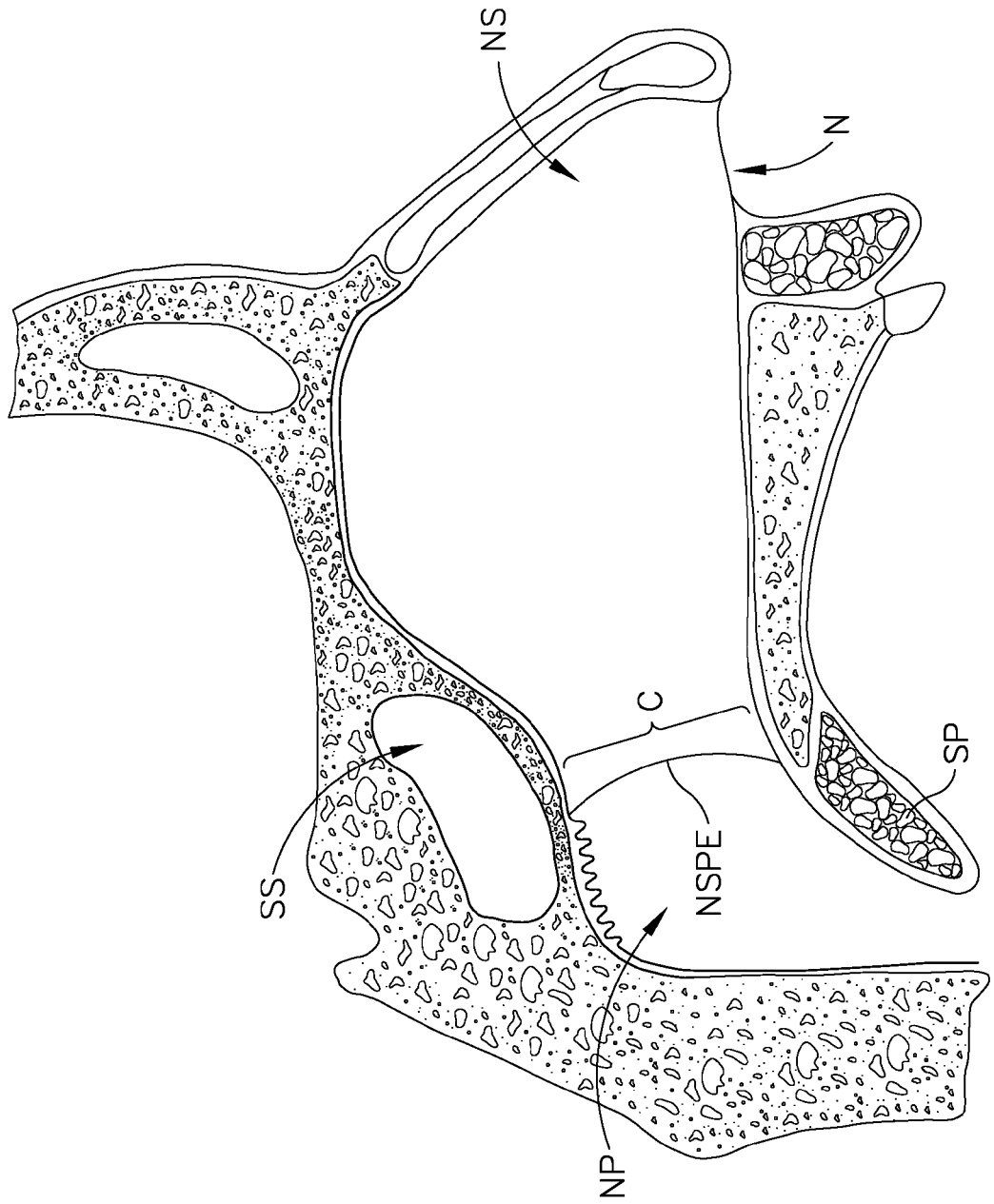
FIG. 7 depicts a left sagittal cross-sectional view of a portion of a human head, showing paranasal anatomical structures.

It should be understood that an irrigation process using irrigation catheter (80) may result in the need for fluid and/or other debris to drain from the irrigation/flush site. Otherwise, the patient may gag, cough, choke, or otherwise experience discomfort. In some instances, the operator may simply have the patient lean forward such that the fluid drains from the patient's nose. FIG. 7 depicts a pathway through which irrigation fluid may reach the patient's throat. In particular, FIG. 7 shows the patient's choana (C), which is a necked-down region of the nasal cavity, generally located posterior to the inferior turbinate (not shown), inferior to the sphenoid sinus (SS), and superior to the soft palate (SP). The choana (C) is generally associated with the posterior end (NSPE) of the nasal septum (NS). The nasopharynx (NP) is caudal to the choana (C) and posterior end (NSPE) of the nasal septum (NS). The nasopharynx (NP) leads to the patient's throat. It should therefore be understood that irrigation fluid may travel into the throat via the choana (C) and the nasopharynx (NP). An occlusion device may be positioned within the patient's nasopharynx (NP), in the posterior choana (C), or elsewhere to prevent the fluid from draining down the patient's throat. In addition or in the alternative, a suction device may be used to draw away the drainage. Additional devices that may be used to handle drainage from an irrigation process will be described in greater detail below; while still other examples will be apparent to those of ordinary skill in the art in view of the teachings herein.

IV. Exemplary Nasal Suction Device

Figure 8:
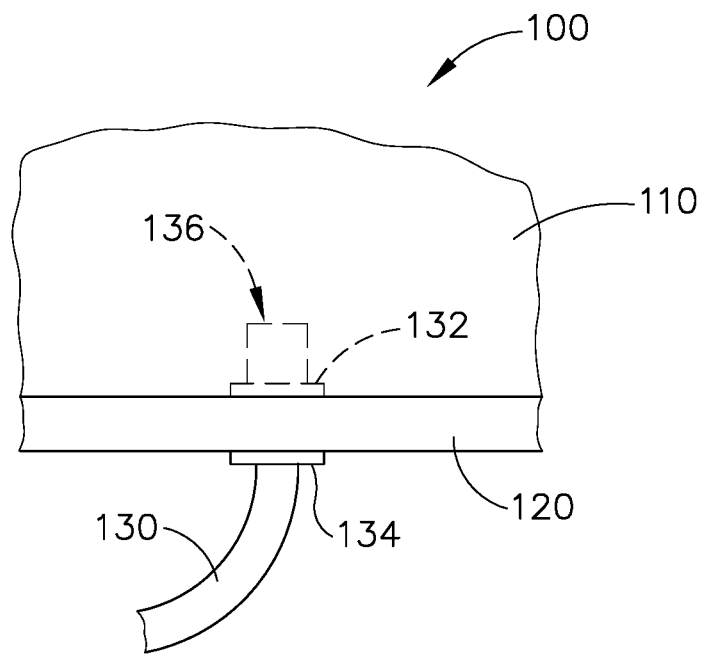
FIG. 8 depicts a side elevational view of an exemplary suction device that may be used with the irrigation catheter of FIG. 6.

FIG. 8 shows an exemplary suction device (100) that may be used to handle drainage from an irrigation procedure performed using irrigation catheter (80) or using some other irrigation device. Suction device (100) of this example comprises an absorbent body (110) secured to a base (120). Body (110) and base (120) are sized to be positioned within the posterior choana or the nasopharynx of a patient. A suction tube (130) is secured to base (120) by a pair of flanges (132, 134), which provide a fluid tight seal at the interface between suction tube (130) and base (120). Suction tube (130) has an open distal end (136). The proximal end of suction tube (130) may be coupled with a suction source (e.g., vacuum pump, vacuum wall outlet, syringe, etc.), such that suction tube (130) may provide suction at open distal end (136). Open distal end (136) is positioned within body (110).

Body (110) is configured to absorb fluids and is also pliable such that body (110) does not cause trauma to the tissue that comes in contact with body (110). In some versions, body (110) is configured to expand as it absorbs fluid, such that body (110) will at least slightly bear outwardly on the inner wall of the anatomical passageway in which body (110) is disposed. This may enable body (110) to generally conform to the shape of the anatomical passageway and avoid fluids leaking past body (110). In some versions, body (110) comprises foam. Various suitable materials and structures that may be used to form body (110) will be apparent to those of ordinary skill in the art in view of the teachings herein.

Base (120) is also pliable and atraumatic, yet base (120) is formed of a nonabsorbent material that will provide a fluid tight seal such that the fluid will not pass through or around base (120) when base (120) is properly positioned within an anatomical passageway such as the posterior choana or the nasopharynx. In some versions, base (120) comprises a membrane. Base (120) may also resiliently bear against the wall of the anatomical passageway, such that base (120) conforms to the shape of the anatomical passageway without providing fluid drainage paths between the outer perimeter of base (120) and the wall of the anatomical passageway. While base (120) is shown as only making up a relatively small portion of the overall thickness of suction device (100), it should be understood that body (110) and base (120) may have any other suitable relative thicknesses. Various suitable materials that may be used to form base (120) will also be apparent to those of ordinary skill in the art in view of the teachings herein.

In an exemplary use, suction device (100) is positioned in a patient's posterior choana or nasopharynx while irrigation catheter (80) is positioned at the irrigation site in the patient's nasal cavity. Suction device (100) is positioned such that body (110) is generally directed toward the patient's nasal cavity while base (120) is generally directed toward the patient's throat. In this example, suction tube (130) exits through the underside of base (120) and is fed along the nasopharynx and out the patient's mouth. Irrigation fluid is then communicated through irrigation catheter (80) while suction is communicated to suction tube (130). The irrigation fluid drains through the patient's nasal cavity and into body (110), which absorbs the fluid. As body (110) absorbs the fluid, suction tube (130) draws the fluid out of body (110) via open distal end (136). This prevents body (110) from becoming oversaturated to the point where suction device (100) no longer effectively plugs the drainage path. The configuration and absorbance of body (110) prevents fluid from flowing quickly past suction tube (130).

Figure 9:
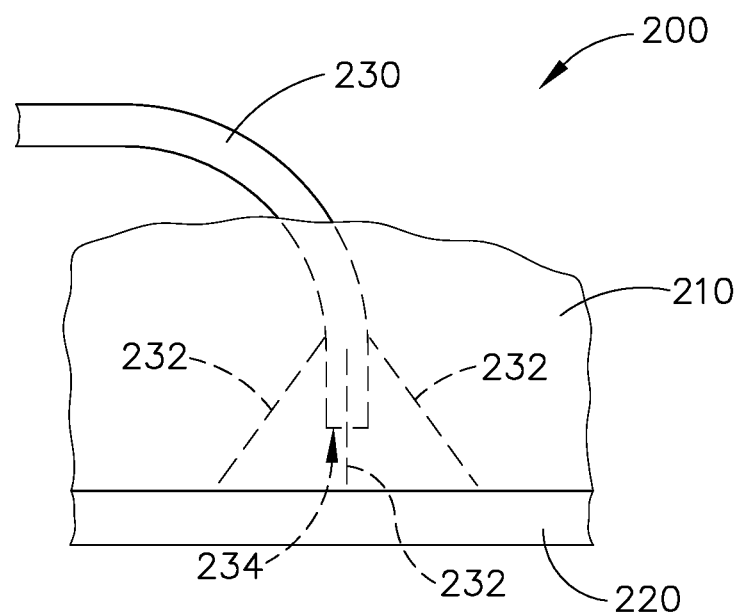
FIG. 9 depicts a side elevational view of another exemplary suction device that may be used with the irrigation catheter of FIG. 6.

FIG. 9 shows another exemplary suction device (200) that may be used to handle drainage from an irrigation procedure performed using irrigation catheter (80) or using some other irrigation device. Suction device (200) of this example is substantially similar to suction device (100) in that suction device (200) comprises an absorbent body (210) secured to a base (220) and a suction tube (230). Absorbent body (210) may be configured an operable just like absorbent body (110) described above. Similarly, base (220) may be configured and operable just like base (120) described above. However, in this example, suction tube (230) enters the top side of body (210) and is secured to base (220) by a plurality of tethers (232). In some other versions, tube (230) is bonded to body (210); and base (220) is bonded to body (210) such that tube (230) is bonded to tube (230) via body (210). Other suitable ways in which body (210), base (220), and body (210) may be secured will be apparent to those of ordinary skill in the art in view of the teachings herein. In the present example, suction tube (230) still also has an open distal end (234) and may be coupled with a suction source at the proximal end of suction tube (230).

In an exemplary use, suction device (200) is positioned in a patient's posterior choana or nasopharynx while irrigation catheter (80) is positioned at the irrigation site. Suction device (200) is positioned such that body (210) is generally directed toward the patient's nasal cavity while base (220) is generally directed toward the patient's throat. In this example, suction tube (230) exits through the patient's nostril. Irrigation fluid is then communicated through irrigation catheter (80) while suction is communicated to suction tube (230). The irrigation fluid drains through the patient's nasal cavity and into body (210), which absorbs the fluid. As body (210) absorbs the fluid, suction tube (230) draws the fluid out of body (210) via open distal end (234). This prevents body (210) from becoming oversaturated to the point where suction device (200) no longer effectively plugs the drainage path.

While suction device (100) has a suction tube (130) exiting the bottom of suction device (100), and suction device (200) has suction tube (130) exiting the top of suction device (200), it should be understood that either suction device (100, 200) may be modified to have its suction tube (130, 230) exit the side of suction device (100, 200) or have some other relationship with body (110, 210).

Figure 10:
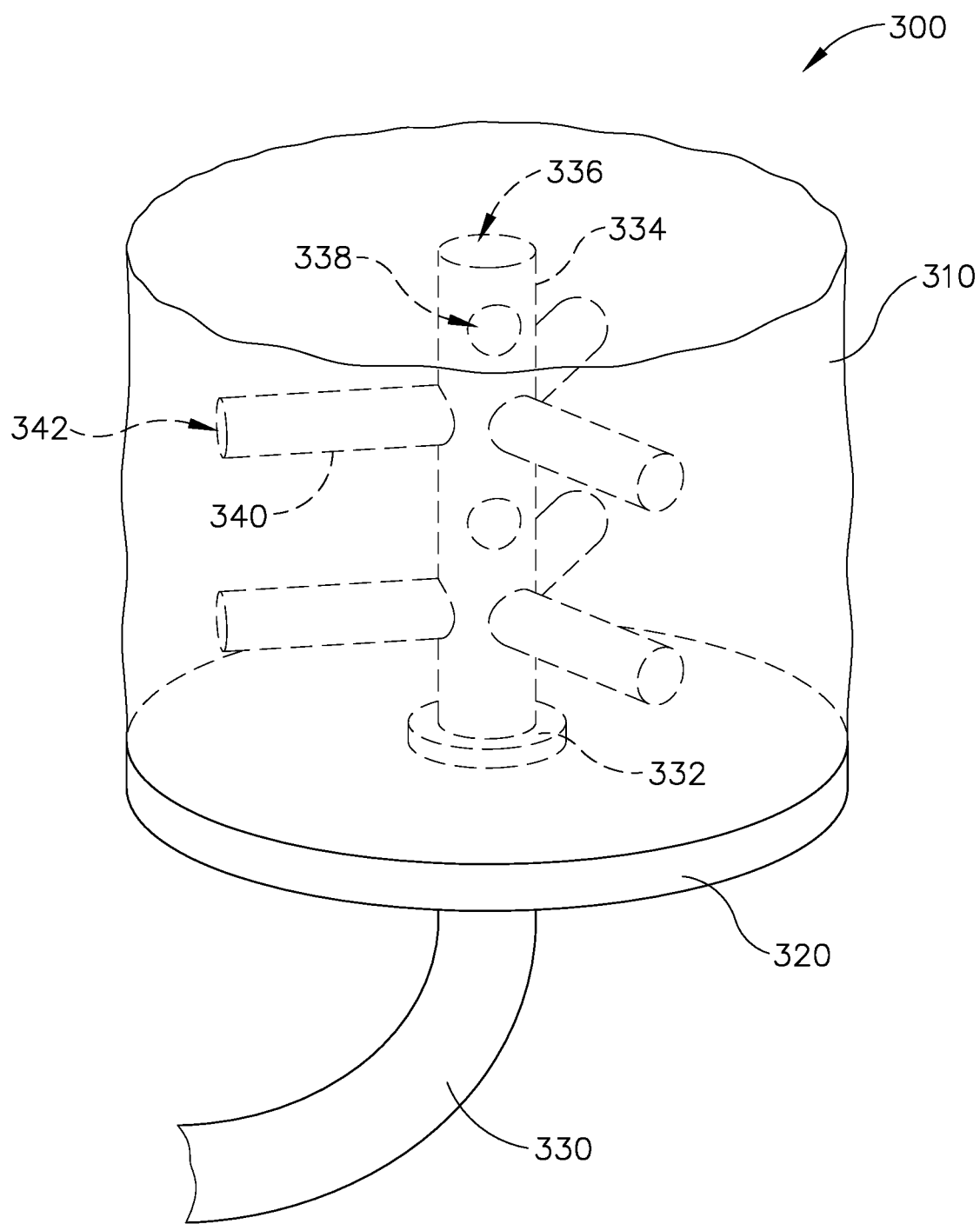
FIG. 10 depicts a perspective view of yet another exemplary suction device that may be used with the irrigation catheter of FIG. 6.

FIG. 10 shows yet another exemplary suction device (300) that may be used to handle drainage from an irrigation procedure performed using irrigation catheter (80) or using some other irrigation device. Suction device (300) of this example is substantially similar to suction devices (100, 200) in that suction device (300) comprises an absorbent body (310) secured to a base (320) and a suction tube (330). Absorbent body (310) may be configured and operable just like absorbent body (110) described above. Similarly, base (320) may be configured and operable just like base (120) described above. In addition, a flange (332) secures suction tube (330) to base (320). However, in this example, the portion of suction tube (330) within body (310) comprises a main trunk portion (334) having a plurality of outwardly extending branches (340). Main trunk portion (334) also includes a distal opening (336) and a plurality of transverse openings (338), all of which are in fluid communication with the interior of suction tube (330).

Branches (340) include distal openings (342) that are also in fluid communication with the interior of suction tube (330). It should be understood that openings (336, 338, 342) provide additional points of suction within body (310), which may assist in drawing fluid from body (310) more effectively than versions having just one suction opening within body (310). It should also be understood that branches (340) may include transverse openings (338), if desired. Furthermore, main trunk portion (334) may lack transverse openings (338). In some other versions, main trunk portion (334) is substantially omitted, such that all branches (340) terminate at a common stump or other kind of interface near flange (332) and extend upwardly and outwardly from the interface. Various suitable configurations and arrangements of branches (340) will be apparent to those of ordinary skill in the art in view of the teachings herein.

Suction device (300) may be used just like suction device (100) described above, including routing suction tube (330) along the nasopharynx and out the patient's mouth. Alternatively, suction tube (330) may exit the top of body (310) similar to suction tube (230) or may have any other suitable relationship with body (310).

It should be understood that with the effective seals provided by suction devices (100, 200, 300), an operator may perform irrigation procedures using a fluid pressure that is substantially higher than the fluid pressure that the operator might otherwise use in cases where a suction wand or other device were the only device used to handle draining irrigation fluid, etc. The substantially higher irrigation fluid pressures enabled by suction devices (100, 200, 300) may result in better cleaning of the sinuses by the irrigation fluid.

While suction devices (100, 200, 300) have been described above as being used in the context of an irrigation procedure, it should be understood that suction devices (100, 200, 300) may be used in a variety of other procedures. Similarly, it should be understood that suction devices (100, 200, 300) may be used to absorb and suction fluids other than irrigation fluid. By way of example only, suction devices (100, 200, 300) may be used to absorb medication (e.g., lidocaine, etc.), blood, water, and/or any other fluid that may otherwise drain through the nasopharynx.

V. Exemplary Nasal Suction Device with a Deployment Instrument

In some instances, it may be desirable to place a suction device (100, 200, 300) into an anatomical passageway (e.g., the posterior choana or the nasopharynx) using a deployment instrument. This may allow suction device (100, 200, 300) to be maneuvered to the desired location and advanced from the deployment instrument; and/or for the deployment instrument to be withdrawn relative to suction device (100, 200, 300) once suction device (100, 200, 300) is in the desired location. Suction device (100, 200, 300) then expands to at least partially bear against the inner wall of the anatomical passageway and prevent fluids from leaking past suction device (100, 200, 300). The examples below include several merely illustrative versions of suction devices with a deployment instrument that may be readily incorporated for use with an irrigation catheter (80) or other irrigation device to handle drainage from an irrigation procedure. It should be understood that the instruments described below may be rigid, flexible, malleable, partially rigid, partially flexible, and/or partially malleable, to facilitate maneuvering of the distal end of the instrument through the paranasal cavity. Other suitable distal end properties and configurations for the instruments described below will be apparent to those of ordinary skill in the art.

It should also be understood that, in some instances, a conventional instrument (e.g., tweezers, bayonet forceps, etc.) may be used to deploy a suction device (100, 200, 300) as described above and/or a suction device (400, 600, 700) as described below. By way of example only, a forceps instrument with a scissor grip may be used to compress and hold a suction device (100, 200, 300, 400, 600, 700). In some instances, a locking feature may be provided to hold the jaws of the forceps in a grasping position. While suction device (100, 200, 300, 400, 600, 700) is grasped and compressed in the jaws of the forceps, the jaws of the forceps and suction device (100, 200, 300, 400, 600, 700) may be dipped in saline in order to wet suction device (100, 200, 300, 400, 600, 700). The forceps may then be maneuvered to position suction device (100, 200, 300, 400, 600, 700) in the patient's choana or nasopharynx, at which point the grip of the forceps may be released to release suction device (100, 200, 300, 400, 600, 700) in place. The released suction device (100, 200, 300, 400, 600, 700) may then expand due to its wetting, then bear into the wall of the choana or nasopharynx. If desired, additional fluid may be added to suction device (100, 200, 300, 400, 600, 700) to enhance the swelling/expansion of suction device (100, 200, 300, 400, 600, 700). As a merely illustrative variation, the jaws of a conventional forceps device may be modified to encompass a greater surface area of the exterior of suction device (100, 200, 300, 400, 600, 700). Other suitable distal end properties and configurations for forceps instruments, the instruments described below, and other instruments that may be used to deploy suction device (100, 200, 300, 400, 600, 700) will be apparent to those of ordinary skill in the art in view of the teachings herein.

A. Exemplary Nasal Suction Device with Outer Sheath

FIGS. 11-12 show an exemplary suction device (400) that is substantially similar to suction devices (100, 200, 300) in that suction device (400) comprises an absorbent body (410) and a suction tube (430). Absorbent body (410) may be configured and operable substantially similar to absorbent body (110) described above. In the present example, body (410) comprises a foam material, such as polyvinyl alcohol (PVA) foam. Body (410) is generally cylindrical and is configured to transition between a compressed state (FIG. 14A) and an expanded state (FIG. 14C). In the present example, body (410) is sufficiently compressible to fit within outer sheath (510), as shown in FIG. 13, when body (410) is in the compressed state. Body (410) may have a length of about 2 inches and a diameter of about 0.2 inches when body (410) is in the compressed state. Other suitable compressed dimensions will be apparent to one with ordinary skill in the art in view of the teachings herein.

Body (410) is sufficiently dense to press against the walls of the posterior choana or the nasopharynx when body (410) is in the expanded state, thereby effectively sealing the posterior choana or the nasopharynx to prevent fluids (e.g., irrigation fluids, etc.) from being communicated into the patient's throat. In the present example, body (410) has a circular profile in the expanded state, with a length of about 1.4 inches and a diameter of about 0.9+/−0.05 inches. It should be understood, however, that body (410) may instead have a non-circular profile. By way of example only, in some versions where body (410) has an ovular profile, elliptical profile, or otherwise elongate profile, body (410) may have a major diameter of about 1.1+/−0.02 inches and a minor diameter of about 0.65+/−0.2 inches. In some such versions where body (410) has an ovular profile, elliptical profile, or otherwise elongate profile, the major diameter is bounded by curves having a radius of curvature of about 0.325 inches. As yet another merely illustrative example, body (410) may have a major diameter of about 0.85+/−0.2 inches and a minor diameter of about 0.45+/−0.2 inches, with the major diameter being bounded by curves having a radius of curvature of about 0.225 inches. Other suitable profile shapes that may be used for an expanded body (410) will be apparent to those of ordinary skill in the art in view of the teachings herein. Similarly, other suitable expanded dimensions for body (410) will be apparent to one with ordinary skill in the art in view of the teachings herein.

Suction tube (430) may be configured and operable substantially similar to suction tube (130) described above. Suction tube (430) is sized to fit within and extend proximally from body (410) such that suction tube (430) is able to provide adequate suction to body (410). By way of example only, suction tube (430) may have an inner diameter of about 0.055 inches and an outer diameter of about 0.079 inches. Other suitable dimensions will be apparent to one with ordinary skill in the art in view of the teachings herein. As shown in FIG. 11, suction tube (430) is placed substantially in the radial center of body (410) such that suction tube (430) extends longitudinally within body (410). Suction tube (430) may extend to a depth of about 1.0+/−0.05 inches into body (410). Other suitable lengths/depths to which suction tube (430) may extend will be apparent to one with ordinary skill in the art in view of the teachings herein.

As shown in FIG. 11, suction device (400) of the present example further comprises a string (440) extending proximally from body (410) such that string (440) may be grasped and pulled to thereby pull suction device (400) out of a patient through the nasal cavity or through the patient's mouth (depending on the orientation string (440) within the patient's choana or the nasopharynx, etc.). By way of example only, string (440) may extend from body (410) by approximately 4 inches or more, approximately 6 inches or more, approximately 10 inches or more, or to any other suitable length. String (440) is positioned off-center within body (410) to accommodate suction tube (430) in the present example. For instance, string (440) may be laterally offset from the center of body (410) by about 0.15+/−0.05 inches. Other suitable offset distances will be apparent to one with ordinary skill in the art in view of the teachings herein.

In some versions, the distal end of string (440) is tied around the proximal end of body (410) instead of extending within body (410). It should be noted that string (440) is merely optional. For instance, an operator may use an instrument, such as forceps, to grasp suction device (400) and thereby remove suction device (400) from a patient. However, even if forceps are used to remove suction device (400) from a patient, string (440) may still be provided as a safety feature such that if device (400) were positioned improperly, string (440) may be grasped to prevent body (410) from slipping from the desired location (e.g., slipping down a patient's throat). In some versions, the proximal end of string (440) is secured to the proximal end of suction tube (430) or outer sheath (510). This would allow suction tube (430) or outer sheath (510) to prevent string (440) from being dragged with body (410) if device (400) were positioned improperly such that body (410) became free from suction tube (430) or outer sheath (510) and traveled into a patient's throat.

FIG. 13 shows an outer sheath (510) that may be used with suction device (400). Outer sheath (510) defines a lumen (512) extending through outer sheath (510) such that suction device (400) may be inserted within lumen (512) of outer sheath (510). In the present example, lumen (512) is sized to fit body (410) of suction device (400) when body (410) is in the compressed state such that body (410) does not slip out of outer sheath (510). Outer sheath (510) is further configured to fit within a nasal cavity. Outer sheath (510) has a circular cross-sectional profile in this example, though it should be understood that sheath (510) may instead have any other suitable cross-sectional profile (e.g., ovular, elliptical, etc.). It should also be understood that sheath (510) may be straight along its full length or may be curved along at least part of its length. Outer sheath (510) may also taper inwardly in the distal direction to allow for easier maneuvering within the nasal cavity. Various suitable configurations for sheath (510) will be apparent to those of ordinary skill in the art in view of the teachings herein.

Figure 14A:
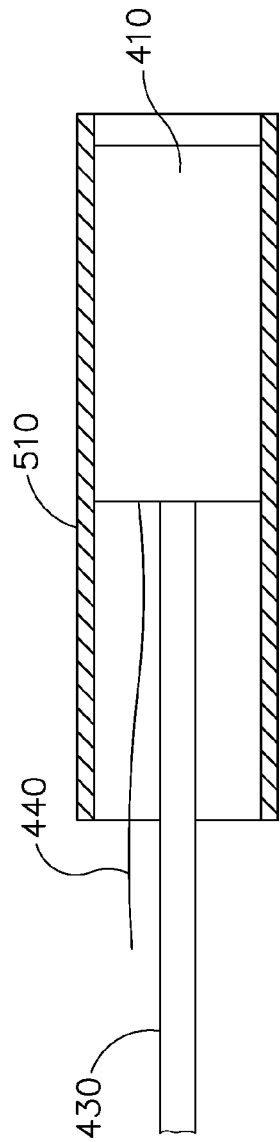
FIG. 14A depicts a cross sectional view of the suction device of FIG. 11 inserted within the outer sheath of FIG. 13.

In an exemplary use, suction device (400) is positioned within lumen (512) of outer sheath (510) with body (410) in the compressed state, as shown in FIG. 14A. The distal end of outer sheath (510) is then wetted such that fluid soaks body (410) of suction device (400). Outer sheath (510) and suction device (400) may also be submerged in fluid to wet body (410). Other suitable wetting methods will be apparent to one with ordinary skill in the art in view of the teachings herein. As body (410) soaks, pores of body (410) expand slightly to allow the volume of body (410) to wet. Body (410) is wetted until body (410) is damp, but not sodden, such that the fluid is constrained within body (410). Body (410) may be wetted with water, saline, or any other fluid that will be apparent to one with ordinary skill in the art in view of the teachings herein. Suction device (400) and outer sheath (510) may then be positioned in a patient's posterior choana or nasopharynx while irrigation catheter (80) is positioned at the irrigation site. Suction device (400) may be placed within the patient using outer sheath (510) as a handle such that no other instruments are needed. Suction device (400) is positioned such that body (410) is generally directed toward the patient's nasal cavity. In this example, suction tube (430) and string (440) exit through the patient's nostril. In some other versions, suction tube (430) and string (440) are oriented to exit through the patient's mouth.

Figure 14B:
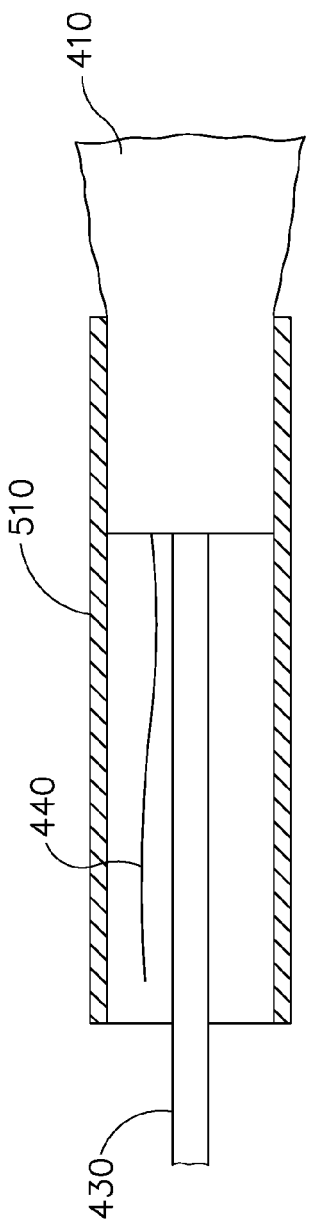
FIG. 14B depicts a cross sectional view of the suction device of FIG. 11 being advanced from the outer sheath of FIG. 13.
Figure 14C:
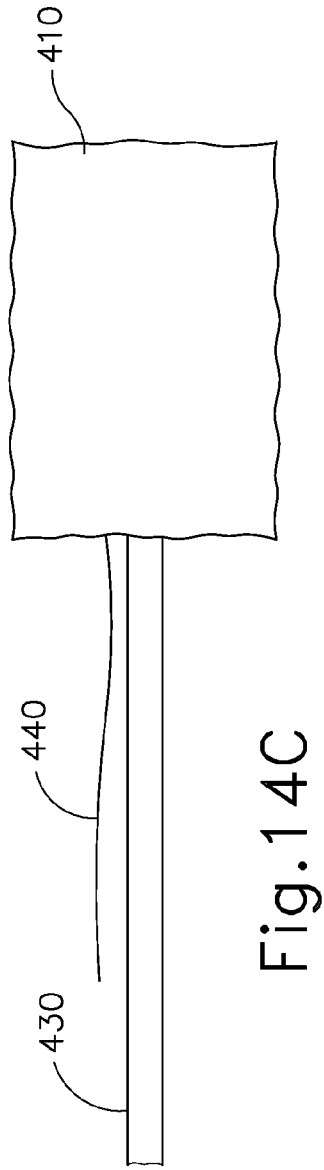
FIG. 14C depicts a side elevational view of the suction device of FIG. 11 removed from the outer sheath of FIG. 13.

Suction device (400) is then advanced through outer sheath (510), as shown in FIG. 14B. As device (400) is pushed out of outer sheath (510), body (410) expands to an expanded state. When device (400) is fully advanced from outer sheath (510), as shown in FIG. 14C, body (410) expands to press against the wall of the choana, thereby effectively sealing the choana. Body (410) may be pushed out of outer sheath (510) using a stylet, suction tube (430), or any other suitable device. Alternatively, outer sheath (510) may be retracted from device (400) while device (400) is held stationary. Outer sheath (510) may also be torn away from body (410) along a slit provided on outer sheath (510), allowing body (410) to expand. Other suitable methods to deploy device (400) from outer sheath (510) will be apparent to one with ordinary skill in the art in view of the teachings herein. In the present example, body (410) is configured to slide easily out of outer sheath (510) when body (410) is wet. If a physician attempts to place an expanded and/or wet suction device (400) in a patient's choana without using outer sheath (510), it may be difficult to enter the nasal cavity through a vestibule (e.g., nostril) and/or maneuver body (410) to the desired location. If a physician attempts to place a dry and compressed suction device (400) in a patient's choana without sheath (510), body (410) may need to soak in place to expand, which may allow fluid to drip down or flow into a patient's throat. Further, if body (410) is expanded with fluid through suction tube (430), body (410) may resist expansion, fill unevenly, or fill slowly with oversaturation. Thus, in the body (410) is pre-wetted in outer sheath (410) in the present example before device (400) is advanced through outer sheath (510) as shown in FIG. 14B. In some instances, additional fluid is then added to body (410) to expand body (410) further before irrigation begins.

Once body (410) is deployed from outer sheath (510), irrigation fluid is communicated through irrigation catheter (80) while suction is communicated to suction tube (430). The irrigation fluid drains through the patient's nasal cavity and into body (410), which absorbs the fluid. As body (410) absorbs the fluid, suction tube (430) draws the fluid out of body (410). This prevents body (410) from becoming oversaturated to the point where suction device (400) no longer effectively plugs the drainage path. Once sufficient irrigation has been provided, suction device (400) may be removed by pulling string (440) proximally to thereby pull body (410) and suction tube (430) proximally out of the nose or throat, depending on the orientation of string (440).

FIGS. 15-17 show another exemplary suction device (600) that may be used with outer sheath (510) to handle fluid drainage from an irrigation procedure performed using irrigation catheter (80) or using some other irrigation device. Suction device (600) of this example is substantially similar to suction device (400) in that suction device (600) comprises an absorbent body (610), a suction tube (630), and a string (640). However, absorbent body (610) of suction device (600) has an ovular profile and an angled proximal end. As best seen in FIG. 17, the ovular profile of body (610) has a top circular portion (616) and a bottom circular portion (618), connected by side portions (619). The generally ovular shape of body (610) may accommodate a generally ovular shape of an adult choana. An adult choana opening may define a height of about 21-33 mm, with an average height of 25 mm, and a width of about 10.5-19 mm, with an average width of 13.5 mm. The soft tissue of an adult choana opening may be about 2-3 mm thick. Accordingly, body (610) may have a height of 1.1+/−0.02 inches, a width of 0.65+/−0.02 inches, and a radius portion of 0.325 inches. In other versions, body (610) has a height of 0.85+/−0.02 inches, a width of 0.45+/−0.02 inches, and a radius portion of 0.225 inches. Of course, other suitable dimensions will be apparent to one with ordinary skill in the art in view of the teachings herein. It should also be understood that suction device (600) may have a circular profile or a profile of any other suitable shape.

FIG. 16 shows a proximal end of body (610). The proximal end of body (610) comprises a top angled portion (612) extending inwardly and proximally from top portion (616) and a bottom angled portion (614) extending inwardly and proximally from bottom portion (618). In the present example, top angled portion (612) and bottom angled portion (614) ramp inwardly toward each other to proximal face (616). Top angled portion (612) and bottom angled portion (614) may define an angle of 30 degrees, but other suitable angles will be apparent to one with ordinary skill in the art in view of the teachings herein. The angled proximal end of body (610) may slide through a nasal cavity in a cam-like fashion (i.e., gently camming against the wall of the nasal cavity and any adjacent paranasal anatomical structures, etc.) such that the angled proximal end of body (610) allows for easier removal of suction device (600) from a nasal cavity. In other versions, top angled portion (612) and bottom angled portion (614) ramp together to a point instead of a proximal face (616). In some other versions, side portions (619) comprise angled portions that ramp inward on the proximal end of body (610). As yet another merely illustrative example, the proximal end of body (610) may include an annular chamfer. Other suitable proximal end configurations of body (610) will be apparent to one with ordinary skill in the art in view of the teachings herein.

Body (610) of the present example further comprises a non-porous region (620) on the distal end of body (610), as shown in FIG. 15. Non-porous region (620) is configured to prevent fluid from passing through the distal end of body (610). For example, body (610) may be positioned within a choana such that non-porous region (620) prevents fluid from passing into a patient's throat. The distal end of body (610) may be sealed with a nonabsorbent coating to form non-porous region (620); or non-porous region (620) may include a base (120, 220, 320) as described above; or the pores of the same foam material may be closed from processing. Various suitable ways in which the pore configuration for the distal end of body (610) may be varied will be apparent to one with ordinary skill in the art in view of the teachings herein. Non-porous region (620) may be configured to completely prevent fluid from passing through the distal end of body (610). Alternatively, non-porous region (620) may restrict passage of fluid through the distal end of body (610) to a point where the fluid is slowed enough such that suction may remove the excess fluid from body (610) before the fluid passes fully through the distal end of body (610) and into the patient's throat. Other suitable non-porous region (620) configurations will be apparent to one with ordinary skill in the art in view of the teachings herein. In the present example, non-porous region (620) extends completely along the distal face of body (610) and 0.3 inches along the longitudinal length of the distal end of body (610). Alternatively, non-porous region (620) may be sized to cover any other suitable extent of body (610) as will be apparent to one with ordinary skill in the art in view of the teachings herein.

Suction device (600) operates similar to suction device (400). For instance, suction device (600) is positioned within lumen (512) of outer sheath (510) with body (610) in a compressed state. Body (610) is then wetted such that fluid soaks body (610) of suction device (600). As body (610) soaks, pores of body (610) expand slightly to allow the volume of body (610) to wet until body (610) is damp, but not sodden. Suction device (600) and outer sheath (510) may then be positioned in a patient's posterior choana or nasopharynx while irrigation catheter (80) is positioned at the irrigation site. Suction device (600) may be placed within the patient using outer sheath (510) as a handle such that no other instruments are needed. Suction device (600) is positioned such that non-porous region (620) of body (610) is generally directed toward the patient's nasal cavity. In this example, suction tube (630) and string (640) exit through the patient's nostril. In some other versions, suction tube (630) and string (640) are oriented to exit through the patient's mouth.

Suction device (600) is then advanced through outer sheath (510). As device (600) is pushed out of outer sheath (510), body (610) expands to an expanded state. When device (600) is fully advanced from outer sheath (510), body (610) is expanded to press against the wall of the choana, thereby effectively sealing the choana. Body (610) may be pushed out of outer sheath (510) using a stylet, suction tube (630), or any other suitable device. Alternatively, outer sheath (510) may be retracted from device (600) while device (600) is held stationary. Other suitable methods to deploy device (600) from outer sheath (510) will be apparent to one with ordinary skill in the art in view of the teachings herein. In some instances, additional fluid is then added to body (610) to expand body (610) further before irrigation begins.

Once body (610) is deployed from outer sheath (510), irrigation fluid is communicated through irrigation catheter (80) while suction is communicated to suction tube (630). The irrigation fluid drains through the patient's nasal cavity and into body (610), which absorbs the fluid. As body (610) absorbs the fluid, suction tube (630) draws the fluid out of body (610). This prevents body (610) from becoming oversaturated to the point where suction device (600) no longer effectively plugs the drainage path. Non-porous region (620) further prevents fluid from passing through body (610) to the patient's throat. Once sufficient irrigation has been provided, suction device (600) may be removed by pulling string (640) proximally to thereby pull body (610) and suction tube (630) proximally out of the nose or throat, depending on the orientation of string (640). The angled configuration of proximal end of body (610) facilitates proximal travel of body (610) through the nasal cavity to allow for easier removal of suction device (600).

B. Exemplary Nasal Suction Device with a Dedicated Deployment Instrument

FIG. 18 shows another exemplary suction device (700) that may be used to handle drainage from an irrigation procedure performed using irrigation catheter (80) or using some other irrigation device. Suction device (700) of this example is substantially similar to suction device (400) in that suction device (700) comprises an absorbent body (710) and a suction tube (730). Absorbent body (710) and suction tube (730) may be configured and operable similar to absorbent body (410) and suction tube (430) described above. In the present example, body (710) defines a generally circular cross-sectional profile. Of course, body (710) may define other suitable cross-sectional profile shapes as will be apparent to one with ordinary skill in the art in view of the teachings herein (e.g., ovular, square, rectangular, hexagonal, octagonal, etc.). The proximal end of body (710) is angled such that a top portion (712) and a bottom portion (714) of body (710) ramp inwardly to a proximal face (716). In some other versions, top angled portion (712) and bottom angled portion (714) ramp together to a point instead of a proximal face (716). The side portions of body (710) may also comprise angled portions that ramp inwardly on the proximal end of body (710). As yet another merely illustrative example, the proximal end of body (710) may include an annular chamfer. Other suitable proximal end configurations of body (710) will be apparent to one with ordinary skill in the art in view of the teachings herein.

FIG. 19 shows a deployment instrument (800) that may be used with suction device (700) to position body (710) within a desired anatomical passageway. Instrument (800) comprises a distal housing (830), coupled to a handle (810) by shaft portion (820). Housing (830) is sized to enclose body (710) of suction device (700) when body (710) is in the compressed state such that body (710) does not slip out of housing (830). Housing (830) may be configured to entirely enclose body (710) within housing (830), or housing (830) may partially enclose body (710) such that a portion of body (710) is exposed through housing (830). For example, the distal end of body (710) may partially extend out of housing (830) and/or side portions of body (710) may be exposed along the longitudinal length of housing (830). Other suitable methods to enclose body (710) within housing (830) will be apparent to one with ordinary skill in the art in view of the teachings herein. The exterior of housing (830) is configured to fit within a nasal cavity.

In the present example, distal housing (830) comprises a first housing (832) and a second housing (834). First housing (832) defines a semi-circular profile that is configured to enclose a top portion of body (710). Second housing (834) defines a semi-circular profile that corresponds to first housing (832) such that second housing (834) is configured to enclose a bottom portion of body (710). Although housing (830) has a generally circular cross-sectional profile, other suitable cross-sectional profile shapes for housing (830) will be apparent to one with ordinary skill in the art in view of the teachings herein (e.g., ovular, elliptical, etc.). While FIG. 19 shows first and second housings (832, 834) of approximately equal size such that first and second housings (832, 834) each wrap around about half of body (710), first or second housing (832, 834) may also be larger and/or smaller such that first or second housing (832, 834) wraps around a greater and/or lesser amount of body (710). First housing (832) is slidable relative to second housing (834) to thereby selectively expose body (710) from housing (830). The proximal ends of first and second housing (832, 834) comprise tapered portions (836, 838) that ramp inwardly, as shown in FIG. 19. Tapered portions (836, 838) may engage the nasal cavity in a cam-like fashion (i.e., gently camming against the wall of the nasal cavity and any adjacent paranasal anatomical structures, etc.) to ease the removal of instrument (800) from a nasal cavity. The proximal end of housing (830) further defines an opening (837) that is sized to accommodate suction tube (730) such that suction tube (730) may pass freely through opening (837). Opening (837) may be provided in first housing (832) and/or second housing (834). In versions where a string is provided to extend proximally from body (710), the string may also be positioned through opening (837).

Shaft portion (820) of instrument (800) comprises a first shaft (826) and a second shaft (825), as shown in FIG. 19. The distal end of first shaft (826) is coupled with the proximal end of first housing (832) and the distal end of second shaft (825) is coupled with the proximal end of second housing (834). First and second shafts (826, 825) extend proximally from housing (830) and are arranged parallel to each other. First and second shafts (826, 825) each include an obliquely angled bent portion (824, 823), forming a dogleg configuration. Accordingly, proximal portions (822, 821) of shafts (826, 825) are laterally offset from the longitudinal axis defined by housing (830), as shown in FIG. 19. Bent portions (824, 823) of shafts (826, 825) may thereby provide clearance for other devices (e.g., endoscope (60), irrigation catheter (80), etc.) within the paranasal cavity. However, it should be noted that bent portions (824, 823) of shafts (826, 825) are merely optional. For instance, shafts (826, 825) may be straight along their full length or may be curved along at least a portion of their lengths. Various suitable configurations for shafts (826, 825) will be apparent to those of ordinary skill in the art in view of the teachings herein. First shaft (826) is slidable relative to second shaft (825) to thereby translate first housing (832) relative to second housing (834). For instance, shafts (826, 825) may be coupled by a tongue and groove coupling that allows shafts (826, 825) to slide longitudinally relative to each other, while maintaining the lateral alignment of shafts (826, 825). Other suitable ways in which shafts (826, 825) may be coupled will be apparent to one with ordinary skill in the art in view of the teachings herein.

Proximal portions (822, 821) of shafts (826, 825) are coupled with handle (810), as shown in FIG. 19. Handle (810) comprises a pair of finger grips (812, 814). Proximal portion (822) of first shaft (826) is coupled to first grip (814) by coupling member (818). Proximal portion (821) of second shaft (825) is coupled to second grip (812) by coupling member (816). First grip (814) is translatable relative to second grip (812). Grips (814, 812) of handle (810) are configured to be grasped by a single hand. In the present example, grips (814, 812) include openings to allow a user to insert a thumb and/or fingers into the openings to actuate handle (810). First grip (814) is actuated to translate away from second grip (812) to thereby translate first shaft (826) and first housing (832) proximally. As first housing (832) translates proximally, body (710) is exposed from housing (830) to allow the expansion of body (710).

Figure 20C:
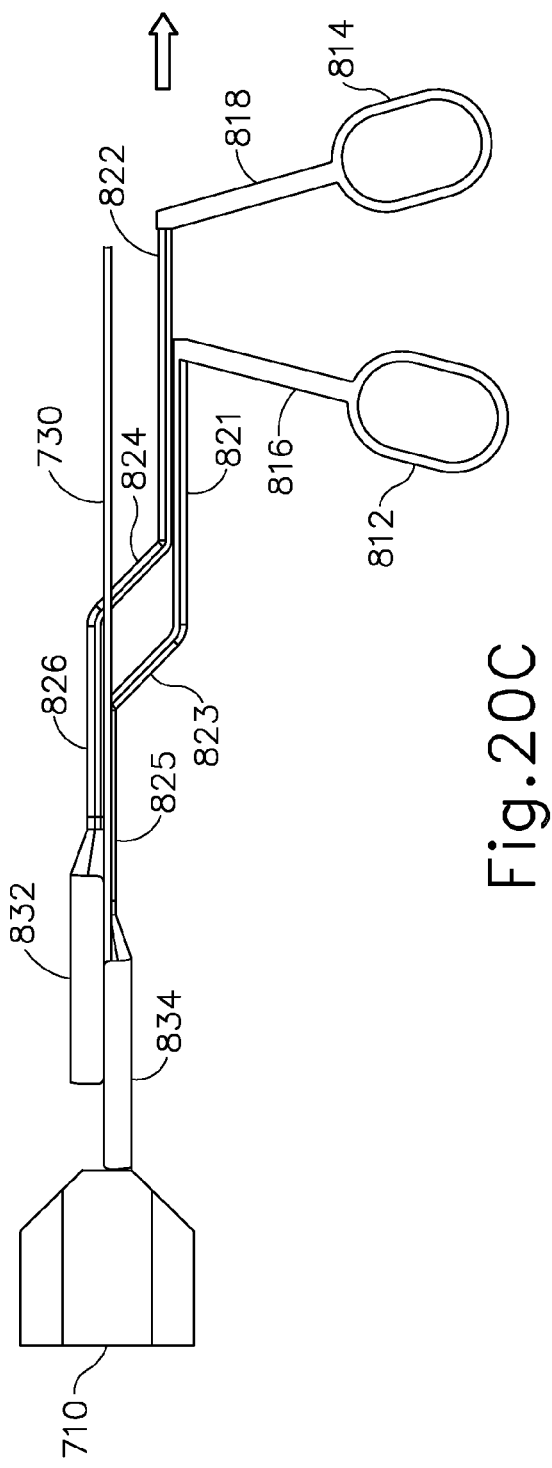
FIG. 20C depicts a side elevational view of the suction device of FIG. 18 deployed from the deployment instrument of FIG. 19.

FIGS. 20A-20D show an exemplary operation of suction device (700) and deployment instrument (800). As shown in FIG. 20A, suction device (700) is positioned within housing (830). Body (710) is enclosed by first and second housings (832, 834) with body (710) in a compressed state. Suction tube (730) is positioned within opening (837) of housing (830) to allow suction tube (730) to extend proximally outside of instrument (800). Body (710) is then wetted within housing (830) such that fluid soaks body (710) of suction device (700). As body (710) soaks, pores of body (710) expand slightly to allow the volume of body (710) to wet until body (710) is damp, but not sodden. Handle (810) of instrument (800) may then be used to maneuver housing (830) to place suction device (700) in a patient's posterior choana or nasopharynx while irrigation catheter (80) is positioned at the irrigation site. In this example, suction tube (730) exits through the patient's nostril. In some other versions, suction tube (730) is oriented to exit through the patient's mouth.

Figure 20D:
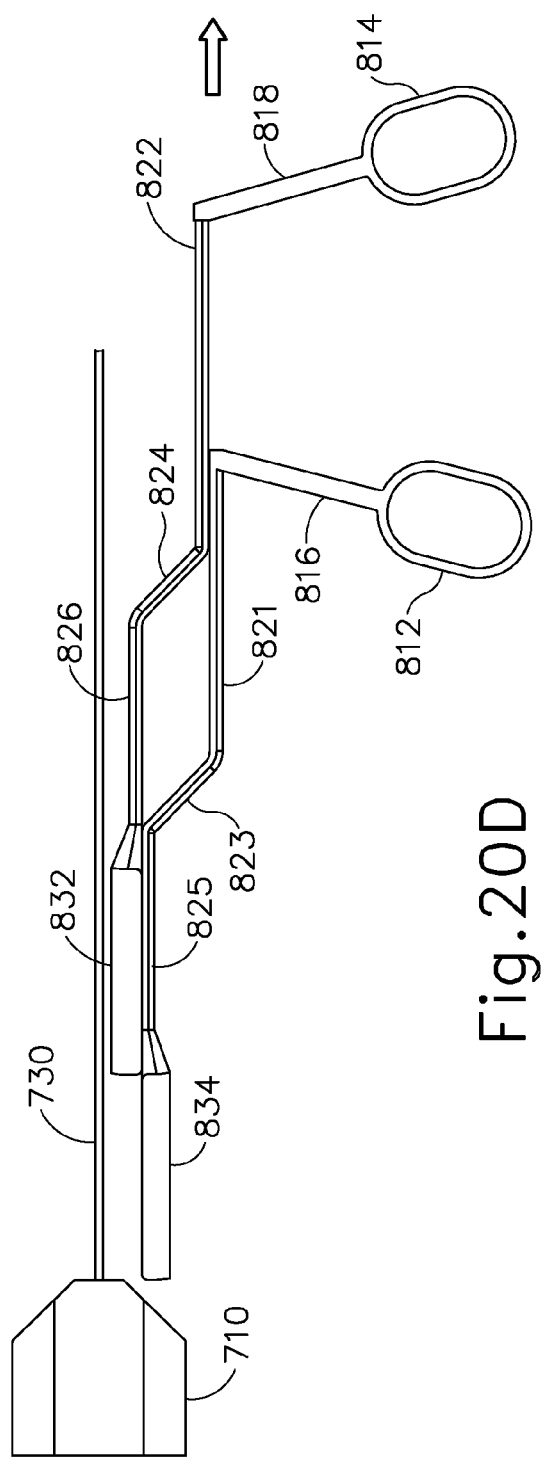
FIG. 20D depicts a side elevational view of the deployment instrument of FIG. 19 being removed from the suction device of FIG. 18.
Figure 21:
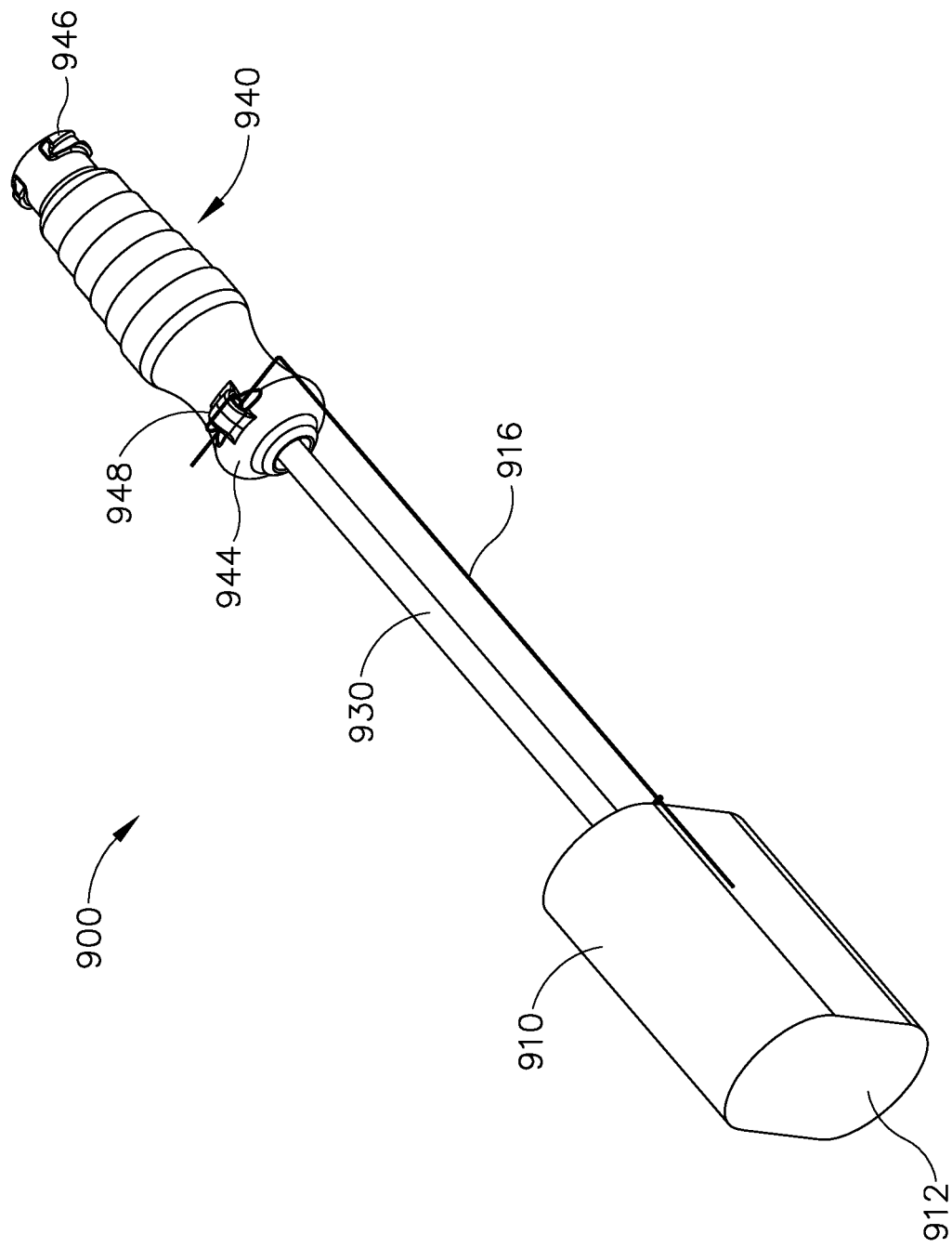
FIG. 21 depicts a perspective view of yet another exemplary suction device that may be used with the irrigation catheter of FIG. 6.
Figure 22:
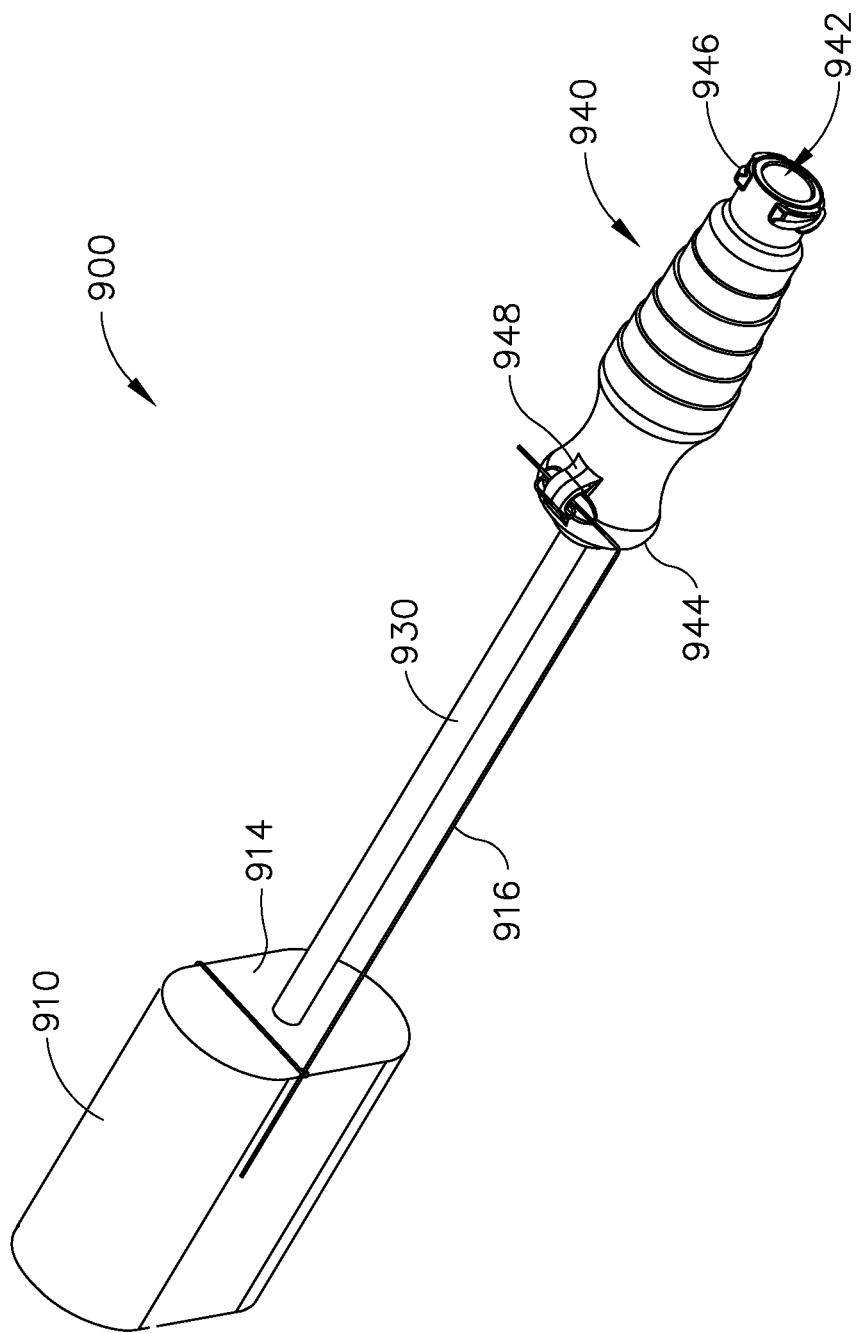
FIG. 22 depicts another perspective view of the suction device of FIG. 21.
Figure 23:
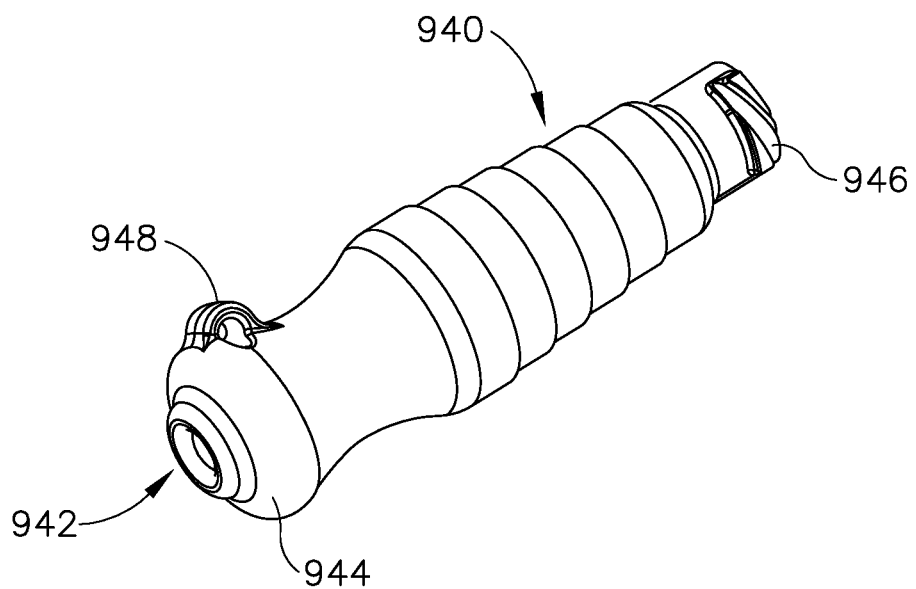
FIG. 23 depicts a perspective view of a connector of the suction device of FIG. 21.
Figure 24:
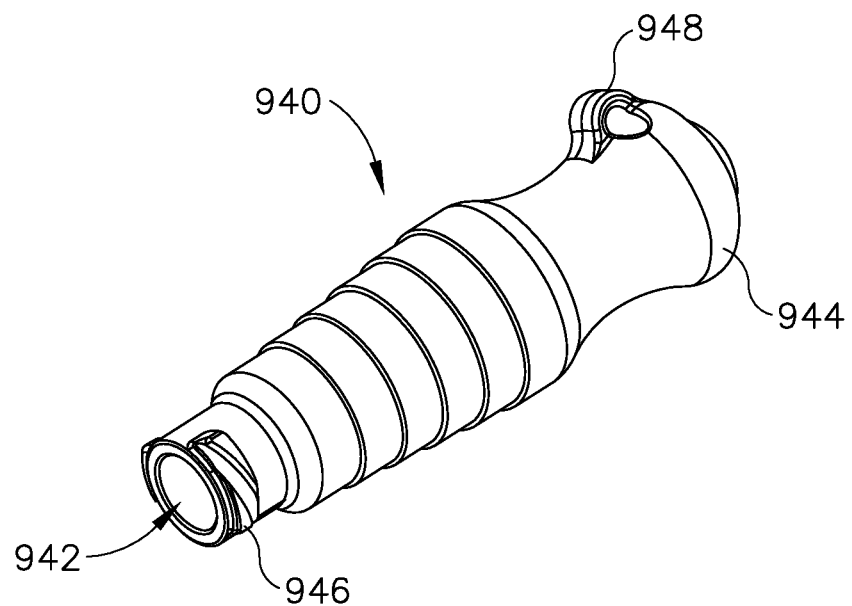
FIG. 24 depicts another perspective view of the connector of FIG. 23.

Suction device (700) is then exposed from housing (830), as shown in FIG. 20B. First grip (814) is translated proximally away from second grip (812). As first grip (814) translates proximally, first shaft (826) and first housing (832) thereby translate proximally. Accordingly, first housing (832) is translated relative to second housing (834) to expose a portion of body (710) of suction device (700). As device (700) is exposed from housing (830), body (710) expands to an expanded state. When device (700) is fully exposed from housing (830), as shown in FIG. 20C, body (710) selfexpands to press against the wall of the choana, thereby effectively sealing the choana. Deployment instrument (800) may then be pulled proximally to remove instrument (800) from device (700) and the nasal cavity, as shown in FIG. 20D. In some instances, additional fluid is then added to body (710) to expand body (710) further before irrigation begins.

Once body (710) is deployed from instrument (800), irrigation fluid is communicated through irrigation catheter (80) while suction is communicated to suction tube (730). The irrigation fluid drains through the patient's nasal cavity and into body (710), which absorbs the fluid. As body (710) absorbs the fluid, suction tube (730) draws the fluid out of body (710). This prevents body (710) from becoming oversaturated to the point where suction device (700) no longer effectively plugs the drainage path. Once sufficient irrigation has been provided, suction device (700) may be removed by pulling device (700) proximally out of the nose or throat. The angled configuration of proximal end of body (710) facilitates proximal travel of body (710) through the nasal cavity to allow for easier removal of suction device (700).

VI. Exemplary Nasal Suction Device with a Multi-Function Connector

FIGS. 21-26E show another exemplary suction device (900) that may be used to handle drainage from an irrigation procedure performed using irrigation catheter (80) or using some other irrigation device. Suction device (900) of this example comprises an absorbent body (910), a suction tube (930), and a connector (940). By way of example only, absorbent body (910) and suction tube (930) may be configured and operable in accordance with any of the teachings herein relating to absorbent body (110, 210, 310, 410, 610, 710) and suction tube (130, 230, 330, 430, 630, 730), respectively. In some versions, the distal end of suction tube (930) is disposed in body (910) and includes one or more suction openings that are also disposed in body (910). By way of example only, suction tube (930) may comprise a pebax material and/or any other suitable material(s). It should also be understood that at least a portion of suction tube (930) (e.g., a proximal portion of suction tube (930)) may include a strain relief feature, such as a strain relief sleeve, etc. For instance, a proximal region of suction tube (930) extending to connector (940) may include a strain relief overtube that is fitted about the outer surface of suction tube (930). In some such versions, the strain relief overtube has a length of approximately 2.0 inches, an inner diameter of approximately 0.095 inches and an outer diameter of approximately 0.115 inches; while suction tube (930) has a length of approximately 9.0 inches, an inner diameter of approximately 0.070 inches and an outer diameter of approximately 0.090 inches. Other suitable dimensions will be apparent to those of ordinary skill in the art in view of the teachings herein. Similarly, other suitable ways in which suction tube (930) may be provided with strain relief will be apparent to those of ordinary skill in the art in view of the teachings herein.

In the present example, body (910) defines a generally ovular cross-sectional profile. Of course, body (910) may define other suitable cross-sectional profile shapes as will be apparent to one with ordinary skill in the art in view of the teachings herein (e.g., circular, square, rectangular, hexagonal, octagonal, etc.). In some instances, the distal face (912) and/or proximal face (914) of body (910) includes a semi-permeable skin that slows (but does not prevent) the communication of fluid into and out of body (910). In some other variations, distal face (912) includes an impermeable skin while proximal face (914) includes a semi-permeable skin. Other suitable ways in which body (910) may include one or more impermeable skins and/or one or more semi-permeable skins will be apparent to those of ordinary skill in the art in view of the teachings herein.

Body (910) may be provided in any number of sizes. For instance, different suction devices (900) may be provided to make different body (910) sizes available. By way of example only, a small body (910) size may be approximately 1.0 inches long and approximately 0.50 inches wide when expanded; and approximately 0.28 inches long and approximately 0.14 inches wide when compressed. As another merely illustrative example, a large body (910) size may be approximately 1.25 inches long and approximately 0.65 inches wide when expanded; and approximately 0.32 inches long and approximately 0.16 inches wide when compressed. In some versions where body (910) has an ovular profile, body (910) may be approximately 1.0 inches long, approximately 0.50 inches wide, and approximately 0.95 inches tall when expanded; and approximately 0.16 inches wide and approximately 0.32 inches tall when compressed. Other suitable sizes will be apparent to those of ordinary skill in the art in view of the teachings herein. In some versions where the distal end of body (910) includes a radiused corner, the corner may be curved at a radius of approximately 0.08 inches when compressed. Similarly, other suitable features, configurations, and structural characteristics that may be incorporated into body (910) will be apparent to those of ordinary skill in the art in view of the teachings herein.

Figure 25:
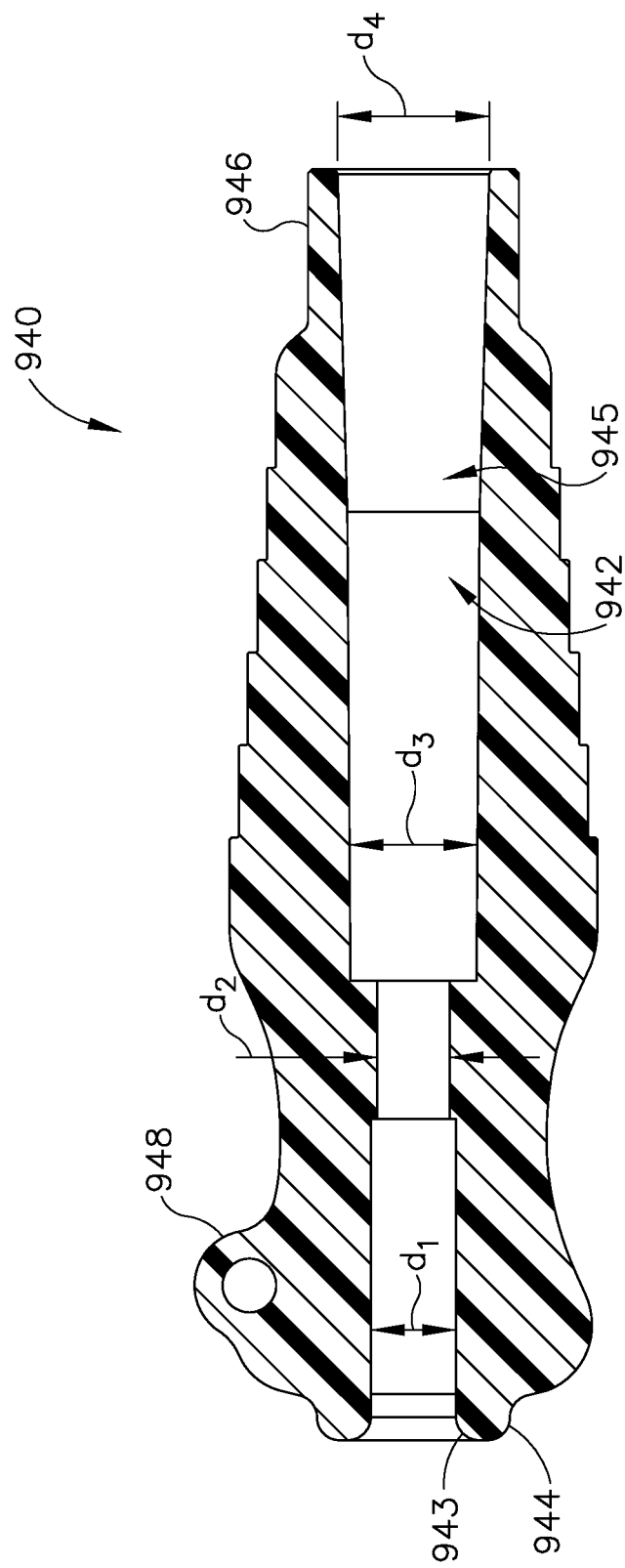
FIG. 25 depicts a side cross-sectional view of the connector of FIG. 23.

Connector (940) of the present example is contoured to promote gripping of connector (940) by an operator, between the operator's thumb and index finger. As best seen in FIGS. 22-25, connector (940) of the present example defines a lumen (942), which is in fluid communication with suction tube (930). As seen in FIG. 25, the distal end of lumen (942) provides a curved transition (943) to the exterior of the distal end (944) of connector (940). As also best seen in FIG. 25, the diameter of lumen (942) varies along the length of lumen (942). In particular, a distal region of lumen (942) has a first diameter ($d_1$); an intermediate region of lumen (942) has a second diameter ($d_2$); and a proximal region of lumen (942) ranges from a third diameter ($d_3$) to a fourth diameter ($d_4$). By way of example only, first diameter ($d_1$) may be between approximately 0.93 inches and approximately 0.090 inches; second diameter ($d_2$) may be approximately 0.079 inches; third diameter ($d_3$) may be approximately 0.143 inches; and fourth diameter ($d_4$) may be approximately 0.169 inches. Of course, any other suitable diameter sizes may be used. In the present example, the proximal end of lumen (942) provides a tapered transition from the third diameter ($d_3$) to the fourth diameter ($d_4$), at an angle of approximately 3.43 degrees. Of course, any other suitable angle may be used. Furthermore, the transition from the third diameter ($d_3$) to the fourth diameter ($d_4$) may be stepped, curved, or have some other configuration. It should also be understood that the third diameter ($d_3$) may extend consistently along a certain length of lumen (942), such that the taper toward the fourth diameter ($d_4$) begins at a transition region (945) in lumen (942) as shown in FIG. 25.

It should be understood that various kinds of conventional tubing may be coupled with connector (940). By way of example only, conventional tubing may be deformably fitted over distal end (944), such that the tubing deforms to receive distal end (944) and thereby provide a fluid tight fit with lumen (942). In addition or in the alternative, conventional tubing may be deformably fitted over proximal end (946), such that the tubing deforms to receive proximal end (946)

and thereby provide a fluid tight fit with lumen (942). It should also be understood that conventional tubing may be deformably fitted into lumen (942). For instance, the distal and/or proximal end of lumen (942) may receive conventional tubing that has an outer diameter that is greater than the corresponding diameter ($d_1$, $d_4$) of lumen (942), such that the tubing deforms to pass into lumen (942) and thereby provide a fluid tight fit with lumen (942). One or more regions of lumen (942) may include barbs and/or other features that are configured to retain a tube inserted in lumen (942). Other suitable features, dimensions, and configurations that may be provided in lumen (942) will be apparent to those of ordinary skill in the art in view of the teachings herein.

In the present example, the distal end (944) of connector (940) is fixedly secured to suction tube (930). The proximal end (946) of connector (940) comprises a luer fitting feature, which enables connector (940) to be coupled with a complementary luer fitting of some other device as will be described in greater detail below. By way of example only, proximal end (946) of connector (940) may include two separate luer threads on opposite lateral sides of connector (940). As another merely illustrative example, proximal end (946) of connector (940) may include a single, full luer thread extending about the full circumference of proximal end (946). As yet another merely illustrative example, proximal end (946) of connector (940) may include a slip fit or snap fit feature that is configured to couple with a luer fitting of a separate device. Various suitable ways in which proximal end (946) may be configured will be apparent to those of ordinary skill in the art in view of the teachings herein.

Connector (940) of the present example also includes an integral loop (948). A string (916) is secured to loop (948) and also to body (910), such that string (916) provides a tether between connector (940) and body (910). It should therefore be understood that, similar to strings (440, 640) described above, string (916) may be grasped and pulled to thereby pull suction device (900) out of a patient through the nasal cavity or through the patient's mouth (depending on the orientation string (916) within the patient's choana (C) or the nasopharynx (NP), etc.). String (916) may also reduce the risk of inadvertent aspiration of body (910) in the event that body (910) breaks free from suction tube (930) due to operator misuse. In some versions, string (916) wraps around the proximal end of body (910) and passes transversely through body (910) at approximately 0.25 inches from the proximal end of body (910), thereby forming a loop to secure string (916) to body (910). Various suitable ways in which string (916) may be coupled with body (910) will be apparent to those of ordinary skill in the art in view of the teachings herein. It should also be understood that string (916) is merely optional.

Figure 26B:
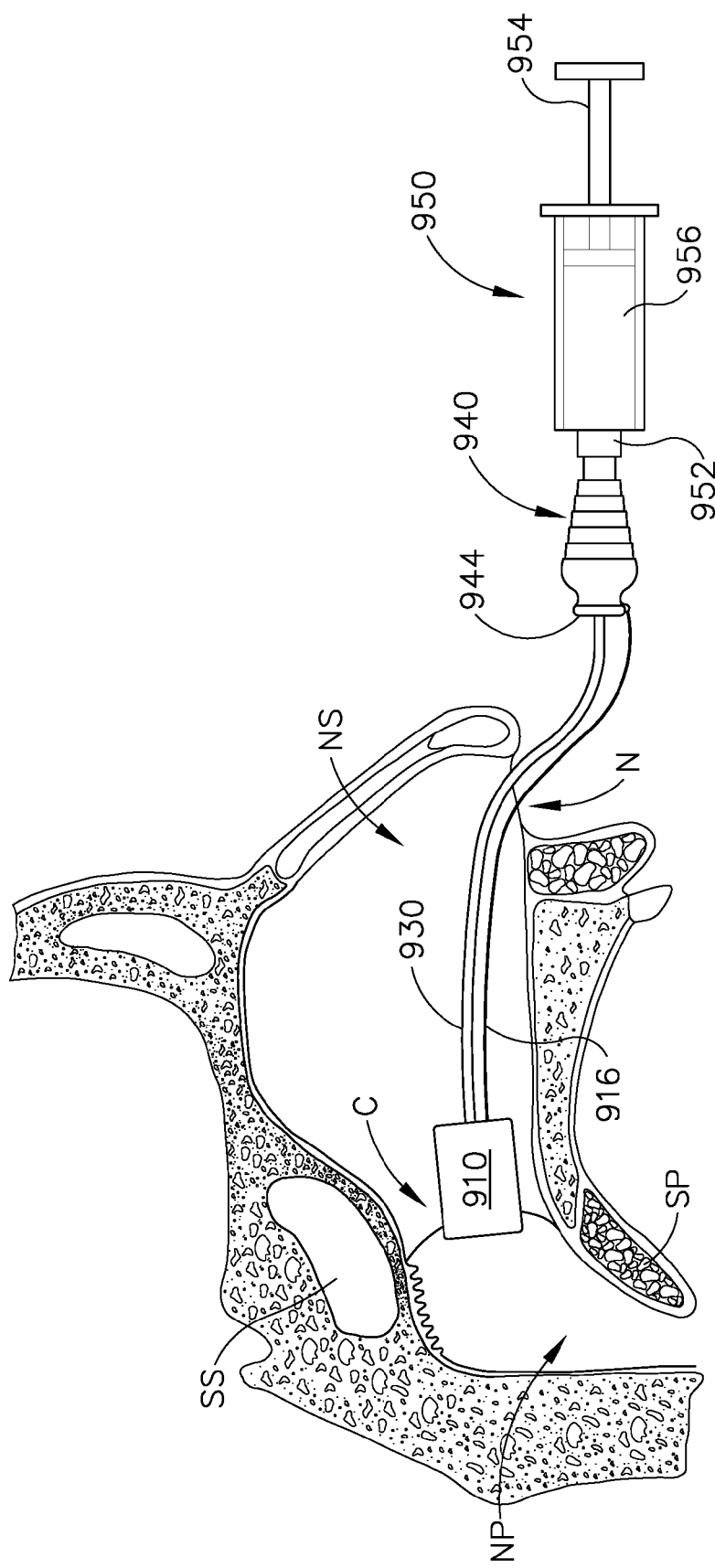
FIG. 26B depicts a diagrammatic view of the suction device of FIG. 21 in a compressed state, positioned within a patient's choana, and coupled with a fluid filled syringe.

FIGS. 26A-26E depict various exemplary steps that may be carried out to deploy suction device (900) for use during an irrigation procedure where irrigation catheter (80) is used. FIG. 26A depicts suction device (900) positioned such that body (910) is located in a patient's choana (C). Body (910) is in a compressed state. It should be understood that, with body (910) in the compressed state (910), body (910) may be inserted through the patient's nostril (N) to reach the choana (C). It should also be understood that any of the instrumentation described herein may be used to position body (910) in the choana (C) as shown in FIG. 26A. By way of example only, the operator may use regular forceps, bayonet forceps, sheath (510), deployment instrument (800), and/or any other suitable kind of instrument as will be apparent to those of ordinary skill in the art in view of the teachings herein. As noted above, body (910) may include tapered or rounded edges to promote smooth insertion of body (910) to reach the choana (C). In addition or in the alternative, at least a portion of body (910) may be coated with a lubricant (e.g., K-Y® Jelly by McNeil PPC, Inc. of Fort Washington, Pa.) to promote smooth insertion of body (910) to reach the choana (C). While body (910) is shown as being positioned in the choana (C), it should be understood that body (910) may be positioned in the nasopharynx (NP) in addition to or in lieu of being positioned in the choana (C). Alternatively, body (910) may be positioned in some other anatomical passageway. Indeed, it is contemplated that suction device (900) may be used in various other locations and in various other procedures, not just procedures involving paranasal sinus irrigation.

Figure 26C:
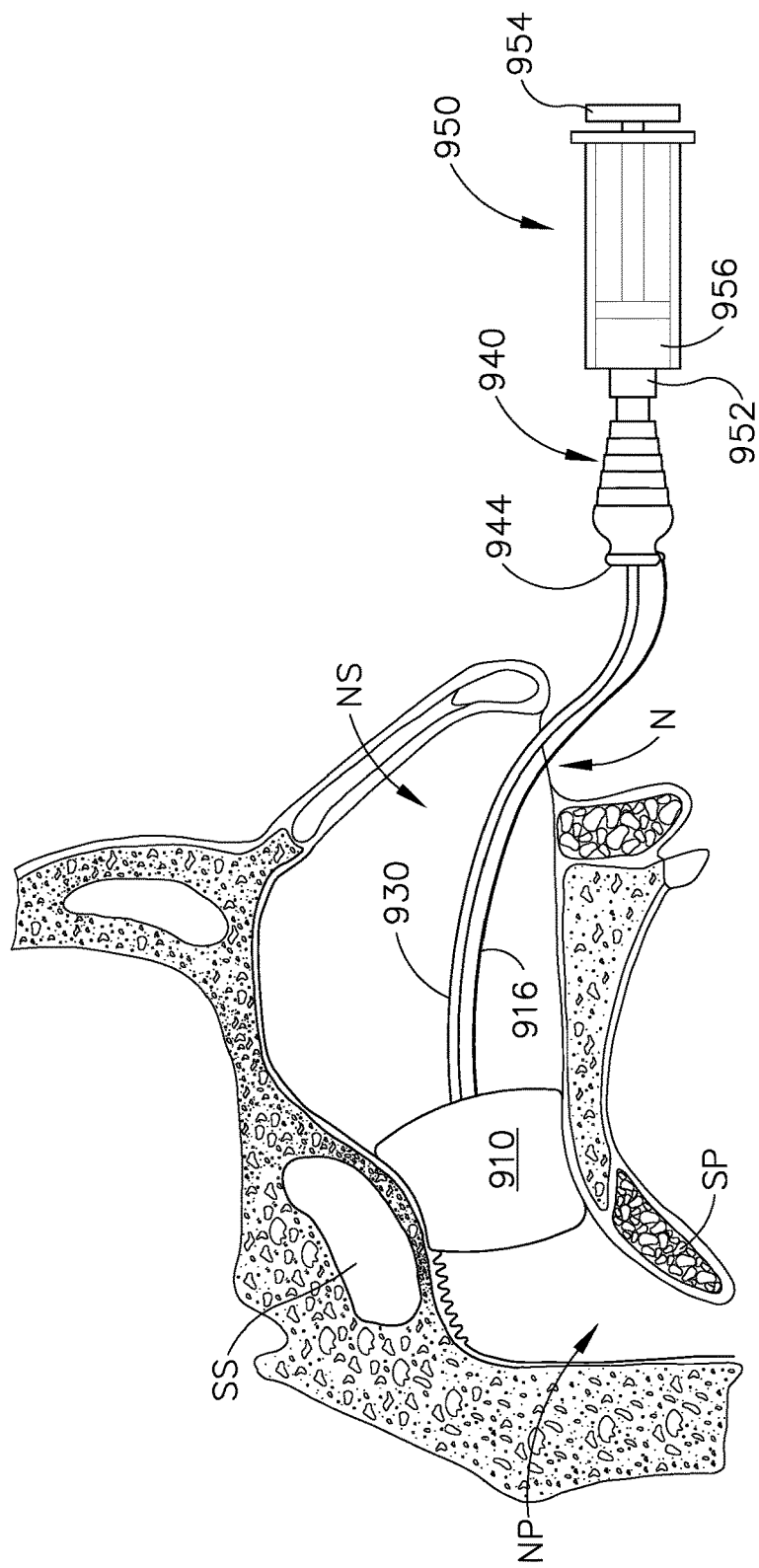
FIG. 26C depicts a diagrammatic view of the suction device of FIG. 21 in an expanded state, positioned within a patient's choana, having received fluid from a syringe.

Once body (910) has been suitably positioned in the region of the choana (C), connector (940) is then coupled with a conventional, fluid filled syringe (950), as shown in FIG. 26B. In particular, the distal luer fitting (952) of syringe (950) is coupled with the luer fitting at proximal end (946) of connector (940), providing a fluid tight coupling. Once distal luer fitting (952) of syringe (950) is coupled with the luer fitting at proximal end (946) of connector (940), the operator advances the plunger (954) of syringe (950) to drive fluid (e.g., saline, etc.) from the body (956) of syringe (950), as shown in FIG. 26C. This fluid travels through lumen (942) of connector (940), then further through suction tube (930) to reach body (910). As body (910) receives the fluid, body (910) swells such that body (910) eventually fills the region of the choana (C) as shown in FIG. 26C. By way of example only, the operator may use syringe (950) to inject approximately 5 cc of fluid into body (910) in order to transition body (910) from the compressed state (FIG. 26B) to the expanded state (FIG. 26C). Alternatively, any other suitable volume of fluid may be used. With body (910) in the expanded state, body (910) bears against the walls of the paranasal cavity in the region of the choana (C).

Figure 26D:
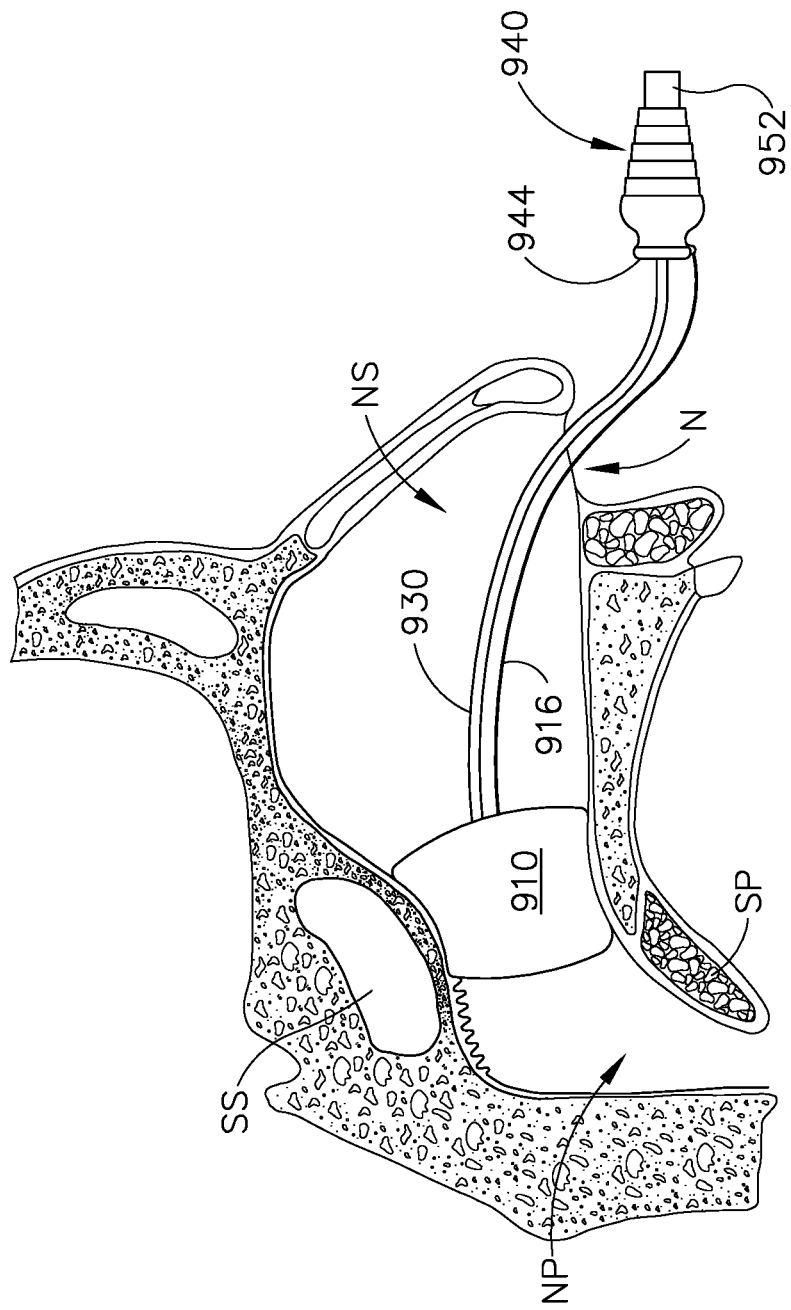
FIG. 26D depicts a diagrammatic view of the suction device of FIG. 21 in an expanded state, positioned within a patient's choana, decoupled from a syringe.
Figure 26E:
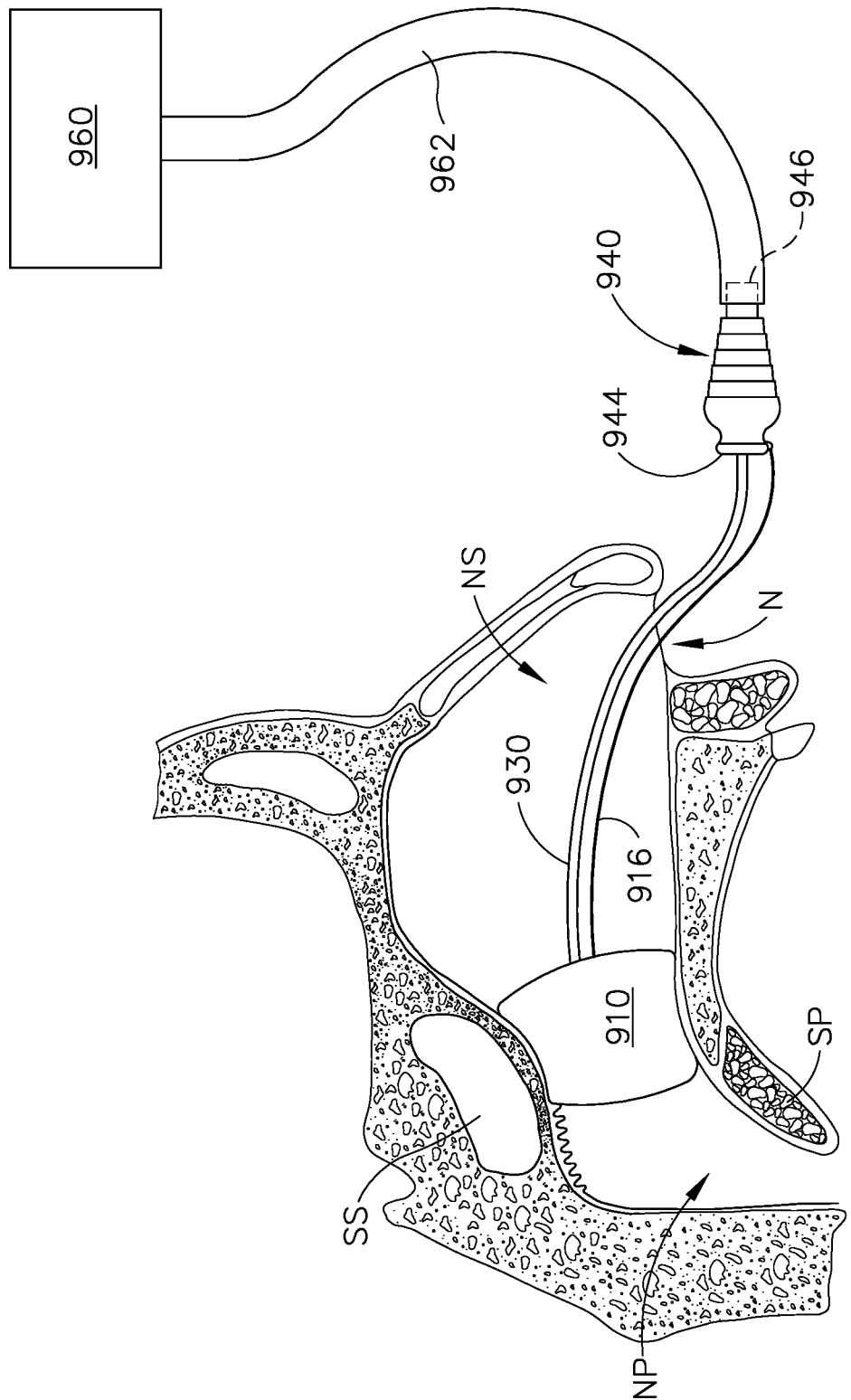
FIG. 26E depicts a diagrammatic view of the suction device of FIG. 21 in an expanded state, positioned within a patient's choana, coupled with a suction source.
Figure 27:
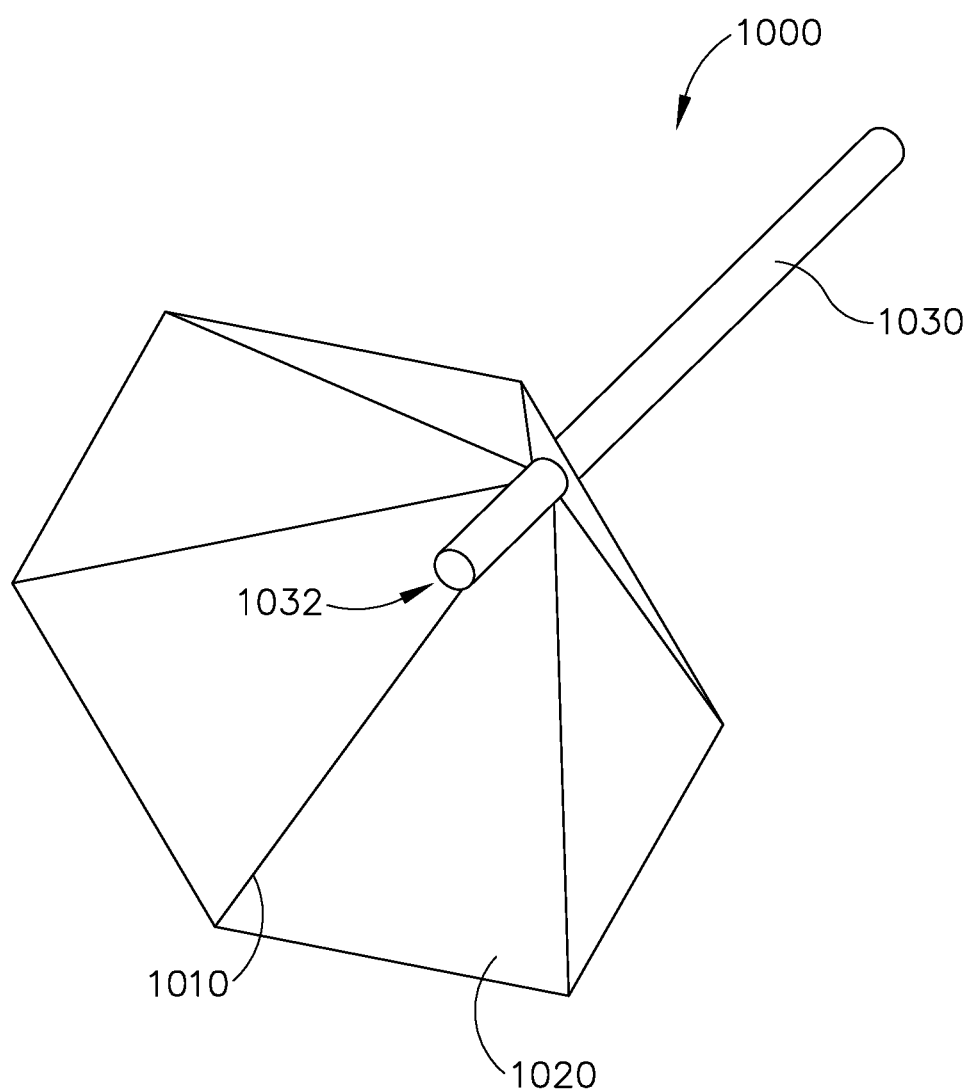
FIG. 27 depicts a perspective view of yet another exemplary suction device that may be used with the irrigation catheter of FIG. 6.

Once body (910) has been expanded within the choana (C), syringe (950) is removed from connector (940) as shown in FIG. 26D. Next, a suction source (960) is coupled with connector (940) via a tube (962), as shown in FIG. 26E. In particular, tube (962) is positioned over proximal end (946) of connector (940), providing a fluid tight fit. In some instances, the end of tube (962) deforms to fit over proximal end (946) of connector (940). In some other instances, the end of tube (962) includes a luer feature that complements the luer feature at proximal end (946) of connector (940). In still other instances, the end of tube (962) is deformably inserted within lumen (942) at proximal end (946) of connector (940). Alternatively, tube (962) may be coupled with connector (940) in any other suitable fashion. Suction source (960) may take a variety of forms, including but not limited to a vacuum pump, vacuum wall outlet, syringe, etc. After suction source (960) is coupled with connector (940), suction source (960) may provide suction to body (910) via lumen (942) of connector (940) and suction tube (930). The operator may thus initiate an irrigation procedure (using irrigation catheter (80) or using some other irrigation device) after reaching the stage shown in FIG. 26E, and suction device (900) will cooperate with suction source (960) to prevent the irrigation fluid from reaching the patient's throat. In other words, suction device (900) and suction source (960) may cooperate to absorb and draw away irrigation fluid during the irrigation procedure.

Once the irrigation procedure is complete, suction device (900) may be removed through the patient's nostril (N). In some instances, this may include pulling on suction tube (930) to remove body (910) from the choana (C). In addition or in the alternative, the operator may pull string (916) to remove body (910) from the choana (C). Other suitable ways in which suction device (900) may be used will be apparent to those of ordinary skill in the art in view of the teachings herein.

VII. Exemplary Nasal Suction Device with Expandable Frame

FIGS. 27-30 show another exemplary suction device (1000) that may be used to handle drainage from an irrigation procedure performed using irrigation catheter (80) or using some other irrigation device. Suction device (1000) of this example comprises a set of frame members (1010) that are joined together by webbing (1020). Frame members (1010) converge at a suction tube (1030) and are secured to suction tube (1030). Frame members (1010) extend distally and obliquely relative to suction tube (1030). Suction tube (1030) includes an open distal end (1032) that is located in an interior region of suction device (1000) defined by webbing (1020). The other end (not shown) of suction tube (1030) may be coupled with a conventional source of suction as described elsewhere herein. It should therefore be understood that open distal end (1032) of suction tube (1030) may be used to suction fluid captured within the interior region of suction device (1000) defined by webbing (1020).

Figure 29A:
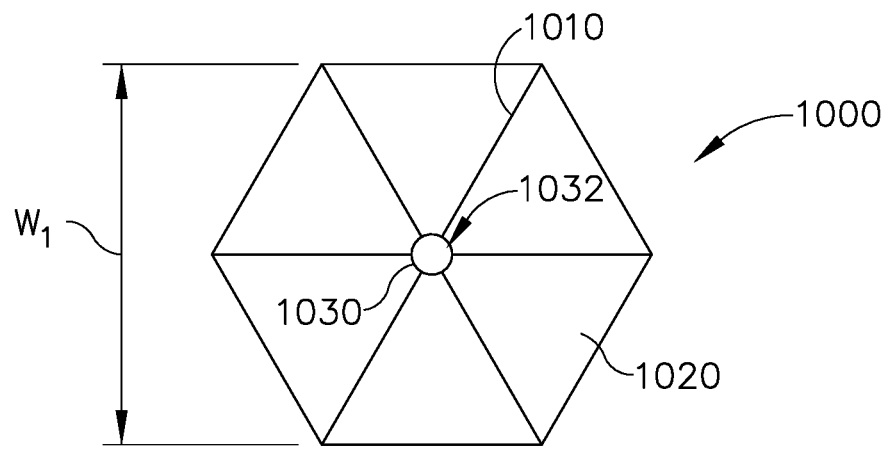
FIG. 29A depicts an end view of the suction device of FIG. 27 in a compressed state.
Figure 29B:
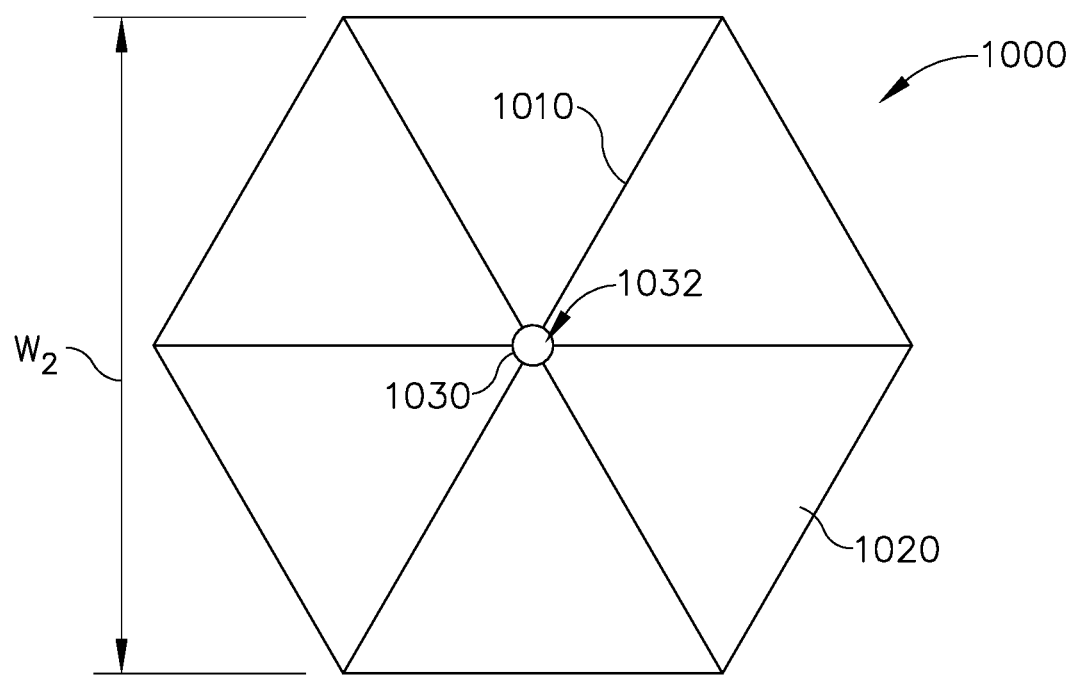
FIG. 29B depicts an end view of the suction device of FIG. 27 in an expanded state.

Frame members (1010) are configured to transition between a compressed configuration, as shown in FIGS. 28A and 29A; and an expanded configuration, as shown in FIGS. 28B and 29B. Webbing (1020) is configured to accommodate this expansion and compression of frame members (1010). When frame members (1010) and webbing (1020) are in the compressed configuration, frame members (1010) and webbing (1020) define a first effective width ($w_1$). When frame members (1010) and webbing (1020) are in the expanded configuration, frame members (1010) and webbing (1020) define a second effective width ($w_2$). The first effective width ($w_1$) is sized to permit suction device (1000) to be moved into position in the region of the patient's choana (C); while the second effective width ($w_2$) is sized to permit frame members (1010) and webbing (1020) to seal against (e.g., bear against) the paranasal walls at the region of the choana (C), as described in greater detail below.

In some versions, frame members (1010) are resiliently biased to assume the expanded configuration (FIGS. 28B and 29B), such that frame members (1010) must be held in compression to maintain the compressed configuration (FIGS. 28A and 29A). By way of example only, an outer sheath and/or other deployment instrument may be operable to hold resilient frame members (1010) in compression, then selectively release frame members (1010) to allow frame members (1010) to assume the expanded configuration when suction device (1000) has been suitably positioned. In some other versions, frame members (1010) are malleable. By way of example only, an inflatable balloon or other feature may be expanded to convert frame members (1010) from the compressed configuration to the expanded configuration. In still other versions, a push rod, linkages, and/or other mechanical features may be used to actuate frame members (1010), to thereby mechanically drive frame members (1010) from the compressed configuration to the expanded configuration (e.g., similar to an umbrella, etc.). Various suitable ways in which frame members (1010) may be selectively transitioned from the compressed configuration to the expanded configuration will be apparent to those of ordinary skill in the art in view of the teachings herein. It should also be understood that various kinds of materials and combinations of materials may be used to form frame members (1010), including but not limited to stainless steel, nitinol, etc.

Webbing (1020) may also be formed of a variety of materials. By way of example only, webbing (1020) may comprise a PVA foam, an absorbent fabric material, a hydrophilic coating, and/or various other kinds of materials. In some versions, webbing (1020) is resilient. In some other versions, webbing (1020) is flexible yet non-resilient. Other suitable materials and properties that may be incorporated into webbing (1020) will be apparent to those of ordinary skill in the art in view of the teachings herein.

Figure 30:
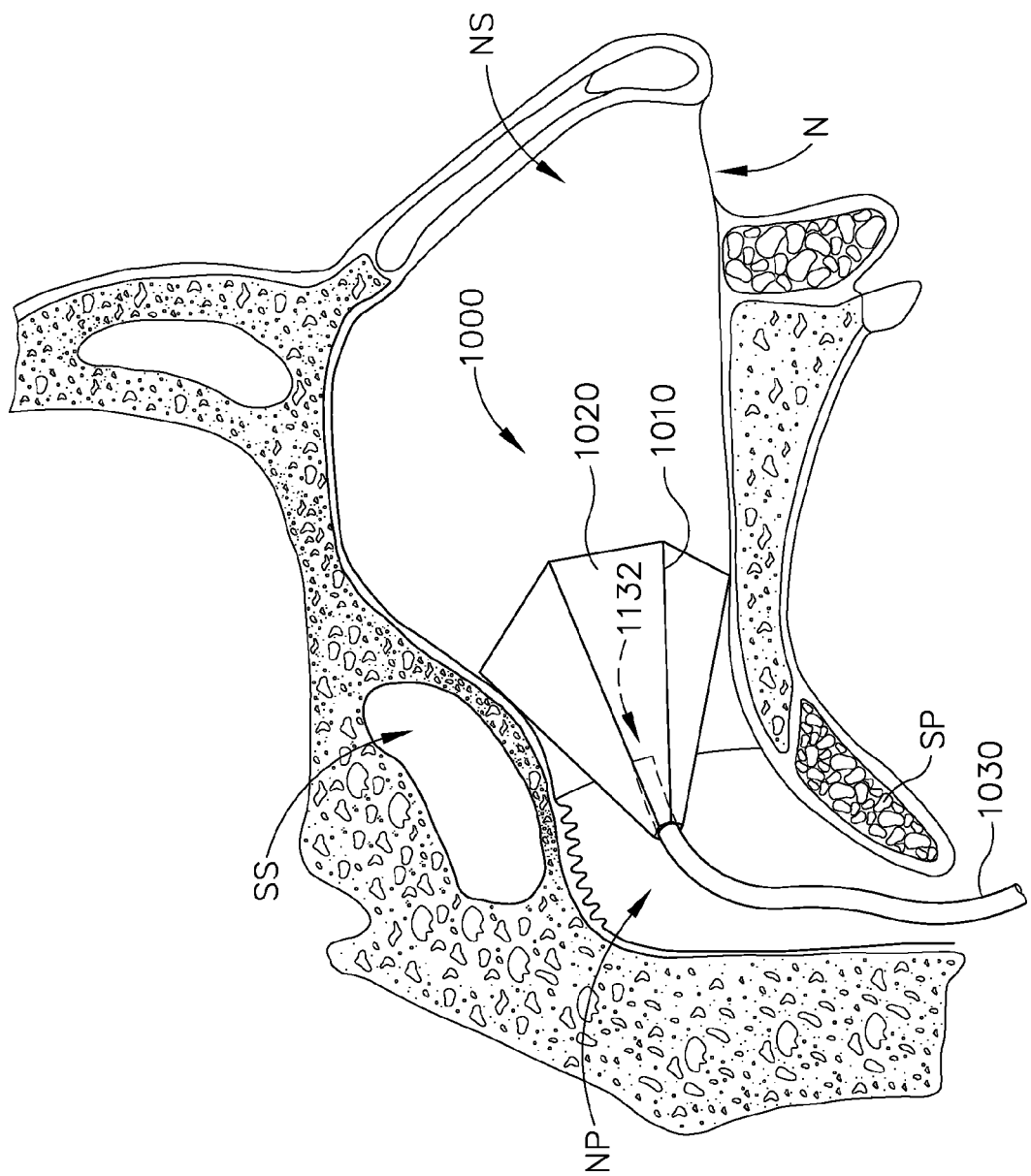
FIG. 30 depicts a diagrammatic view of the suction device of FIG. 27 disposed in a choana of a patient.

FIG. 30 shows one merely illustrative example of how suction device (1000) may be positioned within a choana (C). In this particular example, suction tube (1030) passes down through the nasopharynx (NP) and exits through the patient's mouth to reach a suction source (not shown). Frame members (1010) and webbing (1020) are in the expanded configuration to catch irrigation fluid, acting as a dam to prevent the irrigation fluid from reaching the nasopharynx (NP). The open distal end (1032) of suction tube (1030) draws in fluid that is caught by webbing (1020). It should be understood that suction device (1000) may be held in the compressed state by a sheath or other instrument feature before reaching the position shown in FIG. 30. Upon reaching the position shown in FIG. 30, suction device (1000) may be released and allowed to expand (or driven to expand) to the expanded configuration shown in FIG. 30. After the irrigation procedure is complete, a sheath or other instrument feature may be used to transition suction device (1000) back to the compressed configuration. Once in the compressed configuration, suction device (1000) may be withdrawn from the patient via the nasopharynx (NP) and mouth. Other suitable ways in which suction device (1000) may be used will be apparent to those of ordinary skill in the art in view of the teachings herein.

Figure 31:
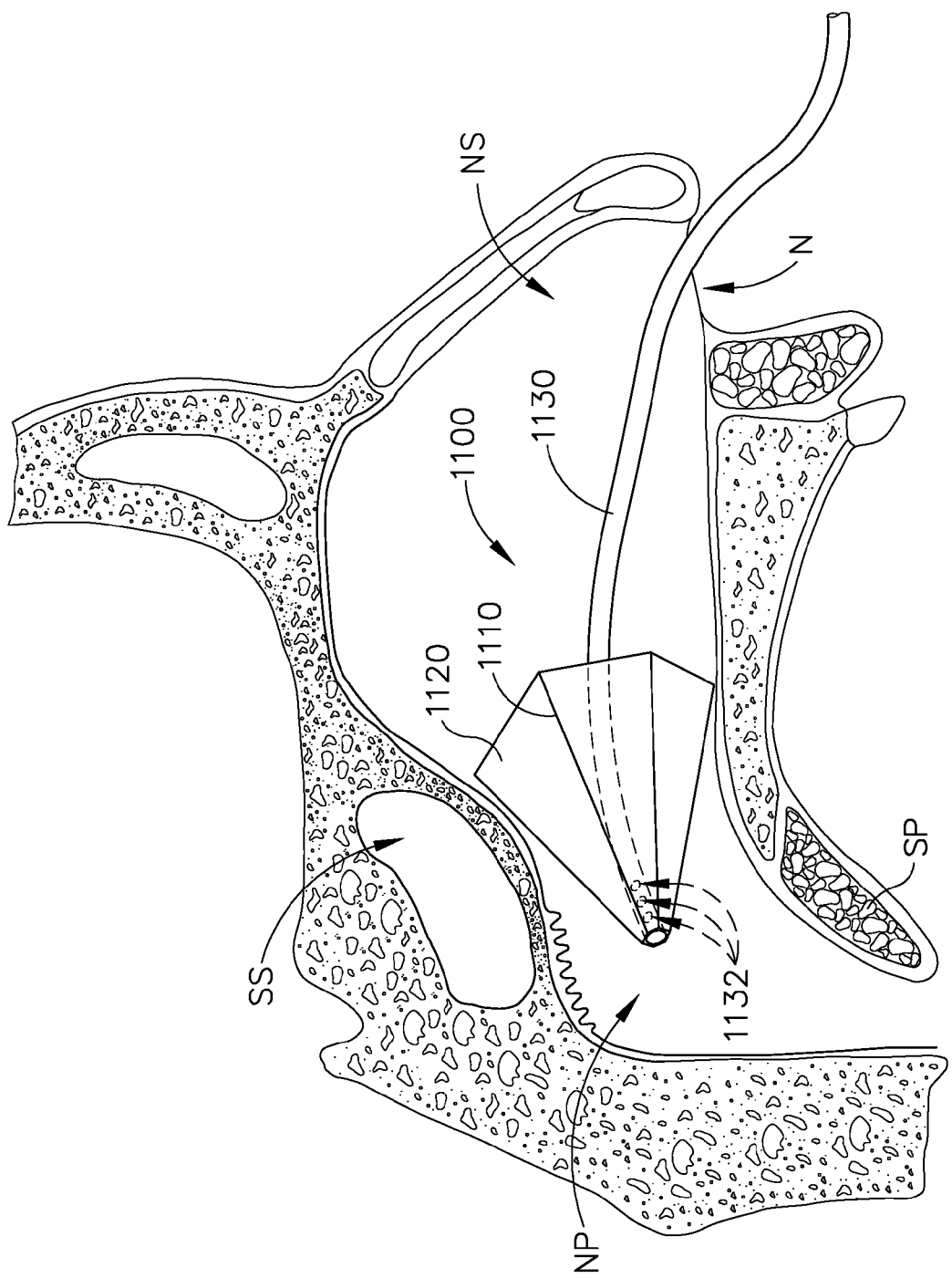
FIG. 31 depicts a diagrammatic view of an exemplary variation of the suction device of FIG. 27 disposed in a choana of a patient.

FIG. 31 shows a merely illustrative variation of suction device (1000). In particular, FIG. 31 shows a suction device (1100) that includes a set of frame members (1110), webbing (1120), and a suction tube (1130). Frame members (1110) of suction device (1100) are substantially similar to frame members (1010) of suction device (1000), except that frame members (1110) of suction device (1100) extend proximally instead of extending distally. Webbing (1120) is substantially identical to webbing (1020). Suction tube (1130) is substantially similar to suction tube (1030), except that suction tube (1130) of this example includes lateral suction ports (1132) formed in the side of suction tube (1130), within the interior region defined by frame members (1110) and webbing (1120). While three lateral suction ports (1132) are shown in a longitudinal arrangement, it should be understood that any other suitable number of lateral suction ports (1132) may be provided in any other suitable arrangement. Lateral suction ports (1132) are in fluid communication with a suction source (not shown) via suction tube (1030).

As shown in FIG. 31, suction device (1110) may be positioned in the patient's choana (C) via the patient's nostril (N). Frame members (1110) and webbing (1120) are in the expanded configuration to catch irrigation fluid, acting as a dam to prevent the irrigation fluid from reaching the nasopharynx (NP). Lateral suction ports (1132) of suction tube (1130) draw in fluid that is caught by webbing (1120). It should be understood that suction device (1100) may be held in the compressed state by a sheath or other instrument feature before reaching the position shown in FIG. 31. Upon reaching the position shown in FIG. 31, suction device (1100) may be released and allowed to expand (or driven to expand) to the expanded configuration shown in FIG. 31. After the irrigation procedure is complete, a sheath or other instrument feature may be used to transition suction device (1100) back to the compressed configuration. Once in the compressed configuration, suction device (1100) may be withdrawn from the patient via the nostril (N). Other suitable ways in which suction device (1100) may be used will be apparent to those of ordinary skill in the art in view of the teachings herein.

VIII. Exemplary Alternative Absorbent Body and Suction Tube Configurations

FIGS. 32-43 show various exemplary alternative features that may be incorporated into suction device (900) described above. It should be understood that, when suction device (900) is modified in accordance with the teachings below, suction device (900) may be used to handle drainage from an irrigation procedure performed using irrigation catheter (80) or using some other irrigation device. In other words, the modified versions of suction device (900) described below may be used in accordance with the teachings herein relating to use of suction device (900) as described above. While the modified features are described below with reference to separate drawings and reference numbers, it should be understood that the features described below may be combined in numerous ways. By way of example only, the suction tube (1330) of FIG. 33 may be combined with the absorbent body (2010) of FIG. 40. Various other suitable ways in which the features described below may be combined will be apparent to those of ordinary skill in the art in view of the teachings herein.

Figure 32:
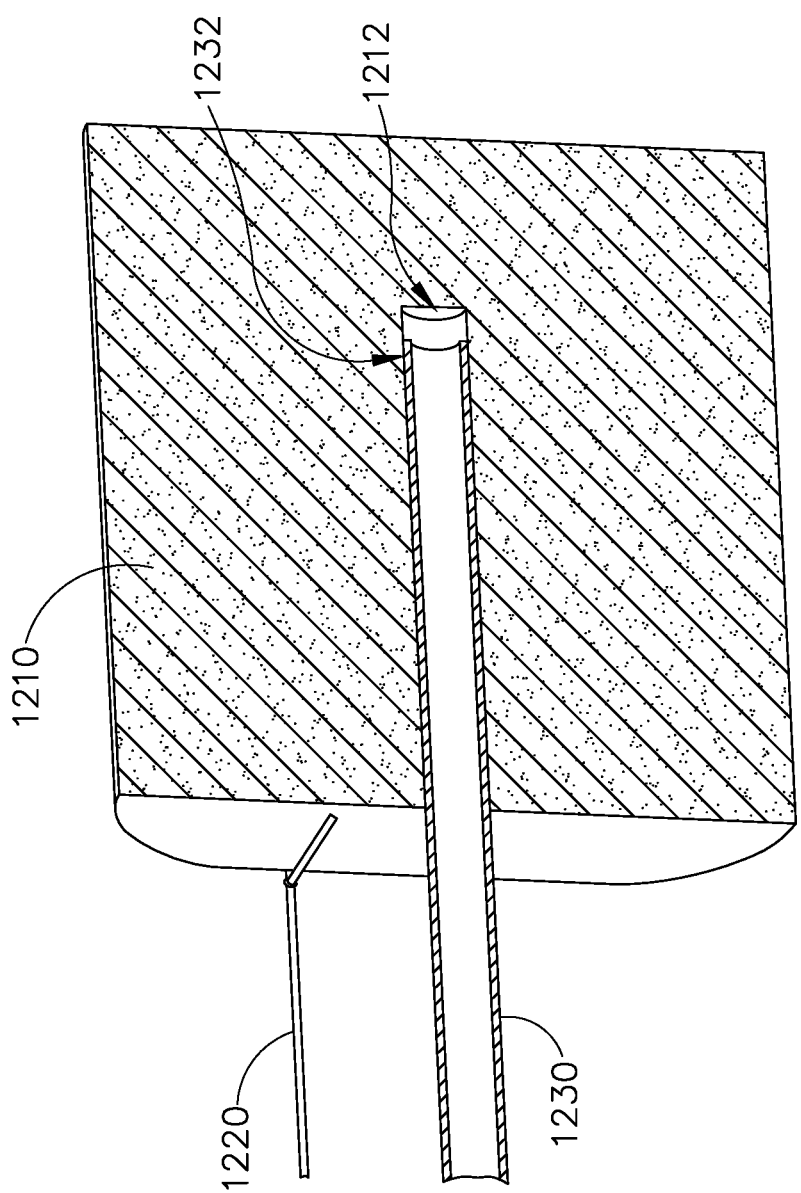
FIG. 32 depicts a perspective, side cross-sectional view of an exemplary alternative configuration of an absorbent body and suction tube with string, which may be incorporated into the suction device of FIG. 21, the cross-section being taken along plane extending longitudinally and vertically through a laterally central region of the absorbent body and suction tube.

FIG. 32 shows an exemplary absorbent body (1210) with a string (1220) and a suction tube (1230). Except for the differences described below, these components (1210, 1220, 1230) are configured and operable substantially identically to absorbent body (910), string (916), and suction tube (930) described above. It should therefore be understood that the proximal end of suction tube (1230) may be coupled with connector (940) and/or some other component in order to provide fluid and/or suction to absorbent body (1210). In the present example, suction tube (1230) is not fully inserted into absorbent body (1210), such that absorbent body (1210) defines a cylindraceous gap or recess (1212) that is located distal to the distal end (1232) of suction tube (1230). This recess (1212) may assist in preventing distal end (1232) from getting essentially clogged by the material forming absorbent body (1210) during use in a patient. In other words, recess (1212) may improve or maintain patency between absorbent body (1210) and suction tube (1230), ensuring appropriate fluid flow from absorbent body (1210) through suction tube (1230) even when absorbent body (1210) encounters both compression and suction while deployed within the patient.

Figure 33:
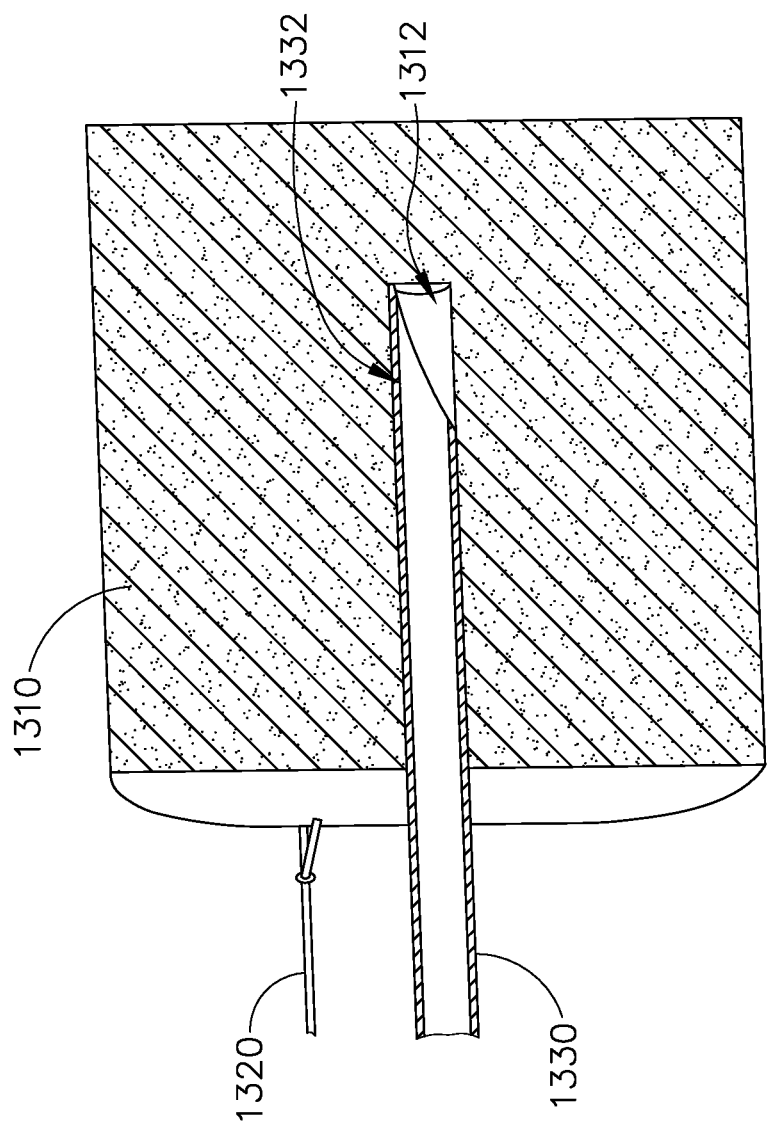
FIG. 33 depicts a perspective, side cross-sectional view of another exemplary alternative configuration of an absorbent body and suction tube with string, which may be incorporated into the suction device of FIG. 21, the cross-section being taken along plane extending longitudinally and vertically through a laterally central region of the absorbent body and suction tube.

FIG. 33 shows another exemplary absorbent body (1310) with a string (1320) and a suction tube (1330). Except for the differences described below, these components (1310, 1320, 1330) are configured and operable substantially identically to absorbent body (910), string (916), and suction tube (930) described above. It should therefore be understood that the proximal end of suction tube (1330) may be coupled with connector (940) and/or some other component in order to provide fluid and/or suction to absorbent body (1310). In the present example, the distal end (1332) of suction tube (1330) is cut at an oblique angle (i.e., oblique to the longitudinal axis of suction tube (1330)). Thus, even with suction tube (1330) fully inserted into absorbent body (1310), a cylindraceous gap or recess (1312) is defined within body (1310), distal to distal end (1332). This recess (1312), along with the oblique configuration of distal end (1332), may assist in preventing distal end (1332) from getting essentially clogged by the material forming absorbent body (1310) during use in a patient. In other words, recess (1312) and the oblique configuration of distal end (1332) may improve or maintain patency between absorbent body (1310) and suction tube (1330), ensuring appropriate fluid flow from absorbent body (1310) through suction tube (1330) even when absorbent body (1310) encounters both compression and suction while deployed within the patient.

In the present example, the proximal-most region of distal end (1332) is positioned substantially near the center of absorbent body (1310). In some other variations, the proximal-most region of distal end (1332) is positioned substantially near the proximal end of absorbent body (1310) (i.e., the end of absorbent body (1310) where suction tube (1330) enters absorbent body (1310)). This positioning may provide reduced compression at distal end (1332) during use in a patient. This positioning may be achieved in numerous ways. By way of example only, distal end (1332) may be cut at an oblique angle that is substantially more acute than the angle shown in FIG. 33, such that the distal-most region of distal end (1332) is still located within body (1310) at the position shown in FIG. 33. As another merely illustrative example, the entire distal end (1332) of body (1310) may be positioned further proximally within body (1310) relative to the position shown in FIG. 33. Other suitable configurations will be apparent to those of ordinary skill in the art in view of the teachings herein. Similarly, other suitable distances between the proximal-most region of distal end (1332) and the proximal end of absorbent body (1310) will be apparent to those of ordinary skill in the art in view of the teachings herein. It should also be understood that this proximal positioning of the proximal-most region of distal end (1332) may be applied to any of the other obliquely cut suction tube distal end configurations described herein. Moreover, this proximal positioning of the proximal-most region of distal end (1332) may be provided in an absorbent body (1310) with proximal chamfers similar to chamfers (2018) described below with reference to FIG. 40. In addition, this proximal positioning of the proximal-most region of distal end (1332) may permit use of a suction tube (1330) having a relatively large diameter (e.g., larger than suction tube diameters that are explicitly specified herein). Other suitable configurations and combinations will be apparent to those of ordinary skill in the art in view of the teachings herein.

Figure 34:
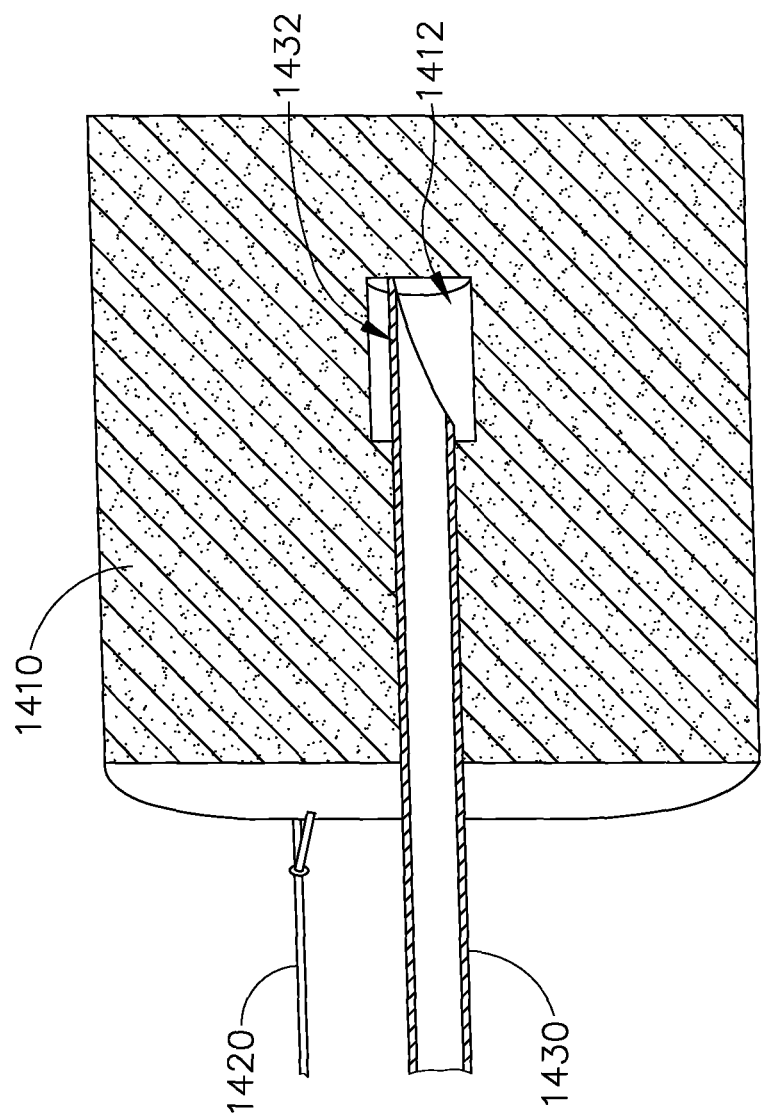
FIG. 34 depicts a perspective, side cross-sectional view of another exemplary alternative configuration of an absorbent body and suction tube with string, which may be incorporated into the suction device of FIG. 21, the cross-section being taken along plane extending longitudinally and vertically through a laterally central region of the absorbent body and suction tube.

FIG. 34 shows another exemplary absorbent body (1410) with a string (1420) and a suction tube (1430). Except for the differences described below, these components (1410, 1420, 1430) are configured and operable substantially identically to absorbent body (910), string (916), and suction tube (930) described above. It should therefore be understood that the proximal end of suction tube (1430) may be coupled with connector (940) and/or some other component in order to provide fluid and/or suction to absorbent body (1410). In the present example, the distal end (1432) of suction tube (1430) is cut at an oblique angle (i.e., oblique to the longitudinal axis of suction tube (1430)). Thus, even with suction tube (1430) fully inserted into absorbent body (1410), a cylindraceous gap or recess (1412) is defined within body (1410), distal to distal end (1432). Moreover, recess (1412) of the present example defines an enlarged inner diameter. This enlarged inner diameter is substantially larger than the outer diameter of suction tube (1430), such that recess (1412) provides additional clearance for the material forming absorbent body (1410) to compress inwardly without clogging distal end (1432). In other words, enlarged recess (1412) and the oblique configuration of distal end (1432) may together improve or maintain patency between absorbent body (1410) and suction tube (1430), ensuring appropriate fluid flow from absorbent body (1410) through suction tube (1430) even when absorbent body (1410) encounters both compression and suction while deployed within the patient.

While absorbent body (1410) is described above as being used with a suction tube (1430) having an obliquely angled distal end (1432), it should be understood that absorbent body (1410) may also be used with a suction tube having a flat distal end (e.g., like suction tube (1230), etc.) or some other kind of distal end configuration. It should also be understood that recess (1412) may be provided by assembling a stack of separate absorbent members to form absorbent body (1410). For instance, a first absorbent member may have a first cutout formed in it to define recess (1412). A second absorbent member may have a second cutout formed in it to receive suction tube (1430) proximal to recess (1412). A third absorbent member may lack any cutouts, and may be positioned distal to the first absorbent member. These three members may be assembled and bonded together in any suitable fashion to form absorbent body (1410). Other suitable techniques that may be used to form absorbent body (1410) will be apparent to those of ordinary skill in the art in view of the teachings herein.

Figure 35:
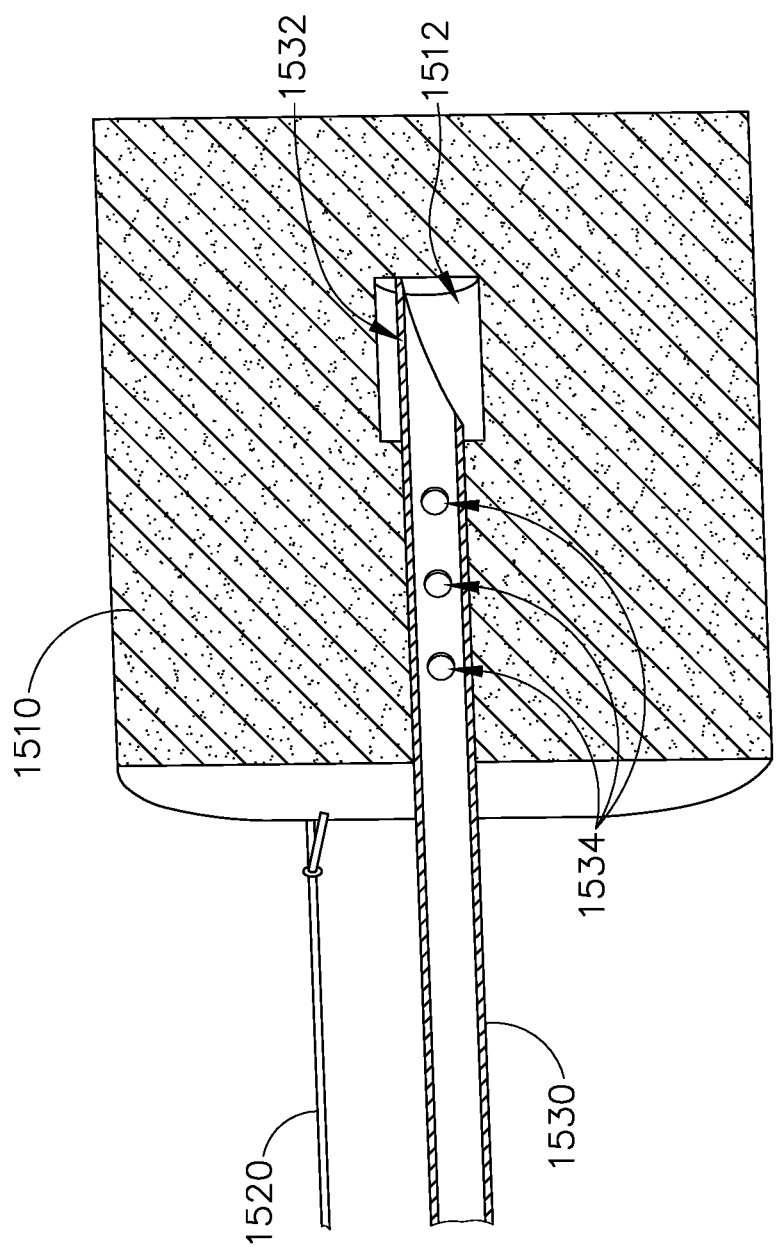
FIG. 35 depicts a perspective, side cross-sectional view of another exemplary alternative configuration of an absorbent body and suction tube with string, which may be incorporated into the suction device of FIG. 21, the cross-section being taken along plane extending longitudinally and vertically through a laterally central region of the absorbent body and suction tube.

FIG. 35 shows another exemplary absorbent body (1510) with a string (1520) and a suction tube (1530). Except for the differences described below, these components (1510, 1520, 1530) are configured and operable substantially identically to absorbent body (910), string (916), and suction tube (930) described above. It should therefore be understood that the proximal end of suction tube (1530) may be coupled with connector (940) and/or some other component in order to provide fluid and/or suction to absorbent body (1510). In the present example, the distal end (1532) of suction tube (1530) is cut at an oblique angle (i.e., oblique to the longitudinal axis of suction tube (1530)). Thus, even with suction tube (1530) fully inserted into absorbent body (1510), a cylindraceous gap or recess (1512) is defined within body (1510), distal to distal end (1532). Moreover, recess (1512) of the present example defines an enlarged inner diameter. This enlarged inner diameter is substantially larger than the outer diameter of suction tube (1530), such that recess (1512) provides additional clearance for the material forming absorbent body (1510) to compress inwardly without clogging distal end (1532). In other words, enlarged recess (1512) and the oblique configuration of distal end (1532) may together improve or maintain patency between absorbent body (1510) and suction tube (1530), ensuring appropriate fluid flow from absorbent body (1510) through suction tube (1530) even when absorbent body (1510) encounters both compression and suction while deployed within the patient.

As also shown in FIG. 35, suction tube (1530) of the present example includes a plurality of lateral openings (1534). Openings (1534) provide additional pathways for suction tube (1530) to draw in fluids from absorbent body (1510). Openings (1534) are substantially circular in this example, though it should be understood that any other suitable configurations may be used. In addition, while three openings (1534) are shown, any other suitable number of openings (1534) may be used along the length of suction tube (1530). Furthermore, any suitable number of openings (1534) may be used at a given longitudinal position along suction tube (1530), in any suitable angular arrangement.

Figure 36:
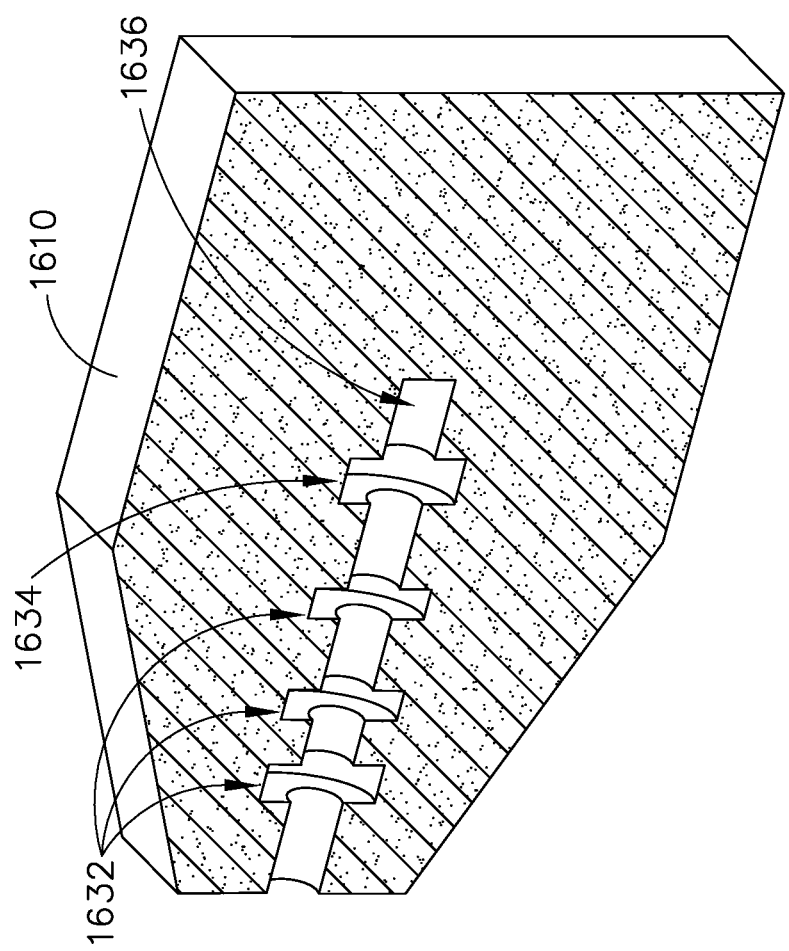
FIG. 36 depicts a perspective, side cross-sectional view of an exemplary alternative absorbent body that may be incorporated into the configuration of FIG. 35, the cross-section being taken along plane extending longitudinally and vertically through a laterally central region of the absorbent body.

FIG. 36 shows an exemplary alternative absorbent body (1610) that may be used with suction tube (1530). Absorbent body (1610) of this example includes a plurality of additional recesses (1632). Each of these recesses (1632) is positioned to correspond with a respective lateral opening (1534) of suction tube (1530). Thus, recesses (1632) may prevent openings (1534) from getting clogged with the material forming absorbent body (1610). Absorbent body (1610) of this example also includes a first distal recess (1634) and a second distal recess (1636). First distal recess (1634) has a larger diameter and is positioned to correspond with a proximal portion of obliquely angled distal end (1532) of suction tube (1530); while second distal recess (1636) has a smaller diameter is positioned to correspond with a distal portion of obliquely angled distal end (1532) of suction tube (1530). Of course, absorbent body (1610) may instead have a distal recess that is formed like recess (1532) described above or that has some other configuration. It should also be understood that recesses (1632, 1634, 1636) may be provided by stacking a plurality of absorbent members together, as described above with respect to absorbent body (1410). Alternatively, absorbent body (1610) may be formed in any other suitable fashion.

Figure 37:
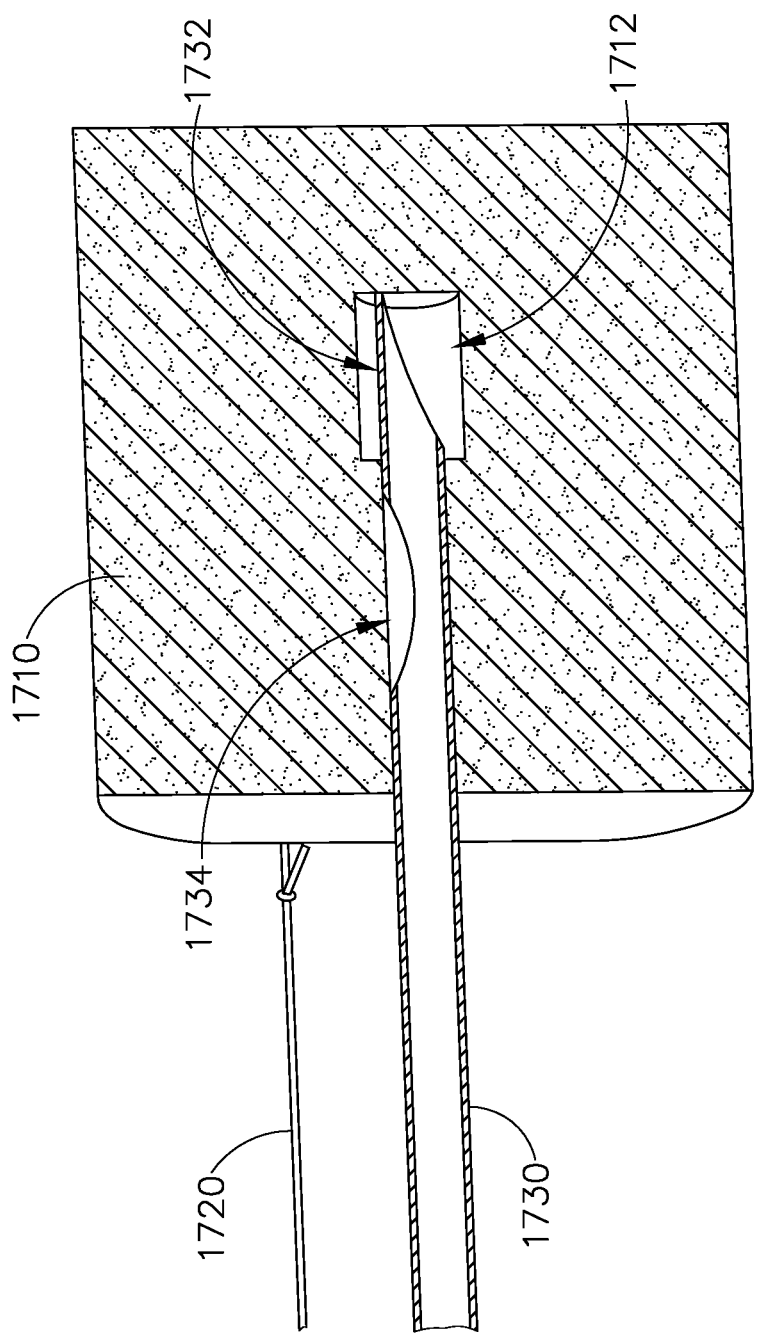
FIG. 37 depicts a perspective, side cross-sectional view of another exemplary alternative configuration of an absorbent body and suction tube with string, which may be incorporated into the suction device of FIG. 21, the cross-section being taken along plane extending longitudinally and vertically through a laterally central region of the absorbent body and suction tube.

FIG. 37 shows another exemplary absorbent body (1710) with a string (1720) and a suction tube (1730). Except for the differences described below, these components (1710, 1720, 1730) are configured and operable substantially identically to absorbent body (910), string (916), and suction tube (930) described above. It should therefore be understood that the proximal end of suction tube (1730) may be coupled with connector (940) and/or some other component in order to provide fluid and/or suction to absorbent body (1710). In the present example, the distal end (1732) of suction tube (1730) is cut at an oblique angle (i.e., oblique to the longitudinal axis of suction tube (1730)). Thus, even with suction tube (1730) fully inserted into absorbent body (1710), a cylindraceous gap or recess (1712) is defined within body (1710), distal to distal end (1732). Moreover, recess (1712) of the present example defines an enlarged inner diameter. This enlarged inner diameter is substantially larger than the outer diameter of suction tube (1730), such that recess (1712) provides additional clearance for the material forming absorbent body (1710) to compress inwardly without clogging distal end (1732). In other words, enlarged recess (1712) and the oblique configuration of distal end (1732) may together improve or maintain patency between absorbent body (1710) and suction tube (1730), ensuring appropriate fluid flow from absorbent body (1710) through suction tube (1730) even when absorbent body (1710) encounters both compression and suction while deployed within the patient.

As also shown in FIG. 37, suction tube (1730) of the present example includes a lateral opening (1734). Opening (1734) provides an additional pathway for suction tube (1730) to draw in fluids from absorbent body (1710). Opening (1734) has a scoop-cut, scalloped configuration in this example, though it should be understood that any other suitable configurations may be used. In addition, while one opening (1734) is shown, any other suitable number of openings (1734) may be used along the length of suction tube (1730). Furthermore, any suitable number of openings (1734) may be used at a given longitudinal position along suction tube (1730), in any suitable angular arrangement.

Figure 38:
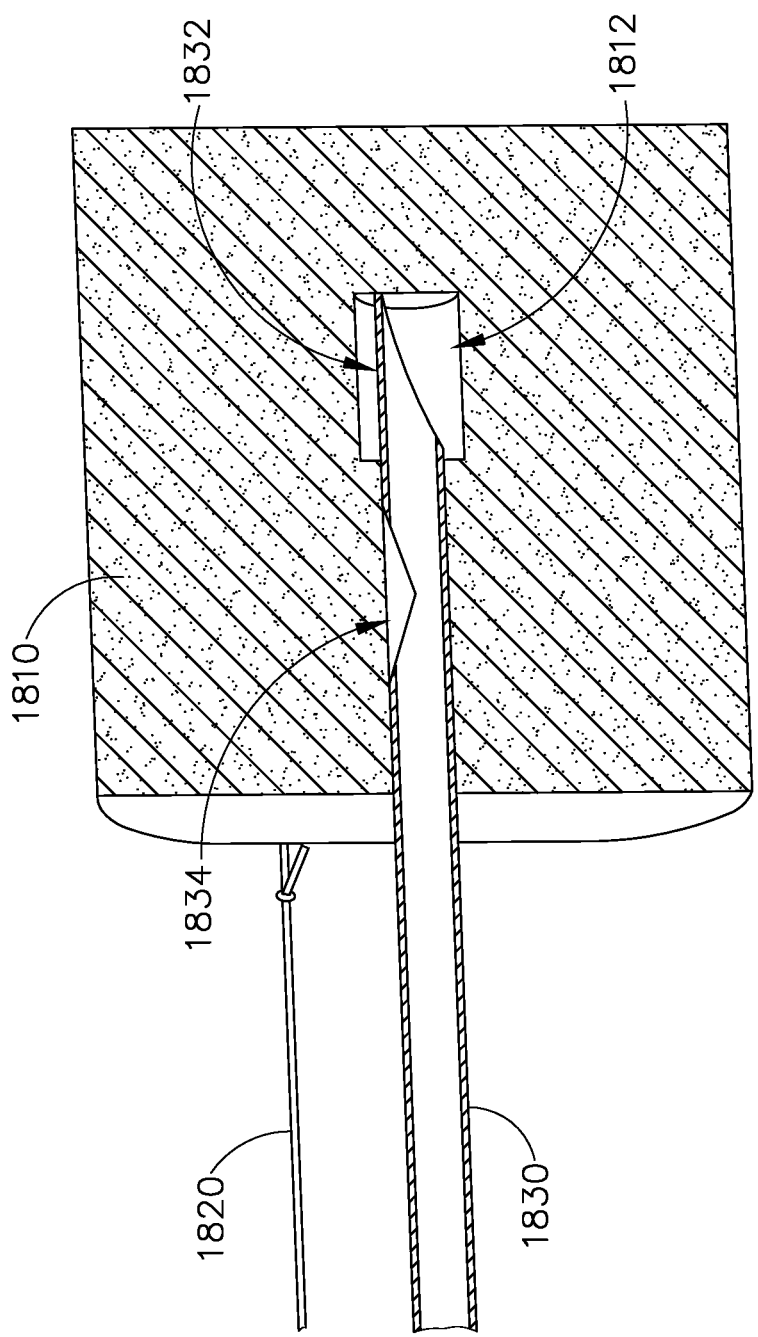
FIG. 38 depicts a perspective, side cross-sectional view of another exemplary alternative configuration of an absorbent body and suction tube with string, which may be incorporated into the suction device of FIG. 21, the cross-section being taken along plane extending longitudinally and vertically through a laterally central region of the absorbent body and suction tube.

FIG. 38 shows another exemplary absorbent body (1810) with a string (1820) and a suction tube (1830). Except for the differences described below, these components (1810, 1820, 1830) are configured and operable substantially identically to absorbent body (910), string (916), and suction tube (930) described above. It should therefore be understood that the proximal end of suction tube (1830) may be coupled with connector (940) and/or some other component in order to provide fluid and/or suction to absorbent body (1810). In the present example, the distal end (1832) of suction tube (1830) is cut at an oblique angle (i.e., oblique to the longitudinal axis of suction tube (1830)). Thus, even with suction tube (1830) fully inserted into absorbent body (1810), a cylindraceous gap or recess (1812) is defined within body (1810), distal to distal end (1832). Moreover, recess (1812) of the present example defines an enlarged inner diameter. This enlarged inner diameter is substantially larger than the outer diameter of suction tube (1830), such that recess (1812) provides additional clearance for the material forming absorbent body (1810) to compress inwardly without clogging distal end (1832). In other words, enlarged recess (1812) and the oblique configuration of distal end (1832) may together improve or maintain patency between absorbent body (1810) and suction tube (1830), ensuring appropriate fluid flow from absorbent body (1810) through suction tube (1830) even when absorbent body (1810) encounters both compression and suction while deployed within the patient.

As also shown in FIG. 38, suction tube (1830) of the present example includes a lateral opening (1834). Opening (1834) provides an additional pathway for suction tube (1830) to draw in fluids from absorbent body (1810). Opening (1834) has an angle-cut, "V" shaped configuration in this example, though it should be understood that any other suitable configurations may be used. In addition, while one opening (1834) is shown, any other suitable number of openings (1834) may be used along the length of suction tube (1830). Furthermore, any suitable number of openings (1834) may be used at a given longitudinal position along suction tube (1830), in any suitable angular arrangement.

Figure 39:
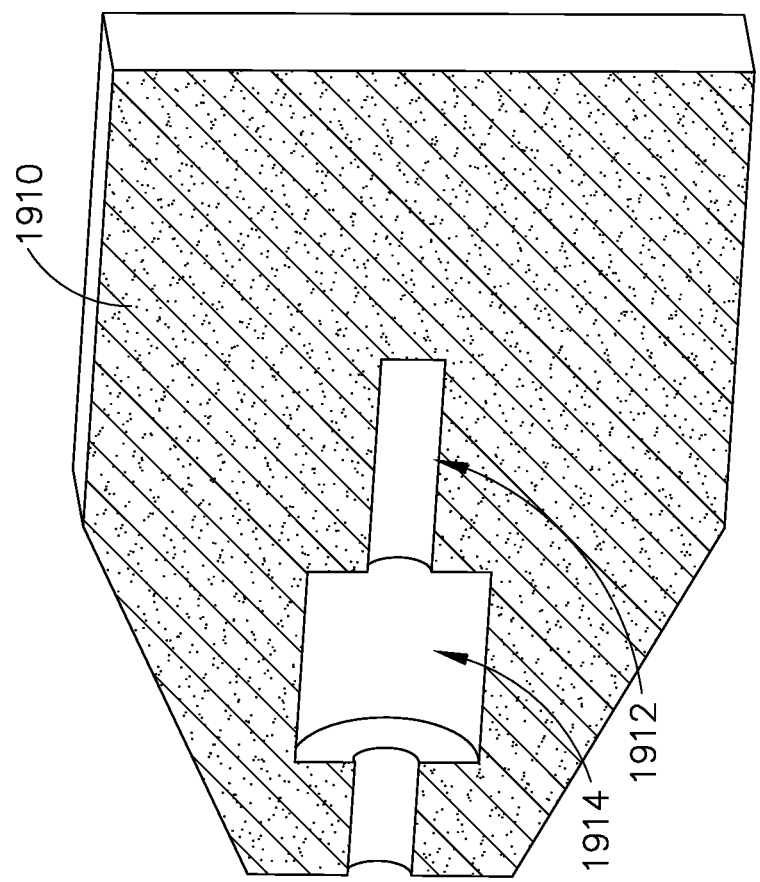
FIG. 39 depicts a perspective, side cross-sectional view of an exemplary alternative absorbent body that may be incorporated into the configuration of FIG. 38, the cross-section being taken along plane extending longitudinally and vertically through a laterally central region of the absorbent body.

FIG. 39 shows an exemplary alternative absorbent body (1910) that may be used with suction tube (1530, 1730, 1830). Absorbent body (1910) of this example includes a distal recess (1912) and an enlarged recess (1914), which is positioned to correspond with either the entire set of openings (1534) of suction tube (1530) or the lateral openings (1734, 1834) of suction tubes (1730, 1830). Thus, recess (1914) may prevent openings (1534, 1734, 1834) from getting clogged with the material forming absorbent body (1910). It should also be understood that recesses (1912, 1914) may be provided by stacking a plurality of absorbent members together, as described above with respect to absorbent body (1410). Alternatively, absorbent body (1910) may be formed in any other suitable fashion.

Figure 40:
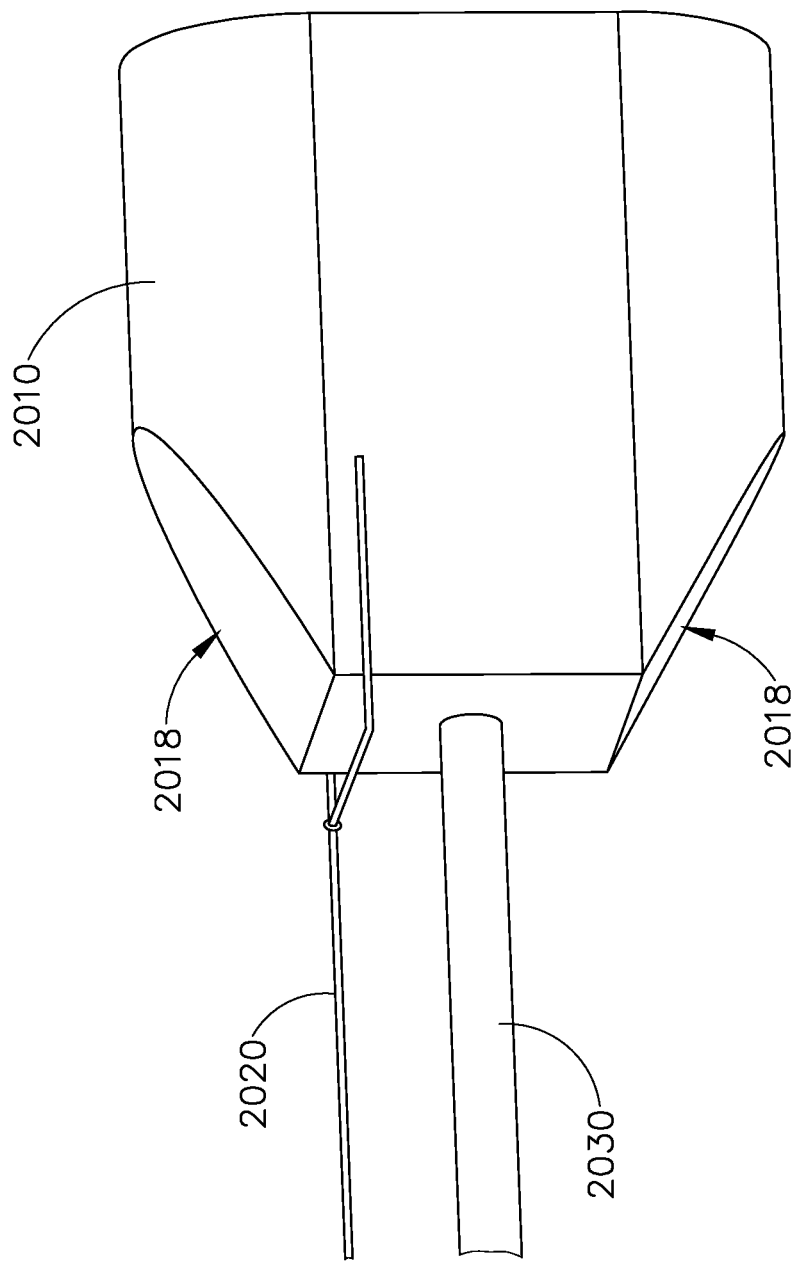
FIG. 40 depicts a perspective view of another exemplary alternative configuration of an absorbent body and suction tube with string, which may be incorporated into the suction device of FIG. 21.

FIG. 40 shows another exemplary absorbent body (2010) with a string (2020) and a suction tube (2030). Except for the differences described below, these components (2010, 2020, 2030) are configured and operable substantially identically to absorbent body (910), string (916), and suction tube (930) described above. It should therefore be understood that the proximal end of suction tube (2030) may be coupled with connector (940) and/or some other component in order to provide fluid and/or suction to absorbent body (2010). In the present example, absorbent body (2010) includes a pair of chamfers (2018) at the end associated with suction tube (2030). Chamfers (2018) may facilitate removal of absorbent body (2010) from the patient, by providing a taper and reducing drag against walls and other anatomical structures within the paranasal cavity. In addition, chamfers (2018) may reduce compression of absorbent body (2010) against the distal end of suction tube (2030), which may in turn reduce the risk of absorbent body (2010) clogging the distal end of suction tube (2030). Chamfers (2018) may be formed at any suitable angles.

Figure 41:
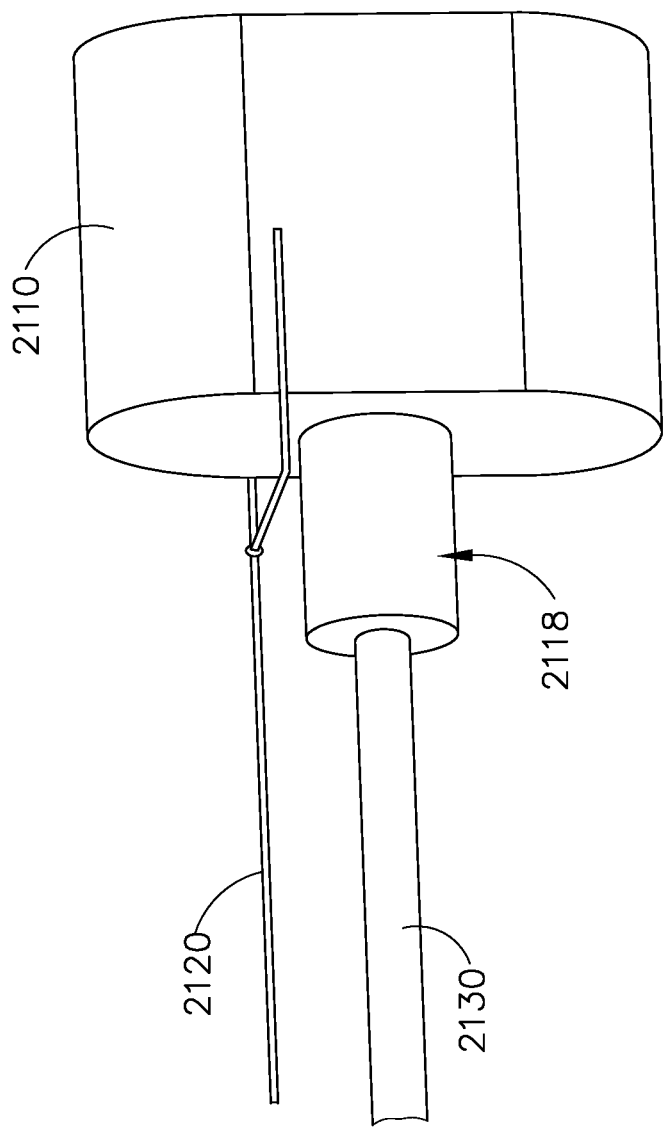
FIG. 41 depicts a perspective view of another exemplary alternative configuration of an absorbent body and suction tube with string, which may be incorporated into the suction device of FIG. 21.

FIG. 41 shows another exemplary absorbent body (2110) with a string (2120) and a suction tube (2130). Except for the differences described below, these components (2110, 2120, 2130) are configured and operable substantially identically to absorbent body (910), string (916), and suction tube (930) described above. It should therefore be understood that the proximal end of suction tube (2130) may be coupled with connector (940) and/or some other component in order to provide fluid and/or suction to absorbent body (2110). In the present example, absorbent body (2110) includes a reduced diameter portion (2118) at the end associated with suction tube (2130). Like chamfers (2018), reduced diameter portion (2118) may reduce compression of absorbent body (2110) against the distal end of suction tube (2130), which may in turn reduce the risk of absorbent body (2110) clogging the distal end of suction tube (2130). Reduced diameter portion (2118) may be formed with any suitable diameter. It should also be understood that a set of reduced diameter portions (2118) may be stacked with progressively increasing diameters. Other suitable configurations will be apparent to those of ordinary skill in the art in view of the teachings herein.

Figure 42:
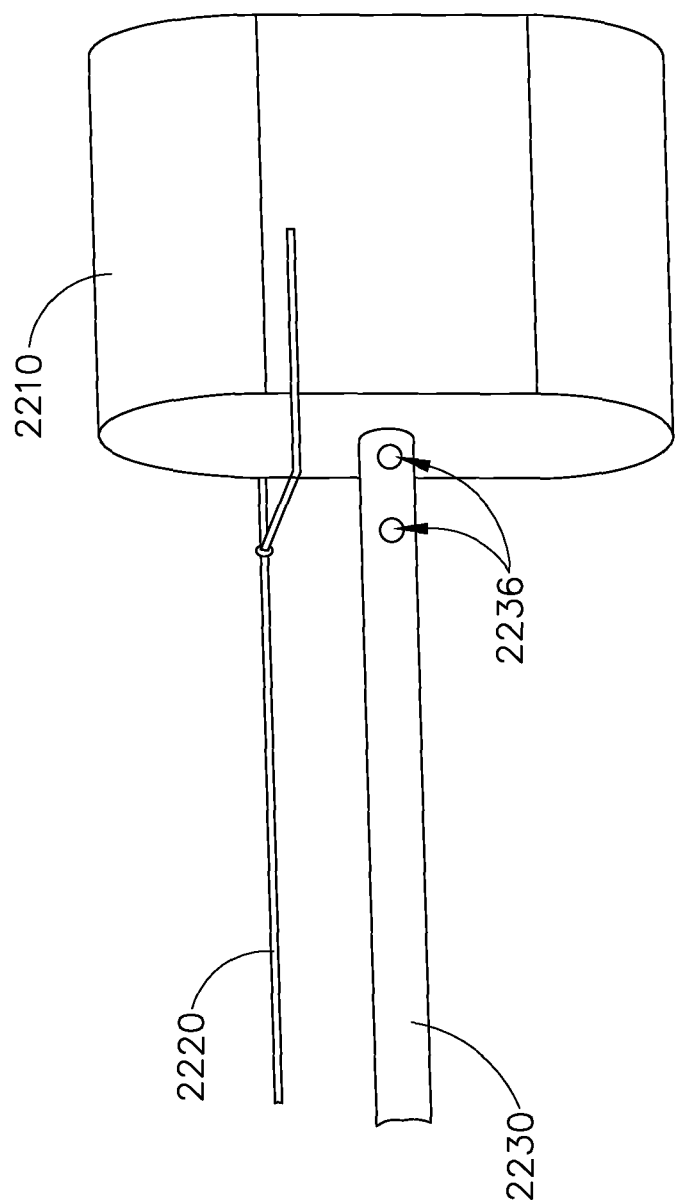
FIG. 42 depicts a perspective view of another exemplary alternative configuration of an absorbent body and suction tube with string, which may be incorporated into the suction device of FIG. 21.

FIG. 42 shows another exemplary absorbent body (2210) with a string (2220) and a suction tube (2230). Except for the differences described below, these components (2210, 2220, 2230) are configured and operable substantially identically to absorbent body (910), string (916), and suction tube (930) described above. It should therefore be understood that the proximal end of suction tube (2230) may be coupled with connector (940) and/or some other component in order to provide fluid and/or suction to absorbent body (2210). In the present example, suction tube (2230) includes a plurality of lateral openings (2236) that are positioned outside of absorbent body (2210). It should be understood that openings (2236) may provide additional pathways for suction tube (2230) to draw fluid away from within the paranasal cavity.

Openings (2236) are substantially circular in this example, though it should be understood that any other suitable configurations may be used. In addition, while two openings (2236) are shown, any other suitable number of openings (2236) may be used along the length of suction tube (2230). Furthermore, any suitable number of openings (2236) may be used at a given longitudinal position along suction tube (2230), in any suitable angular arrangement. It should also be understood that suction tube (2230) and absorbent body (2210) may include any of the additional openings, distal end configurations, and recesses described above to further promote patency between absorbent body (2210) and suction tube (2230).

Figure 43:
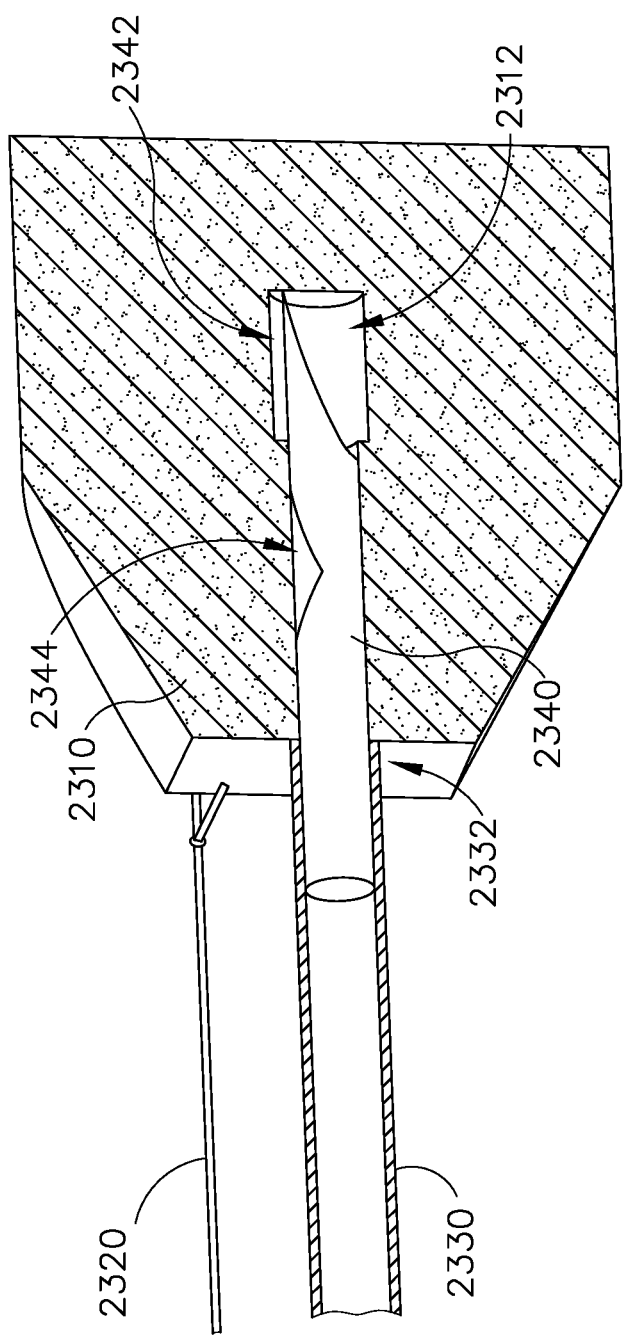
FIG. 43 depicts a perspective, side cross-sectional view of another exemplary alternative configuration of an absorbent body and suction tube with string, which may be incorporated into the suction device of FIG. 21, the cross-section being taken along plane extending longitudinally and vertically through a laterally central region of the absorbent body and suction tube.

FIG. 43 shows another exemplary absorbent body (2310) with a string (2320) and a suction tube (2330). Except for the differences described below, these components (2310, 2320, 2330) are configured and operable substantially identically to absorbent body (910), string (916), and suction tube (930) described above. It should therefore be understood that the proximal end of suction tube (2330) may be coupled with connector (940) and/or some other component in order to provide fluid and/or suction to absorbent body (2310).

In the present example, the distal end (2332) of suction tube (2330) terminates at the proximal end of absorbent body (2310). A suction insert (2340) is inserted into distal end (2332) of suction tube (2330) and extends distally into absorbent body (2310). Suction insert (2340) is coaxially aligned with suction tube (2330) and provides a path for fluid communication between suction tube (2330) and absorbent body (2310). Suction insert (2340) includes a distal end (2342) that is cut at an oblique angle (i.e., oblique to the longitudinal axis of suction insert (2340)). Thus, even with suction insert (2340) fully inserted into absorbent body (2310), a cylindraceous gap or recess (2312) is defined within body (2310), distal to distal end (2342). Moreover, recess (2312) of the present example defines an enlarged inner diameter. This enlarged inner diameter is substantially larger than the outer diameter of suction insert (2340), such that recess (2312) provides additional clearance for the material forming absorbent body (2310) to compress inwardly without clogging distal end (2342). In other words, enlarged recess (2312) and the oblique configuration of distal end (2342) may together improve or maintain patency between absorbent body (2310) and both suction insert (2340) and suction tube (2330), ensuring appropriate fluid flow from absorbent body (2310) through suction insert (2340) and suction tube (2330) even when absorbent body (2310) encounters both compression and suction while deployed within the patient.

As also shown in FIG. 43, suction insert (2340) of the present example includes a lateral opening (2344). Opening (2344) provides an additional pathway for suction insert (2340) to draw in fluids from absorbent body (2310). Opening (2344) has an angle-cut, "V" shaped configuration in this example, though it should be understood that any other suitable configurations may be used. In addition, while one opening (2344) is shown, any other suitable number of openings (2344) may be used along the length of suction insert (2340). Furthermore, any suitable number of openings (23444) may be used at a given longitudinal position along suction insert (2340), in any suitable angular arrangement.

In some versions, the inner diameter of suction insert (2340) is between approximately 0.07 inches and approximately 0.100 inches. This inner diameter of suction insert (2340) may be greater than the inner diameter of suction tube (2320). In some versions, suction insert (2340) has a greater rigidity than suction tube (2320). Also in some versions, suction tube (2320) has a greater wall thickness than suction insert (2340). In any of these versions, the overlap between suction insert (2340) and suction tube (2330) at the proximal end of body (2310) may reduce the risk of suction tube (2330) kinking at the proximal end of body (2310).

IX. Miscellaneous

While suction devices (100, 200, 300, 400, 600, 700, 900, 1000, 1100) have been described above as being used in the context of an irrigation procedure, it should be understood that suction devices (100, 200, 300, 400, 600, 700, 900, 1000, 1100) may be used in a variety of other procedures. Similarly, it should be understood that suction devices (100, 200, 300, 400, 600, 700, 900, 1000, 1100) may be used to absorb and suction fluids other than irrigation fluid. By way of example only, suction devices (100, 200, 300, 400, 600, 700, 900, 1000, 1100) may be used to absorb medication (e.g., lidocaine, etc.), blood, water, and/or any other fluid that may otherwise drain through the nasopharynx (NP).

Because of the variance in the size of a choana opening, a plurality of suction devices (100, 200, 300, 400, 600, 700, 900, 1000, 1100) of varying sizes and/or configurations may be provided to allow a physician to choose a suction device (100, 200, 300, 400, 600, 700, 900, 1000, 1100). For instance, a kit may be provided with bodies (110, 210, 310, 410, 610, 710, 910) of various configurations and/or sizes, such that the physician may select a body (110, 210, 310, 410, 610, 710, 910) of a particular configuration/size based on observation of the patient's particular anatomy (e.g., after visualizing the patient's choana (C) using a CT scan or endoscope, etc.). Because of the expansion ratio of body (110, 210, 310, 410, 610, 710, 910), exact measurements the choana (C) opening would not necessarily be needed.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body, wherein the body comprises an absorbent material, wherein the body is configured to be disposed within an anatomical passageway, wherein the body is configured to expand to an expanded state, wherein the body is configured to absorb fluid to thereby expand the body to the expanded state, wherein an outer perimeter of the body is configured to contact an inner wall of the anatomical passageway in the expanded state; and
   wherein the body has a closed distal end
   (b) a conduit in fluid communication with the body, wherein the conduit includes a distal end and a proximal end, wherein the distal end comprises an oblique tip, wherein the distal end of the conduit is disposed within the body such that the oblique tip and the body define a gap, wherein the conduit is operable to draw fluid away from the absorbent material via the distal end of the conduit.

2. The apparatus of claim 1, wherein the conduit further comprises a lateral opening.

3. The apparatus of claim 2, wherein the lateral opening has a "V" shaped configuration.

4. The apparatus of claim 3, wherein the lateral opening has scalloped configuration.

5. The apparatus of claim 2, wherein the lateral opening is disposed within the absorbent body.

6. The apparatus of claim 1, wherein the body defines a first distal recess and a second distal recess, wherein the first distal recess is proximal in location relative to the second distal recess.

7. The apparatus of claim 6, wherein the first distal recess is larger than the second distal recess.

8. The apparatus of claim 6, wherein the conduit is located within both the first distal recess and the second distal recess.

9. The apparatus of claim 8, wherein the distal end of the conduit terminates within the second distal recess.

10. The apparatus of claim 8, wherein the second distal recess is larger than a diameter of the oblique tip, wherein the gap is defined by the second distal recess and the oblique tip.

11. The apparatus of claim 1, further comprising a connector coupled with the proximal end of the conduit.

12. The apparatus of claim 11, further comprising a tether, wherein the tether is coupled with the body, wherein the tether is further coupled with the connector.

13. The apparatus of claim 12, wherein the connector comprises a distal end and a proximal end, wherein the proximal end of the conduit is disposed within the distal end of the connector.

14. The apparatus of claim 1, wherein further comprises a second absorbent body attached to the absorbent body, wherein the second absorbent body has a reduced cross-sectional area as compared to the absorbent body.

15. The apparatus of claim 14, wherein the conduit is disposed within the second absorbent body.

16. The apparatus of claim 15, wherein the second absorbent body has a circular cross-sectional shape.

17. The apparatus of claim 16, wherein the second absorbent body defines a channel sized to receive the conduit.

18. An apparatus comprising:
   (a) a body, wherein the body comprises an absorbent material, wherein the body is configured to be disposed within an anatomical passageway, wherein the body is configured to expand to an expanded state, wherein the body is configured to absorb fluid to thereby expand the body to the expanded state, wherein an outer perimeter of the body is configured to contact an inner wall of the anatomical passageway in the expanded state, wherein the body defines a passageway; and
   wherein the body has a closed distal end
   (b) a conduit in fluid communication with the body, wherein the conduit includes a distal end and a proximal end, wherein the distal end of the conduit defines an oblique angle positioned within the passageway of the body such that the distal end of the conduit and the passageway of the body define a gap, wherein the conduit is operable to draw fluid away from the absorbent material via the distal end of the conduit.

19. The apparatus of claim 18, wherein the conduit defines a lateral aperture positioned within the passageway of the body.

20. An apparatus comprising:
   (a) a body, wherein the body comprises an absorbent material, wherein the body is configured to be disposed within an anatomical passageway, wherein the body is configured to expand to an expanded state, wherein the body is configured to absorb fluid to thereby expand the body to the expanded state, wherein an outer perimeter of the body is configured to contact an inner wall of the anatomical passageway in the expanded state, wherein the body defines a recess extending from an exterior of the body and terminating within the body at a distal interior surface; and
   wherein the body has a closed distal end
   (b) a conduit in fluid communication with the body, wherein the conduit includes a distal end and a proximal end, wherein the distal end of the conduit defines an oblique angle, wherein the oblique angle is housed within the recess proximal to the distal interior surface of the body such that the distal end of the conduit and the recess define a gap, wherein the conduit is operable to draw fluid away from the absorbent material via the distal end of the conduit.

\* \* \* \* \*